US007144734B2

(12) United States Patent
Court et al.

(10) Patent No.: US 7,144,734 B2
(45) Date of Patent: Dec. 5, 2006

(54) ENHANCED HOMOLOGOUS RECOMBINATION MEDIATED BY LAMBDA RECOMBINATION PROTEINS

(75) Inventors: Donald L. Court, Frederick, MD (US); Daiguan Yu, The Woodlands, TX (US); E-Chiang Lee, The Woodlands, TX (US); Hilary M. Ellis, San Ramon, CA (US); Nancy A. Jenkins, Ijamsville, MD (US); Neal G. Copeland, Ijamsville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 265 days.

(21) Appl. No.: 10/366,044

(22) Filed: Feb. 12, 2003

(65) Prior Publication Data

US 2003/0224521 A1 Dec. 4, 2003

Related U.S. Application Data

(63) Continuation-in-part of application No. PCT/US01/25507, filed on Aug. 14, 2001.

(60) Provisional application No. 60/271,632, filed on Feb. 26, 2001, provisional application No. 60/225,164, filed on Aug. 14, 2000.

(51) Int. Cl.
*C12N 15/00* (2006.01)
*C12N 15/87* (2006.01)
*C12N 15/74* (2006.01)
*C12N 15/79* (2006.01)
*C12N 15/80* (2006.01)
*C12N 15/82* (2006.01)
*C12N 1/16* (2006.01)
*C12N 1/20* (2006.01)

(52) U.S. Cl. ............ 435/471; 435/476; 435/463; 435/468; 435/455; 435/254.2; 435/252.3; 435/320.1

(58) Field of Classification Search ............... 435/455, 435/468, 471, 91.1, 6, 29; 536/23.1, 24.1
See application file for complete search history.

(56) References Cited

U.S. PATENT DOCUMENTS

| | | | | |
|---|---|---|---|---|
| 5,652,128 | A * | 7/1997 | Jarvik | 435/6 |
| 5,789,166 | A | 8/1998 | Bauer et al. | |
| 5,888,732 | A | 3/1999 | Hartley et al. | |
| 6,281,000 | B1 | 8/2001 | Chartier et al. | |
| 6,355,412 | B1 * | 3/2002 | Stewart et al. | 435/4 |
| 6,365,408 | B1 | 4/2002 | Stemmer | |
| 6,509,156 | B1 | 1/2003 | Stewart et al. | |
| 6,787,316 | B1 * | 9/2004 | Stewart et al. | 435/6 |
| 2002/0013956 | A1 | 1/2002 | Borts et al. | |
| 2002/0090361 | A1 * | 7/2002 | Zarling et al. | 424/93.21 |
| 2002/0151059 | A1 | 10/2002 | Te Riele et al. | |

FOREIGN PATENT DOCUMENTS

| | | |
|---|---|---|
| WO | WO 95/22625 | 8/1995 |
| WO | WO 99/29837 | 6/1999 |
| WO | WO 9929837 A2 * | 6/1999 |
| WO | WO 01/04288 | 1/2001 |
| WO | WO 02/14495 A2 | 2/2002 |
| WO | WO 02/062988 | 8/2002 |

OTHER PUBLICATIONS

GenBank Accession No. AAG28905, Nov. 2, 2000.*
Davis et al. CTXphi contains a hybrid genome derived from tandemly integrated elements.☐☐ Proc Natl Acad Sci U S A. vol. 97, No. 15, pp. 8572-8577, Jul. 2000. ☐☐*
GenBank Accession No. NP_390506, Aug. 12, 2004.*
Kunst et al. The complete genome sequence of the Gram-positive bacterium Bacillus subtilis. Nature, vol. 390, pp. 249-256, Nov. 1997.*
GenBank Accession No. Al1733, Nov. 27, 2001.*
Glaser et al. Comparative genomics of Listeria species. Science, vol. 294, pp. 849-852, Oct. 2001.*
GenBank Accession No. S43799, Nov. 17, 2000.*
Alonso et al. The complete nucleotide sequence and functional organization of Bacillus subtilis bacteriophage SPP1. Gene, vol. 204, pp. 201-212, 1997.*
Yanez et al. Analysis of the complete nucleotide sequence of African swine fever virus. Virology. vol. 208, pp. 249-278, 1995.*
Scott et al. The Pendred syndrome gene encodes a chloride-iodide transport protein. Nature Genetics, vol. 21, pp. 440-443, Apr. 1999.*
Everett et al. Pendred syndrome is caused by mutations in a putative sulphate transporter gene (PDS). Nature Genetics, vol. 17, pp. 411-422, Dec. 1997.*
Yu et al. An efficient recombination system for chromosome engineering in *Escherichia coli*.☐☐Proc Natl Acad Sci U S A. vol. 97, No. 11, pp. 5978-5983, May 2000.*

(Continued)

*Primary Examiner*—Celine Qian
*Assistant Examiner*—Jennifer Dunston
(74) *Attorney, Agent, or Firm*—Klarquist Sparkman LLP

(57) ABSTRACT

Disclosed herein are methods for generating recombinant DNA molecules in cells using homologous recombination mediated by recombinases and similar proteins. The methods promote high efficiency homologous recombination in bacterial cells, and in eukaryotic cells such as mammalian cells. The methods are useful for cloning, the generation of transgenic and knockout animals, and gene replacement. The methods are also useful for subcloning large DNA fragments without the need for restriction enzymes. The methods are also useful for repairing single or multiple base mutations to wild type or creating specific mutations in the genome. Also disclosed are bacterial strains and vectors which are useful for high-efficiency homologous recombination.

36 Claims, 14 Drawing Sheets

OTHER PUBLICATIONS

Murphy et al. Use of bacteriophage lambda recombination functions to promote gene replacement in *Escherichia coli*. J Bacteriol. vol. 180, No. 8, pp. 2063-2071, Apr. 1998.*

1996/1997 NEB Catalog, New England Biolabs, Inc., pp. 186-188.*

Muyrers et al. Rapid modification of bacterial artificial chromosomes by ET-recombination.□□Nucleic Acids Res. vol. 27, No. 6, pp. 1555-1557, Mar. 1999.*

Guzman et al. Tight regulation, modulation, and high-level expression by vectors containing the arabinose PBAD promoter. J Bacteriol. vol. 177, No. 14, pp. 4121-4130, Jul. 1995.*

Hu et al. Mol Cell Biol. vol. 10, No. 12, pp. 6141-6151, Dec. 1990.*

Lowman et al. Temperature-mediated regulation and downstream inducible selection for controlling gene expression from the bacteriophage lambda pL promoter. Gene. vol. 96, No. 1, pp. 133-136, Nov. 1990.*

Leemans et al. A broad-host-range expression vector based on the pL promoter of coliphage lambda: regulated synthesis of human interleukin 2 in Erwinia and Serratia species. J Bacteriol. vol. 169, No. 5, pp. 1899-1904, May 1987.*

Verma et al. Gene therapy—promises, problems and prospects. Nature. vol. 389, No. 6648, pp. 239-242, Sep. 1997.*

Palu et al. In pursuit of new developments for gene therapy of human diseases. J Biotechnol. vol. 68, No. 1, pp. 1-13, Feb. 1999.*

Luo et al. Synthetic DNA delivery systems. Nat Biotechnol. vol. 18, No. 1, pp. 33-37, Jan. 2000.*

Edelstein et al. Gene therapy clinical trials worldwide 1989-2004-an overview. J Gene Med. vol. 6, No. 6, pp. 597-602, Jun. 2004.*

Capecchi, M., "Altering the Genome by Homologous Recombination," *Science* 244: 1288-1292, Jun. 1989.

Cho et al., "δ-Integration of endo/exo-glucanase and β-glucosidase genes into the yeast chromosomes for direct conversion of cellulose to ethanol," *Enzyme and Microbial Technology* 25: 23-30, Jul. 1999.

Copeland et al., "Recombineering: a powerful new tool for mouse functional genomics," *Nat. Rev. Genet.* 2: 769-779, 2001.

Court et al., "Genetic Engineering Using Homologous Recombination[1]," *Annu. Rev. Genet.*36: 361-388, 2002.

Cox, "Recombinational DNA Repair of Damaged Replication Forks in *Escherichia coli*," *Annu. Rev. Genet.* 35: 53-82, 2001.

Ellis et al., "High efficiency mutagenesis, repair, and engineering of chromosomal DNA using single-stranded oligonucleotides," *Proc. Natl. Acad. Sci. USA* 98: 6742-6746, 2001.

Harfe and Jinks-Robertson, "Mismatch repair proteins and mitotic genome stability," *Mut. Res.* 451: 151-167, 2000.

Higgins et al., "A Model for Replication Repair in Mammalian Cells," *J. Mol. Biol.* 101: 417-425, 1976.

Karakousis et al., "The Beta Protein of Phage λ Binds Preferentially to an Intermediate in DNA Renaturation," *J. Mol. Biol.* 276: 721-731, 1998.

Lee et al., "A highly efficient *Escherichia coli*-based chromosome engineering system adapted for recombinogenic targeting and subcloning of BAC DNA," *Genomics* 73: 56-65, 2001.

Li et al., "The Beta Protein of Phage λ Promotes Strand Exchange," *J. Mol. Biol.* 276: 733-744, 1998.

Maas et al., "Multicopy single-stranded DNA of *Escherichia coli* enhances mutation and recombination frequencies by titrating MutS protein," *Molec. Microbiol.* 19: (3) 505-509, 1996.

Minuyappa et al., "The homologous recombination system of phage λ," *J. Bio. Chem*, 261: 7472-7478, Jun. 1986.

Moerschell et al., "Transformation of yeast with synthetic oligonucleotides," *Proc. Natl. Acad. Sci. U.S.A.* 85: 524-528, 1988.

Murphy, K.C., "Use of bacteriophage λ recombination functions to promote gene replacement in *Escherichia coli*," *J. Bacteriol.* 180: 2063-2071, 1998.

Murphy et al., "PCR-mediated gene replacement in *Escherichia coli*," *Gene* 246: 321-330, 2000.

Muyrers, et al., "Point mutation of bacterial artificial chromosomes by ET recombination," *EMBO Rep.* 1: 239-243, 2000.

Muyrers et al., "RecE/RecT and Redα/Redβ initiate double-stranded break repair by specifically interacting with their respective partners," *Genes Dev.* 14: 1971-1982, 2000.

Muyrers et al., "Techniques: Recombinogenic engineering-new options for cloning and manipulating DNA," *Trends Biochem. Sci.* 26: 325-331, 2001.

Muyrers et al., "Rapid modification of bacterial artificial chromosomes by ET-recombination," *Nucleic Acids Res.* 27: 1555-1557, 1999.

Nistala and Sigmund, "A reliable and efficient method for deleting operational sequences in PACs and BACs," *Uncle. Acid. Res.* 30: 10 e 41, 2002.

Passy et al., "Rings and filaments of β protein from bacteriophage λ suggests a superfamily of recombination proteins," *Proc. Natl. Acad. Sci. U.S.A.* 96: 4279-4284, 1999.

Postow et al., "Topological challenges to DNA replication: Conformations at the fork," *Proc. Natl. Acad. Sci. USA* 98 (15): 8219-8226, 2001.

Poteete, "What makes the bacteriophage λ Red system useful for genetic engineering: molecular mechanism and biological function," *FEMS Microbiol. Lett.* 201: 9-14, 2001.

Santucci-Darmanin et al., "The DNA mismatch-repair MLH3 protein interacts with MSH4 in meiotic cells, supporting a role for this MutL homolog in mammalian meiotic recombination," *Hum. Mol. Genet.* 11: 1697-1706, 2002.

Swaminathan et al., "Rapid Engineering of Bacterial Artificial Chromosomes Using Oligonucleotides," *Genesis* 29: 14-21, 2001.

Yang et al., "Homologous recombination based modification in *Escherichia coli* and germline transmission in transgenic mice of bacterial artificial chromosome," *Nat. Biotechnol.* 15: 859-865, 1997.

Yu et al., "An efficient recombination system for chromosome engineering in *Escherichia coli*," *Proc. Natl. Acad. Sci. USA* 97: 5978-5983, 2000.

Zhang et al., "A new logic for DNA engineering using recombination in *Escherichia coli*," *Nat. Genet.* 20: 123-128, 1998.

Zhang et al., "DNA cloning by homologous recombination in *Escherichia coli*," *Nat. Biotechnol.* 18: 1314-1317, 2000.

Bilello et al., *Gene Therapy* 10:733-749, 2003.

Reuven et al., *J. Virology* 77(13):7425-7433, 2003.

Vellani et al., *J. Bacteriology* 185(8):2465-2474, 2003.

Bubeck et al., *Nucl. Acid. Res.* 21: 3601-3602, 1993.

Degyrase et al., *Gene* 170: 45-50, 1996.

Hall and Koldner, *Proc. Natl. Acad. Sci.* 91: 3205-3209, 1994.

Jasin and Schimmel, *J. Bacteriol.* 159: 783-6, 1984.

Keim and Lark, *J. Struct. Biol.* 104: 97-106, 1990.

Kusano et al., *Gene* 138: 17-25, 1994.

Nussbaum et al., *Genetics* 130: 37-49, 1992.

Oliner et al., *Nucl. Acids Res.* 21: 5192-5197, 1993.

Smith, *Ann Rev. Genet.* 21: 179-201, 1987.

Symington et al., *J. Mol. Biol.* 186: 515-525, 1985.

Zahrt et al., *Proc. Natl. Acad. Sci. USA* 94:9786-9791, 1997.

Lloyd and Low, "Homologous Recombination," www.mbio.ncsu.edu/ESU/MB758lectures04/ES119.pdf, Table of Contents © 1996.

www-db.embl-heidelberg.de/jss/servlet/de.embl.bk.wwwTools.GroupLeftEMBL.ext.html, downloaded from the internet Mar. 30, 2004.

* cited by examiner nadA gal attL int xis ea8.5 ea22 hin exo bet gam kil cIII ssb ral sieB N rexB rexA cI857 (cro-attR-bioA)
                                                                              P_L                      P_R   Δ

A

B

Recombination with 5'-overhangs
The Effect of Overlap Length

US 7,144,734 B2

ENHANCED HOMOLOGOUS RECOMBINATION MEDIATED BY LAMBDA RECOMBINATION PROTEINS

CROSS-REFERENCE TO RELATED APPLICATIONS

This application is a continuation-in-part of International Application No. PCT/US01/25507, filed Aug. 14, 2001, which claims the benefit of U.S. Provisional Application No. 60/225,164, filed Aug. 14, 2000, and claims the benefit of U.S. Provisional Application No. 60/271,632, filed Feb. 26, 2001, which are all incorporated by reference herein in their entirety.

FIELD

The present disclosure relates to methods to enhance homologous recombination in bacteria and eukaryotic cells using recombination proteins, such as those derived from bacteriophage lambda. It also relates to methods for modifying genomic DNA in bacterial artificial chromosomes (BACs) and to subcloning of genomic DNA from BACs into multicopy plasmids.

BACKGROUND OF THE INVENTION

Concerted use of restriction endonucleases and DNA ligases allows in vitro recombination of DNA sequences. The recombinant DNA generated by restriction and ligation may be amplified in an appropriate microorganism such as *E. coli*, and used for diverse purposes including gene therapy. However, the restriction-ligation approach has two practical limitations: first, DNA molecules can be precisely combined only if convenient restriction sites are available; second, because useful restriction sites often repeat in a long stretch of DNA, the size of DNA fragments that can be manipulated are limited, usually to less than about 25 kilobases.

Homologous recombination, generally defined as an exchange between homologous segments anywhere along a length of two DNA molecules, provides an alternative method for engineering DNA. In generating recombinant DNA with homologous recombination, a microorganism such as *E. coli*, or a eukaryotic cell such as a yeast or vertebrate cell, is transformed with exogenous DNA. The center of the exogenous DNA contains the desired transgene, whereas each flank contains a segment of homology with the cell's DNA. The exogenous DNA is introduced into the cell with standard techniques such as electroporation or calcium phosphate-mediated transfection, and recombines into the cell's DNA, for example with the assistance of recombination-promoting proteins in the cell.

In generating recombinant DNA by homologous recombination, it is often advantageous to work with short linear segments of DNA. For example, a mutation may be introduced into a linear segment of DNA using polymerase chain reaction (PCR) techniques. Under proper circumstances, the mutation may then be introduced into cellular DNA by homologous recombination. Such short linear DNA segments can transform yeast, but subsequent manipulation of recombinant DNA in yeast is laborious. It is generally easier to work in bacteria, but linear DNA fragments do not readily transform bacteria (due in part to degradation by bacterial exonucleases). Accordingly, recombinants are rare, require special poorly-growing strains (such as RecBCD-mutant strains) and generally require thousands of base pairs of homology. Thus, improved methods of promoting homologous recombination in bacteria are needed.

In eukaryotic cells, targeted homologous recombination provides a basis for targeting and altering essentially any desired sequence in a duplex DNA molecule, such as targeting a DNA sequence in a chromosome for replacement by another sequence. The approach may be useful for treating human genetic diseases.

Homologous recombination has been used to create knock-out mutants and transgenic animals, and thereby has played a critically important role in understanding gene function. Transgenic animals are organisms that contain stably integrated copies of genes or gene constructs derived from another species in the chromosome of the transgenic animal. These animals can be generated by introducing cloned DNA constructs of the foreign genes into totipotent cells by a variety of methods, including homologous recombination.

Currently, methods for producing transgenics have been performed on totipotent embryonic stem cells (ES) and with fertilized zygotes. ES cells have an advantage in that large numbers of cells can be manipulated in vitro before they are used to generate transgenics. Alternatively, DNA can also be introduced into fertilized oocytes by micro-injection into pronuclei, or injection into the germline of organisms including *C. elegans* or *Drosophila* species.

Several methods have been developed to detect and/or select for targeted site-specific recombinants between vector DNA and the target homologous chromosomal sequence (Capecchi, *Science* 244:1288, 1989). Cells that exhibit a specific phenotype after recombination, such as occurs with alteration of the hypoxanthine phosphoribosyl transferase (hprt) gene, can be obtained by direct selection on the appropriate growth medium. Alternatively, a selectable marker such as neomycin resistance can be incorporated into a vector under promoter control, and successful transfection can be scored by selecting G418-resistant cells (Joyner et al., *Nature* 338:153, 1989). Numerous other selection procedures have been described (Jasin and Berg, *Genes and Development* 2:1353, 1988; Doetschman et al., *Proc. Natl. Acad. Sci. U.S.A.* 85:8583, 1988; Dorini et al., *Science* 243:1357, 1989; Itzhaki and Porter, *Nucl. Acids Res.* 19:3835, 1991). Unfortunately, exogenous sequences transferred into eukaryotic cells undergo homologous recombination only at very low frequencies, even when very long homology regions are present (Koller et al., *Proc. Natl. Acad. Sci. U.S.A.*, 88:10730, 1991, and Snouwaert et al., *Science* 257:1083, 1992). Thus, large numbers of cells must be transfected, selected, and screened in order to generate a correctly targeted homologous recombinant.

SUMMARY OF THE DISCLOSURE

The present disclosure provides methods for cloning DNA molecules in cells having DNA encoding lambda recombinases operably linked to a de-repressible promoter, for example the lambda pL promoter. The pL promoter is activated, for example by temperature shift, thereby leading to expression of lambda recombinases. The lambda recombinases promote homologous recombination between nucleic acids in the cell. The nucleic acids undergoing recombination may be intrachromosomal, or may be extrachromosomal, for example in a bacterial artificial chromosome.

The present disclosure also provides methods for inducing homologous recombination using single-stranded DNA molecules, by introducing into the cell DNA capable of undergoing homologous recombination, and a single-stranded DNA binding polypeptide capable of promoting homologous recombination. Such single-stranded DNA binding polypeptides include lambda Beta, RecT, P22 Erf, and Rad52, as well as functional fragments and variants of single-stranded DNA binding polypeptides.

The present disclosure also provides bacterial cells that promote efficient homologous recombination. These bacterial cells contain one or more genes or promoters from a defective lambda prophage within the bacterial chromosome.

The disclosure also provides methods for altering eukaryotic genes by expressing recombinases operably linked to a de-repressible promoter in bacterial cells. Eukaryotic genes thus modified can be used to modify eukaryotic cells, for example to generate transgenic or knockout animals.

BRIEF DESCRIPTION OF THE FIGURES

FIG. 8A shows as short thick black arrows the location of the 5' homologies on the amplification primers used to amplify pBR322 for subcloning by gap repair. Each primer also contains 20 nt segments at its 3' end to prime pBR322. NotI and SalI cleavage sites were included in these primers to facilitate release of the subcloned fragments from the plasmid backbone. The location of SpeI restriction sites near Eno2 is also shown ("S"). SpeI restriction sites are not present on the linear amplified pBR322 vector. FIG. 8B shows an intermediate step in gap repair, pairing between a typical amplified pBR322 targeting cassette and the modified Eno2 BAC. Ap, amp resistance gene; ORI, origin of replication.

FIG. 16A is a set of schematic diagrams of the 11.0 kb genomic DNA fragment containing Evi9 exon 4 was subcloned from BAC-A12 using gap repair. EcoRV digestion of the gap-repaired plasmid generates 7.6 kb and 8.8 kb fragments. The 7.6 kb fragment contains Evi9 exon 4 sequences, while the 8.8 kb fragment, common to all lanes contains plasmid sequences and Evi9 sequences located upstream of exon 4. The floxed Neo cassette of PL452 was targeted upstream of Evi9 exon 4. In the targeted plasmid, the 7.6 kb EcoRV fragment increases in size to 9.6 kb due to the addition of the floxed Neo cassette. Excision of the floxed Neo cassette leaves behind a single LoxP (black arrow) at the targeted locus, and the normal EcoRV digestion pattern is restored. Next, the PL451 selection cassette containing the Neo gene flanked by frt sites (grey arrow) and a downstream LoxP, was targeted downstream of Evi9 exon 4. The PL451 selection cassette contains an EcoRV site, which results in the production of 6.5 kb and 3.1 kb fragments following EcoRV digestion. This is the Evi9 cko-targeting vector. To test the functionality of the frt sites in the cko-targeting vector, the PL451 selection cassette was excised from the cko-targeting vector by FLP recombinase following electroporation into EL250 cells. This reduces the size of the 6.5 kb EcoRV fragment to 4.5 kb. Finally, electroporation of the cko-targeting cassette into EL350 cells expressing Cre recombinase excises the entire DNA between the two-LoxP sites, creating a 4.6 kb EcoRV fragment. FIG. 16B is a digital image of EcoRV-digestion patterns of the plasmids at every stage of the targeting vector construction.

FIG. 17A is a schematic diagram of homologous recombination between the Evi9 cko-targeting vector and the Evi9 genomic locus. Correctly targeted ES cells (cko allele) have a 5.5 kb BglII band, in addition to an 18.1 kb wild type band, following hybridization with the 5' probe. These cko clones also have a 6.3 kb EcoRV-targeted band, as well as a 7.3 kb wild type band, following hybridization with the 3' probe. FIG. 17B is a digital image of a Southern blot analysis of the ES cell clones. The 5' probe was used in the left panel and a 3' probe was used in the right panel. wt: wild type ES clones, cko: conditional knockout ES clones.

DETAILED DESCRIPTION OF SPECIFIC EMBODIMENTS

Figures 1, 3:
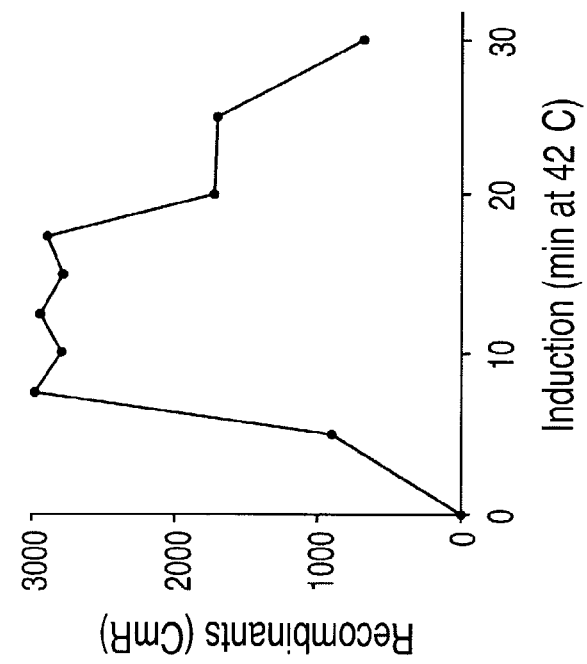
FIG. 1 is a linear depiction of the defective lambda prophage as it is integrated on the $E.$ $coli$ chromosome. Prophage genes are indicated by the solid line, and $E.$ $coli$ genes by broken lines. The coding regions for the lambda recombination genes exo, bet and gam are approximately in the center of the defective prophage. Lambda genes cro through attR, deleted from the defective prophage, are enclosed within parentheses together with the $E.$ $coli$ bioA gene to indicate their deletion.
FIG. 3 is a graph that shows the effect of induction time of the lambda proteins Beta, Exo, and Gam on recombination efficiency. A linear chloramphenicol resistance cassette was used to target prophage genes, and was electroporated into cells after the cells had been heated to 42° C. for the time indicated. Time of induction (temperature shift to 42° C.) is plotted on the x-axis, against number of chloramphenicol-resistant recombinants obtained on the y-axis.

There exists a need in the art for methods of precisely and efficiently altering predetermined endogenous genetic sequences by homologous recombination in vivo. There independently exists a need in the art for high-efficiency gene targeting, so as to avoid complex in vitro or in vivo selection protocols. Methods are disclosed herein for cloning DNA molecules in cells using homologous recombination mediated by lambda recombinases and similar proteins.

One such method uses a cell having DNA encoding functional Beta and optionally Exo, and Gam, or functional fragments or variants thereof, operably linked to the a de-repressible promoter (such as, but not limited to, the pL promoter). De-repression of the de-repressible promoter (e.g. the induction of transcription from the pL promoter by inactivation of cI) induces expression of exo, bet and gam and in some embodiments may be selectively activated for this purpose. A nucleic acid (such as a polynucleotide which is homologous to a target DNA sequence) capable of undergoing homologous recombination is introduced into the cell, and cells in which homologous recombination has occurred are either selected or found by direct screening of cells. In particular embodiments, the nucleic acid introduced into the cell may be double strand DNA, or DNA with 5' overhangs.

In additional particular embodiments, at least 1 in 5000 cells contain DNA in which homologous recombination has occurred. In further embodiments, at least 1 in 1,000 cells, or 1 in 500 cells, 1 in 100 cells, or 1 in 20 cells contain DNA in which homologous recombination has occurred.

The cell may be a eukaryotic cell, or a prokaryotic cell, such as a bacterial cell, for example an *E. coli* strain. The DNA encoding the lambda recombination proteins and pL promoter may be intrachromosomal or extrachromosomal. Similarly, the target DNA sequence may be intrachromosomal or extrachromosomal; for example, the target DNA sequence may be found in a chromosome of the cell or a plasmid (including derivatives of colE1, pSC101, p15A and shuttle vectors that replicate in both bacteria and eucaryotic cells), bacterial artificial chromosome, P1 artificial chromosome, yeast artificial chromosome, cosmid or the like.

In additional particular embodiments, the nucleic acid introduced into the cell may be double-stranded DNA or DNA with a 5' overhang, and may include a positive or negative selectable marker. The introduced nucleic acid may alter the function of a nucleic acid sequence such as a gene in the cell, or add a gene to the DNA of the cell. The cell may be treated to enhance macromolecular uptake, for example using electroporation, calcium phosphate-DNA coprecipitation, liposome mediated transfer, or other suitable methods. In other particular embodiments, the method may produce homologous recombination that alters the function of a gene in the cell, or adds a gene to the cell.

In further particular embodiments, the cell may be treated to enhance macromolecular uptake, for example with electroporation, calcium phosphate-DNA co-precipitation, DEAE-dextran-mediated transfection, polybrene-mediated transfection, microinjection, liposome fusion, lipofection, protoplast fusion, inactivated adenovirus-mediated transfer, HVJ-liposome mediated transfer, and biolistics.

Another such method that meets one or more of the above-mentioned needs includes methods that introduce into the cell DNA capable of undergoing homologous recombination and a ssDNA binding polypeptide capable of promoting homologous recombination. In particular embodiments, the DNA is ssDNA or DNA having 3' overhangs.

The single stranded DNA (ssDNA) binding polypeptide is a type of DNA binding polypeptide which mediates double strand break repair homologous recombination by binding to ssDNA or a 3' overhang in dsDNA and promoting recombination. It promotes recombination by annealing the bound ssDNA to its complement in the cell. Examples of such ssDNA binding polypeptide include lambda Beta, *E. coli* RecT, Erf of bacteriophage P22, and Rad52. The ssDNA binding polypeptide may be introduced as a nucleic acid. For example, a nucleic acid that expresses the ssDNA binding polypeptide is introduced into a cell, such as a eukaryotic cell. Expression of the ssDNA binding polypeptide from a nucleic acid may be induced, for example, by activation of an inducible promoter. In particular embodiments, the nucleic acid may further include lambda exo and gam, and the inducible promoter may be the lambda pL promoter. In other embodiments, the ssDNA binding polypeptide is introduced into the cell as a polypeptide.

The cell used in methods disclosed herein may be a bacterial cell such as an *E. coli* strain, or a eukaryotic cell such as a mammalian cell, a stem cell, or virtually any other eukaryotic cell type. The DNA used in the method may be a single oligonucleotide sequence, or may be two or more overlapping sequences, for example with more than 10, or more than 20 base pairs of complementary overlap at either their 5' or 3' termini (in specific examples of the 5' case, the nucleic acid includes exo and bet nucleic acid sequences). The DNA may comprise a selectable marker, and homologous recombination with the ssDNA may confer a selectable phenotype upon the cell. In particular embodiments, the cell may be treated to enhance macromolecular uptake, such as with electroporation, calcium phosphate-DNA coprecipitation, liposome mediated transfer, or other suitable methods. The effect of homologous recombination may be to alter the function of a gene in the cell, or add a gene to the cell.

In particular examples, the ssDNA is used in an amount of about 0.01 µM to about 10 mM; or from about 0.1 µM to about 1 mM; or from about 1 µM to about 100 µM. In other examples, the ssDNA binding polypeptide is used in an amount of 0.001 µM to about 0.01 µM, or from about 0.01 µM to about 10 mM; or from about 0.1 µM to about 1 mM; or from about 1 µM to about 100 µM.

Also disclosed are bacterial cells that may be useful in practicing the disclosed methods. These include bacterial cells harboring a defective lambda prophage of genotype λcI857 Δ(cro-bioA). In particular examples, the bacterial cells may have a selectable marker, such as an antibiotic resistance marker, upstream of the cI857 gene. In some particular examples, the disclosed bacterial cells include an inducible promoter upstream of the cI857 gene, which may be operably connected to a gene encoding a recombinase, such as flp, flpe, or Cre, or a gene encoding functional fragments or variants of these recombinases. In other particular examples, the bacterial cells may contain a bacterial artificial chromosome, which may have a selectable marker, LoxP, and/or frt sites. In particular embodiments, the selectable marker on the bacterial artificial chromosome is excisable by a recombinase. In other particular examples, the bacterial artificial chromosome may have at least one exon or at least one intron of a mammalian gene.

The disclosure also includes methods of altering eukaryotic genes by expressing in a bacterial cell an intrachromosomal gene encoding a recombinase operably linked to a pL promoter. The bacterial cell also includes an extrachromosomal eukaryotic gene or gene fragment (having at least one intron or at least one exon of a eukaryotic gene). A nucleic acid capable of undergoing homologous recombination with the eukaryotic gene is introduced into the bacterial cell, and the nucleic acid undergoes homologous recombination with the eukaryotic gene or gene fragment. In a particular embodiment, the nucleic acid undergoes homologous recombination with a targeting frequency of at least about 1 in 1,000.

In one embodiment, the expressed recombinase is a double strand break repair recombinase, such as lambda Beta or other single-stranded DNA binding protein; lambda Exo, or lambda Gam. In another embodiment, the extrachromosomal eukaryotic gene or gene fragment may be located on a bacterial artificial chromosome, yeast artificial chromosome, P1 artificial chromosome, plasmid or cosmid. In yet another embodiment, the eukaryotic gene or gene fragment is derived from a mammalian organism, such as a mouse or human.

In several additional embodiments, the nucleic acid undergoing homologous recombination may encode a recombinase, functional fragments or variants of a recombinase, or an epitope tag.

Also disclosed are methods of altering intrachromosomal DNA of a eukaryotic cell. In these methods, an altered eukaryotic gene or gene fragment is introduced into the eukaryotic cell. The introduced eukaryotic gene or gene fragment has been altered by homologous recombination using the methods of this disclosure.

For example, extrachromosomal DNA including the eukaryotic gene or gene fragment is introduced into a bacterial cell having an intrachromosomal gene encoding a recombinase operably linked to a de-repressible promoter. The bacterial cell is then induced to express the recombinase. A nucleic acid molecule capable of undergoing homologous recombination with the eukaryotic gene or gene fragment is introduced into the bacterial cell. The eukaryotic gene or gene fragment undergoes homologous recombination with the nucleic acid, and altered eukaryotic gene or gene fragment may then be isolated and introduced into a eukaryotic cell.

In one embodiment, the eukaryotic gene or gene fragment introduced into the eukaryotic cell is located on a bacterial artificial chromosome. The eukaryotic gene or gene fragment is capable of undergoing homologous recombination with a target gene in the cell, thereby altering the nucleic acid sequence of the eukaryotic cell's intrachromosomal DNA. In specific, non-limiting examples, the eukaryotic cell is a mammalian cell, an embryonic stem cell, or a zygote.

Also disclosed are mutant mammals which have had one or more of their genes altered by homologous recombination with a bacterial artificial chromosome carrying a eukaryotic gene or gene fragment that has been altered by the disclosed methods. The gene alteration can introduce a recombinase into the mutant mammal, such as a site-specific recombinase.

A mobilizable lambda DNA is also disclosed herein that is isolated as a mini-lambda prophage. The mobilizable lambda DNA can be transformed into any bacterial strain of interest. The lambda DNA integrates into the bacterial chromosome to generate a defective prophage that expresses the recombinase.

The present disclosures provide methods of enhancing the efficiency of homologous recombination. The disclosures will be better understood by reference to the following explanation of terms used and detailed description of methods for carrying out the invention.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

I. TERMS

3' overhang: Two nucleic acid sequences which when annealed are partially double-stranded and partially single-stranded. The single-stranded end or ends extend away from the double-stranded segment in a 5' to 3' direction.

5' overhang: Two nucleic acid sequences which when annealed are partially double-stranded and partially single-stranded. The single-stranded end or ends extend away from the double-stranded segment in a 3' to 5' direction.

Antibiotic Resistance Cassette: A nucleic acid sequence encoding a selectable marker which confers resistance to that antibiotic in a host cell in which the nucleic acid is translated. Examples of antibiotic resistance cassettes include, but are not limited to: kanamycin, ampicillin, tetracycline, chloramphenicol, neomycin, hygromycin, and zeocin.

Arabinose: A simple 5-carbon sugar metabolized by *E. coli*. In one embodiment, it is used as a chemical to inactivate repression and to induce and activate expression from the promoter pBAD.

Attachment Site (att): A site specific site for recombination that occurs on either a phage or a chromosome. An attachment site on lambda is termed "attP", while an attachment site of a bacterial chromosome is "attB." Integrase mediated recombination of an attP site with an attB site leads to integration of the λ prophage in the bacterial chromosome.

Bacterial artificial chromosome (BAC): Bacterial artificial chromosomes (BACs) have been constructed to allow the cloning of large DNA fragments in *E. coli* as described in O'Conner et al., *Science* 244:1307–12, 1989; Shizuya et al., *Proc. Natl. Acad. Sci. U.S.A.* 89:8794–7, 1992; Hosoda et al., *Nucleic Acids Res.* 18:3863–9, 1990; and Ausubel et al., eds., *Current Protocols In Molecular Biology*, John Wiley & Sons (c) 1998 (hereinafter Ausubel et al., herein incorporated in its entirety). This system is capable of stably propagating mammalian DNA over 300 kb. In one embodiment, a BAC carries the F replication and partitioning systems that ensure low copy number and faithful segregation of plasmid DNA to daughter cells. Large genomic fragments can be cloned into F-type plasmids, making them of use in constructing genomic libraries.

Beta: The 28 kDa lambda Beta ssDNA binding polypeptide (and nucleic acid encoding lambda beta) involved in double strand break repair homologous recombination. DNA encoding Beta (bet) and polypeptide chains having lambda Beta activity are also referred to herein as bet. See Examples 1 and 14 and references therein for further information. The lambda Beta protein binds to single-stranded DNA and promotes renaturation of complementary single strand regions of DNA (see also Karakousis et al., *J. Mol. Biol.* 276:721–733, 1998; Li et al., *J. Mol. Biol.* 276:721–733, 1998; Passy et al., *PNAS* 96:4279–4284, 1999).

Functional fragments and variants of Beta include those variants that maintain their ability to bind to ssDNA and mediate the recombination function of lambda Beta as described herein, and in the publications referenced herein. It is recognized that the gene encoding Beta may be considerably mutated without materially altering the ssDNA binding function or homologous recombination function of lambda Beta. First, the genetic code is well-known to be degenerate, and thus different codons encode the same amino acids. Second, even where an amino acid mutation is introduced, the mutation may be conservative and have no material impact on the essential functions of lambda Beta. See Stryer, *Biochemistry* 3rd Ed., (c) 1988. Third, part of the lambda Beta polypeptide chain may be deleted without impairing or eliminating its ssDNA binding protein function, or its recombination function. Fourth, insertions or additions may be made in the lambda Beta polypeptide chain—for example, adding epitope tags—without impairing or eliminating its essential functions (see Ausubel et al., 1997, supra).

Biolistics: Insertion of DNA into cells using DNA-coated micro-projectiles. Also known as particle bombardment or microparticle bombardment. The approach is further described and defined in U.S. Pat. No. 4,945,050, which is herein incorporated by reference.

cDNA (complementary DNA): A piece of DNA lacking internal, non-coding segments (introns) and regulatory sequences that determine transcription. cDNA may be synthesized in the laboratory by reverse transcription from messenger RNA extracted from cells.

Cosmid: Artificially constructed cloning vector containing the cos gene of phage lambda. Cosmids can be packaged in lambda phage particles for infection into *E. coli*; this permits cloning of larger DNA fragments (up to 45 kb) than can be introduced into bacterial hosts in plasmid vectors.

Cre: The Cre recombinase is a site-specific recombinase. It recognizes and binds to specific sites called LoxP. Two LoxP sites recombine at nearly 100% efficiency in the presence of Cre, thus, permitting DNA cloned between two such sites to be efficiently removed by the Cre-mediated recombination.

De-repressible Promoter: When a repressor is bound to a de-repressible promoter transcription is substantially decreased as compared to transcription from the de-repressible promoter in the absence of repressor. By regulating the binding of the repressor, such as by changing the environment, the repressor is released from the de-repressible promoter, and transcription increases. As used herein, a de-repressible promoter does not require an activator for transcription. One specific, non-limiting example is the pL promoter, which is regulated by the repressor cI, but is not activated by an activator. The arabinose promoter is not a simple de-repressible promoter as arabinose inactivates the repressor AraC and converts it to an activator.

In one embodiment, the de-repressible promoter is a temperature sensitive de-repressible promoter. For example, by increasing the temperature, the repressor is released from the promoter, or can no longer bind to the promoter with a high affinity, and transcription is increased from the promoter. One specific, non-limiting example is the induction of pL promoter activity by increasing the temperature of the cell. Increased temperature inactivates the temperature-sensitive repressor cI, allowing genes that are operably linked to the pL promoter to be expressed at increased levels. One of skill in the art can readily identify a repressible promoter.

In one embodiment, a de-repressible promoter is auto-regulated. One specific, non-limiting example of an auto-regulated de-repressible promoter is pL. If only one copy of a gene encoding cI is present, yet many copies of the pL promoter are present, expression of cI is upregulated such that transcription is blocked from any of the pL promoters.

Double-strand break repair recombination: A type of homologous recombination exemplified by the lambda recombination proteins Exo, Beta and Gam, and shared by numerous other recombinase systems. A double strand break is the initiation point for concerted action of recombination proteins. Typically, an exonuclease degrades processively from the 5' ends of these break sites, and ssDNA binding polypeptide binds to the remaining 3' single strand tail, protecting and preparing the recessed DNA for homologous strand invasion (Szostak et al., *Cell* 33:25–35, 1983; Little, *J. Biol. Chem.* 242:679–686, 1967; Carter et al., *J. Biol. Chem.* 246:2502–2512, 1971; Lindahl et al., *Science* 286: 1897–1905, 1999). Examples of ssDNA binding polypeptides which bind to either ssDNA and/or dsDNA with 3' overhangs and promote double-strand break repair recombination include lambda Beta, RecT of *E. coli*, Erf of phage p22, and Rad52 in various eukaryotic cells including yeast and mammalian cells.

Electrocompetent: Cells capable of macromolecular uptake upon treatment with electroporation.

Electroporation: A method of inducing or allowing a cell to take up macromolecules by applying electric fields to reversibly permeabilize the cell walls. Various methods and apparatuses used are further defined and described in: U.S. Pat. Nos. 4,695,547; 4,764,473; 4,882,28; 4,946,793; 4,906, 576; 4,923,814; and 4,849,089, all of which are herein incorporated by reference.

Eukaryotic cell: A cell having an organized nucleus bounded by a nuclear membrane. These include lower organisms such as yeasts, slime molds, and the like, as well as cells from multicellular organisms such as invertebrates, vertebrates, and mammals. They include a variety of tissue types, such as, but not limited to, endothelial cell, smooth muscle cell, epithelial cell, hepatocyte, cells of neural crest origin, tumor cell, hematopoetic cell, immunologic cell, T cell, B cell, monocyte, macrophage, dendritic cell, fibroblast, keratinocyte, neuronal cell, glial cell, adipocyte, myoblast, myocyte, chondroblast, chondrocyte, osteoblast, osteocyte, osteoclast, secretory cell, endocrine cell, oocyte, and spermatocyte. These cell types are described in standard histology texts, such as McCormack, *Introduction to Histology*, (c) 1984 by J. P. Lippincott Co.; Wheater et al., eds., *Functional Histology*, 2nd Ed., (c) 1987 by Churchill Livingstone; Fawcett et al., eds., Bloom and Fawcett: *A Textbook of Histology*, (c) 1984 by William and Wilkins, all of which are incorporated by reference in their entirety. In one specific, non-limiting example, a eukaryotic cell is a stem cell, such as an embryonic stem cell.

Exo: The exonuclease of lambda (and the nucleic acid encoding the exonuclease protein) involved in double strand break repair homologous recombination. See Example 1 and references therein for further description.

Exogenous: The term "exogenous" as used herein with reference to nucleic acid and a particular cell refers to any nucleic acid that does not originate from that particular cell as found in nature. Thus, a non-naturally-occurring nucleic acid is considered to be exogenous to a cell once introduced into the cell. Nucleic acid that is naturally-occurring also can be exogenous to a particular cell. For example, an entire chromosome isolated from a cell of subject X is an exogenous nucleic acid with respect to a cell of subject Y once that chromosome is introduced into Y's cell.

Extrachromosomal: Not incorporated into the chromosome or chromosomes of a cell. In the context of nucleic acids, extrachromosomal indicates an DNA oligonucleotide that is not covalently incorporated into the chromosome or chromosomes of a cell. Intrachromosomal refers to material such as an oligonucleotide that is incorporated into the chromosome or chromosomes of a cell, such as a DNA oligonucleotide covalently incorporated into the chromosomal DNA of a cell.

Flanking: A nucleic acid sequence located both 5' and 3' of a nucleic acid sequence of interest. Thus, in the sequence "A-B-A", nucleic acid sequence "A" flanks nucleic acid sequence "B". In one specific, non-limiting example, nucleic acid sequence "A" is located immediately adjacent to nucleic acid "B." In another specific, non-limiting example, an linker sequence of not more than 500 nucleotides is between each copy of "A" and "B," such as a linker sequences of about 200, about 100, about 50, or about 10 nucleotides in length. Nucleotide sequences "A" and "B" can be of any length.

Flanked nucleic acid or flanked transgene: A nucleic acid sequence flanked at a 5'- and 3'-portion by recombining sites. In one embodiment, the nucleic acid is a transgene. In another embodiment, the nucleic acid is an antibiotic resistance cassette. In a further embodiment, the nucleic acid is a BAC DNA, or a gene on a BAC DNA. In one specific, non-limiting example, the recombining site is Lox.

fLOXed nucleic acid or transgene: A nucleic acid sequence, such as a transgene, which is flanked at a 5'- and 3'-portion by Lox recombining sites.

Gam: A lambda protein (and nucleic acid encoding Gam) involved in double strand break repair homologous recombination. It is believe to inhibit cellular nuclease activity such as that encoded by the recBCD and sbcC system of *E. coli*. See Examples 1, 7 and 14 and references therein for further description. Gam function, when expressed in the cell, is extremely toxic to the cell, and prevents growth. For this reason tight controls over its expression are always required. As described herein, pL and cI 857 are able to regulate Gam expression Functional fragments and variants of Exo and Gam: As discussed for Beta (see "Functional fragments And Variants Of Beta"), it is recognized that genes encoding Exo or Gam may be considerably mutated without materially altering their function, because of genetic code degeneracy, conservative amino acid substitutions, noncritical deletions or insertions, etc. Unless the context makes otherwise clear, the term lambda Exo, Exo, or lambda exonuclease are all intended to include the native lambda exonuclease, and all fragments and variants of lambda exonuclease.

Gene: A nucleic acid encoding a protein product. In a specific non-limiting example, a gene includes at least one expression control sequence, such as a promoter, enhancer or a repressor. In another specific, non-limiting example, a gene includes at least one intron and at least on exon.

Homologous arm: Nucleotides at or near 5' or 3' end of a polynucleotide which are identical or similar in sequence to the target nucleic acid in a cell, and capable of mediating homologous recombination with the target nucleic acid.

Homologous arms are also referred to as homology arms. In one embodiment, a homology arm includes at least 20 bases of a sequence homologous to a nucleic acid of interest. In another embodiment, the homology arm includes at least 30 base pairs of a sequence homologous to a nucleic acid of interest. In yet another embodiment, a homology arm includes at least 40 base pairs of a sequence homologous to a nucleic acid of interest. In a further embodiment, a homology arm includes from about 50 to about 100 base pairs of a sequence homologous to a nucleic acid of interest.

Homologous recombination: An exchange of homologous polynucleotide segments anywhere along a length of two nucleic acid molecules. In one embodiment, two homologous sequences are 100% identical. In another embodiment, two homologous sequences are sufficiently identical such that they can undergo homologous recombination. Specific, non-limiting examples of homologous sequences are nucleic acid sequences that are at least 95% identical, such as about 99% identical, about 98% identical, about 97% identical, or about 96% identical.

Host cell: A cell that is used in lab techniques such as DNA cloning to receive exogenous nucleic acid molecules. In one embodiment a host cell is used to maintain or allow the reproduction of a vector, or to facilitate the manipulation of nucleic acid molecules in vitro. A host cell can be a prokaryotic or a eukaryotic cell.

HVJ-mediated gene transfer: A method of macromolecular transfer into cells using inactivated hemagglutinating virus of Japan and liposomes, as described in Morishita et al., *J. Clin. Invest.* 91:2580–2585, 1993; Morishita et al., *J. Clin. Invest.* 94:978–984, 1994; which are herein incorporated by reference.

Inducible promoter: A promoter whose activity may be increased (or that may be de-repressed) by some change in the environment of the cell. Examples of inducible promoters abound in nature, and a broad range of environmental or hormonal changes may activate or repress them.

Intron: An intragenic nucleic acid sequence in eukaryotes that is not expressed in a mature RNA molecule. Introns of the present disclosure include full-length intron sequences, or a portion thereof, such as a part of a full-length intron sequence.

Isolated: An "isolated" biological component (such as a nucleic acid or protein) has been substantially separated or purified away from other biological components in the cell of the organism in which the component naturally occurs, i.e., other chromosomal and extra-chromosomal DNA and RNA, and proteins. Thus, nucleic acids and proteins that have been "isolated" include nucleic acids and proteins purified by standard purification methods. The term also embraces nucleic acids and proteins prepared by recombinant expression in a host cell as well as chemically synthesized nucleic acids.

Knockout: Inactivation of a gene such that a functional protein product cannot be produced. A conditional knockout is a gene that is inactivated under specific conditions, such as a gene that is inactivated in a tissue-specific or a temporal-specific pattern. A conditional knockout vector is a vector including a gene that can be inactivated under specific conditions. A conditional knockout transgenic animal is a transgenic animal including a gene that can be inactivated in a tissue-specific or a temporal-specific manner.

Linear plasmid vector: A DNA sequence (1) containing a bacterial plasmid origin of replication, (2) having a free 5' and 3' end, and (3) capable of circularizing and replicating as a bacterial plasmid by joining its free 5' and 3' ends. Examples of linear plasmid vectors include the linearized pBluescript vector and linearized pBR322 vectors described herein.

Lipofection: The process of macromolecular transfer into cells using liposomes. See U.S. Pat. No. 5,651,981, which is herein incorporated by reference.

Lox: A target recombining site sequence recognized by the bacterial Cre recombinase (Cre). Specific, non-limiting examples include, but are not limited to, the sequence listed as GenBank Accession No. M10494.1; LoxP (GenBank Accession No. U51223); Lox 511 (Bethke and Sauer, *Nuc. Acid. Res.* 25:282–34, 1997); ψLOXh7q21 (Thyagarajan et al., *Gene* 244:47–54, 2000), ψCoreh7q21 (Thyagarajan et al., *Gene* 244:47–54, 2000) as well as the Lox sites disclosed in Table 1 of Thyagarajan et al. (*Gene* 244:47–54, 2000, herein incorporated by reference). In one example, LoxP sites are defined by the sequence ATAACTTCGTATAATG-TATGCTATACGAAGTTAT (SEQ ID NO: 51).

A "minimal" Lox sequence is the minimal sequence recognized by Cre. In one emb example, minimal Lox sequence is as described in Hoekstra et al., *Proc. Nat. Acad. Sci. U.S.A.* 88:5457–61, 1991. In another example, 5' and 3' Lox sequences are identical.

As used herein, Lox sequences are located upstream and downstream (5' and 3', respectively) to a nucleic acid sequence, for example a nucleic acid sequence encoding a transgene, such as a transgene encoding a therapeutic polypeptide, or a marker polypeptide.

Mini lambda: A derivative of lambda (λ) wherein most of the viral lytic genes, including those required for replication and lysis, are deleted. A mini-lambda maintains the red functions (Beta, Exo, and Gam) for homologous recombination and maintains the integration/excision functions (e.g. att, integrase (int). and excisionase (xis)) to insert and excise its DNA from the chromosome.

Nucleic acid: A deoxyribonucleotide or ribonucleotide polymer in either single or double stranded form, including known analogs of natural nucleotides unless otherwise indicated.

Oligonucleotide (oligo): A single-stranded nucleic acid ranging in length from 2 to about 500 bases, for example, polynucleotides that contain at least 20 or 40 nucleotides (nt). Oligonucleotides are often synthetic but can also be produced from naturally occurring polynucleotides.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Phagemid artificial chromosome: Also referred to as P1 artificial chromosome. A type of artificial chromosome allowing for stable cloning of very large DNA fragments. Phagemid artifical chromosomes are further described in Shepherd, et al., *Proc. Natl. Acad. Sci. U.S.A.* 92:2629, 1994; Iannou et al., *Nature Genetics* 6:84–89, 1994.

Phage-based recombination systems: Bacteria such as *E. coli* encode their own homologous recombination systems, which are used in repair of DNA damage and to maintain a functional chromosome. The viruses or phages that inhabit bacteria often carry their own recombination functions. Phage λ carries the Red recombination system. These phage systems can work with the bacterial recombination functions or independently of them.

pL promoter: The major leftward promoter of bacteriophage lambda. Once the lambda DNA is incorporated into the bacterial chromosome, transcription from this promoter is substantially repressed by the cI repressor. Upon inactivation of the cI repressor, for example by heat shock of a temperature sensitive mutant, transcription from the pL promoter is activated, leading to expression of lambda genes. See FIG. 1; Sambrook et al., Bacteriophage Lambda Vectors, Chapter 2 in *Molecular Cloning: a Laboratory Manual,* 2nd Ed., (c) 1989 (hereinafter Sambrook et al.); Stryer, Control of Gene Expression in Procaryotes, Chapter 32 in *Biochemistry* 3rd Ed., pp. 799–823, (c) 1988 (hereinafter Stryer); and Court and Oppenheim, pp. 251–277 in Hendrix et al. eds., *Lambda II,* Cold Spring Harbor Lab Press, (c) 1983 (hereinafter Court and Oppenheim).

Plasmid: Autonomously replicating, extrachromosomal DNA molecules, distinct from the normal bacterial genome and nonessential for bacterial cell survival under nonselective conditions.

Polynucleotide: A double stranded or single stranded nucleic acid sequence of any length. Therefore, a polynucleotide includes molecules which are 15, 50, 100, 200 nucleotides long (oligonucleotides) and also nucleotides as long as a full length cDNA.

Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction. A nucleotide sequence 5' of a second nucleotide sequence is referred to as "upstream sequences;" a nucleotide sequence 3' to a second nucleotide sequence is referred to as "downstream sequences."

Polypeptide: Any chain of amino acids, regardless of length or post-translational modification (e.g., glycosylation or phosphorylation).

Prokaryote: Cell or organism lacking a membrane-bound, structurally discrete nucleus and other subcellular compartments.

Probes and primers: A nucleic acid probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al., (1989) and Ausubel et al., (1997).

Primers are short nucleic acids, preferably DNA oligonucleotides 15 nucleotides or more in length. Primers may be annealed to a complementary target DNA strand by nucleic acid hybridization to form a hybrid between the primer and the target DNA strand. The 3' hydroxyl end of the primer may be then extended along the target DNA strand through the use of a DNA polymerase enzyme. Primer pairs (one on either side of the target nucleic acid sequence) can be used for amplification of a nucleic acid sequence, e.g., by the polymerase chain reaction (PCR) or other nucleic-acid amplification methods known in the art.

Methods for preparing and using probes and primers are described, for example, in Sambrook et al. (1989), Ausubel et al. (1987). PCR primer pairs can be derived from a known sequence, for example, by using computer programs intended for that purpose such as Primer (Version 0.5, © 1991, Whitehead Institute for Biomedical Research, Cambridge, Mass.). Under appropriate conditions, the specificity of a particular probe or primer increases with its length. Thus, in order to obtain greater specificity, probes and primers may be selected that comprise 20, 25, 30, 35, 40, 50 or more consecutive nucleotides of related cDNA or gene sequence.

Promoter: An array of nucleic acid control sequences which direct transcription of a nucleic acid. A promoter includes necessary nucleic acid sequences near the start site of transcription, such as in the case of a polymerase II type promoter, a TATA element. Enhancer and repressor elements can be located adjacent or distal to the promoter, and can be located as much as several thousand base pairs from the start site of transcription. Examples of promoters include, but are not limited to, the SV40 promoter, the CMV promoter, the β-actin promoter, and tissue-specific promoters. Examples of tissue-specific promoters include, but are not limited to: probasin (which is promotes expression in prostate cells), an immunoglobulin promoter; a whey acidic protein promoter; a casein promoter; glial fibrillary acidic protein promoter; albumin promoter; β-globin promoter; an insulin promoter; and the MMTV promoter. In yet another embodiment, a promoter is a hormone-responsive promoter, which promotes transcription only when exposed to a hormone. Examples of hormone-responsive promoters include, but are not limited to: probasin (which is responsive to testosterone and other androgens); MMTV promoter (which is responsive to dexamethazone, estrogen, and androgens); and the whey acidic protein promoter and casein promoter (which are responsive to estrogen).

A hybrid promoter is a promoter that directs transcription of a nucleic acid in both eukaryotic and prokaryotic cells. One specific, non-limiting example of a hybrid promoter is a PGK-EM7 promoter. Another specific, non-limiting example of a hybrid promoter is PGK-Tnf.

Purified: The term purified does not require absolute purity; rather, it is intended as a relative term. Thus, for example, a purified lambda Beta preparation or ssDNA binding polypeptide is one in which the protein is more enriched than the protein is in its natural environment within a cell. Preferably, a preparation of lambda Beta is purified such that the polypeptide represents at least 50% of the total protein content of the preparation.

RecA: The RecA protein is a central protein that has an activity as in the recombination function of *E. coli.* Homologues are found in all other organisms. RecA protein allows two homologous DNAs to find each other among non-homologous DNAs and then trade or transfer strands with each other. This exchange occurs by RecA binding to a single stranded region in one of the DNAs and using that strand to search for its dsDNA homolog, binding to the dsDNA and causing the single strand to pair with its complement in the dsDNA ultimately displacing the identical strand of the duplex. This strand transfer generates a key intermediate in the RecA-mediated recombination process. recE recT genes and the Rac prophage: *E. coli* and other bacteria contain in their chromosomes remnants of viruses. These viruses or prophages are for the most part defective and may contain only a few genes of the original virus. In *E. coli*, one defective prophage is called Rac. Two genes, recE and recT of the Rae prophage, encode homologous recombination functions. These genes are normally silent but the sbcA mutation activates their constitutive expression. Thus, the sbcA mutant is active for recombination.

Recombinases: Proteins that, when included with an exogenous targeting polynucleotide, provide a measurable increase in the recombination frequency between two or more oligonucleotides that are at least partially homologous. A recombinase catalyses recombination of recombining sites (reviewed in Kilby et al., *TIG* 9:413–21, 1993; Landy, *Curr. Opin. Genet. Devel.* 3:699–707, 1993; Argos et al., *EMBO J.* 5:433–40, 1986). One specific, non-limiting example of a recombinase is Cre. Another specific, non-limiting example of a recombinase is a Flp protein. Other specific, non-limiting examples of a recombinase are Tn3 recombinase, the recombinase of transposon gamma/delta, and the recombinase from transposon mariner.

The Cre and Flp proteins belong to the lambda/integrase family of DNA recombinases. The Cre and Flp recombinases are similar in the types of reactions they carry out, the structure of their target sites, and their mechanism of recombination (Jayaram, *TIBS* 19:78–82, 1994; Lee et al., *J. Biol. Chem.* 270:4042–52, 1995). For instance, the recombination event is independent of replication and exogenous energy sources such as ATP, and functions on both supercoiled and linear DNA templates.

Recombinases exert their effects by promoting recombination between two of their recombining sites. In the case of Cre, the recombining site is a Lox site (see U.S. Pat. No. 4,959,317), and in the case of Flp the recombining site is a frt site. Similar sites are found in transposon gamma/delta, TN3, and transposon mariner. These recombining sites are comprised of inverted palindromes separated by an asymmetric sequence (Mack et al., *Nuc. Acids Res.* 20:4451–5, 1992; Hoess et al., *Nuc. Acids Res.* 14:2287–300, 1986; Kilby et al., *TIG* 9:413–21, 1993). Recombination between target sites arranged in parallel (so-called "direct repeats") on the same linear DNA molecule results in excision of the intervening DNA sequence as a circular molecule. Recombination between direct repeats on a circular DNA molecule excises the intervening DNA and generates two circular molecules. Both the Cre/Lox and flp/frt recombination systems have been used for a wide array of purposes such as site-specific integration into plant, insect, bacterial, yeast and mammalian chromosomes (Sauer et al., *Proc. Natl. Acad. Sci. U.S.A.* 85:5166–70, 1988). Positive and negative strategies for selecting or screening recombinants have been developed (Sauer et al., *J. Mol. Biol.* 223:911–28, 1992). The use of the recombinant systems or components thereof in transgenic mice, plants and insects among others reveals that hosts express the recombinase genes with no apparent deleterious effects, thus confirming that the proteins are generally well-tolerated (Orban et al., *Proc. Natl. Acad. Sci. U.S.A.* 89:6861–5, 1992).

Recombining site: Nucleic acid sequences that include inverted palindromes separated by an asymmetric sequence (such as a transgene) at which a site-specific recombination reaction can occur. In one specific, non-limiting example, a recombining site is a Lox site, such as LoxP or Lox 511 (see above). In another specific non-limiting example, a recombining site is a frt site. A frt site consists of two inverted 13-base-pair (bp) repeats and an 8-bp spacer that together comprise the minimal frt site, plus an additional 13-bp repeat which may augment reactivity of the minimal substrate (e.g. see U.S. Pat. No. 5,654,182). In other, specific non-limiting examples, a recombining site is a recombining site from a Tn3, a mariner, or a gamma/delta transposon.

Selection markers or selectable markers: nucleic acid sequences which upon intracellular expression are capable of conferring either a positive or negative selection marker or phenotypic characteristic for the cell expressing the sequence. The term "selection marker" or "selectable marker" includes both positive and negative selection markers. A "positive selection marker" is a nucleic acid sequence that allows the survival of cells containing the positive selection marker under growth conditions that kill or prevent growth of cells lacking the marker. An example of a positive selection marker is a nucleic acid sequence which promotes expression of the neomycin resistance gene, or the kanamycin resistance gene. Cells not containing the neomycin resistance gene are selected against by application of G418, whereas cells expressing the neomycin resistance gene are not harmed by G418 (positive selection). A "negative selection marker" is a nucleic acid sequence that kills, prevents growth of or otherwise selects against cells containing the negative selection marker, usually upon application of an appropriate exogenous agent. An example of a negative selection marker is a nucleic acid sequence which promotes expression of the thymidine kinase gene of herpes simplex virus (HSV-TK). Cells expressing HSV-TK are selected against by application of ganciclovir (negative selection), whereas cells not expressing the gene are relatively unharmed by ganciclovir. The terms are further defined, and methods further explained, by U.S. Pat. No. 5,464,764, which is herein incorporated by reference.

Selectable phenotype: A cell with a selectable phenotype is one that expresses a positive or negative selection marker.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar are the two sequences.

Methods of alignment of sequences for comparison are well-known in the art. Various programs and alignment algorithms are described in: Smith and Waterman, *Adv. Appl. Math.* 2:482, 1981; Needleman and Wunsch, *J. Mol. Bio.* 48:443, 1970; Pearson and Lipman, *Methods in Molec. Biology* 24:307–331, 1988; Higgins and Sharp, *Gene* 73:237–244, 1988; Higgins and Sharp, *CABIOS* 5:151–153, 1989; Corpet et al., *Nucleic Acids Research* 16:10881–90, 1988; Huang et al., *Computer Applications in BioSciences* 8:155–65, 1992; and Pearson et al., *Methods in Molecular Biology* 24:307–31, 1994. Altschul et al. (*Nature Genet.,* 6: 119–29, 1994) presents a detailed consideration of sequence alignment methods and homology calculations.

The NCBI Basic Local Alignment Search Tool (BLAST) (Altschul et al., *J. Mol. Biol.* 215:403–410, 1990) is available from several sources, including the National Center for Biological Information (NBCI, Bethesda, Md.) and on the Internet, for use in connection with the sequence analysis programs blastp, blastn, blastx, tblastn and tblastx. It can be accessed at the NCBI website, together with a description of how to determine sequence identity using this program.

Homologues of lambda Beta, Exo and Gam, and ssDNA binding proteins typically possess at least 60% sequence identity counted over full-length alignment with the amino acid sequence of the protein being evaluated (that is, lambda Beta, Exo or Gam, or ssDNA binding protein such as P22 Erf, RecT, and Rad52) using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 95%, at least 98%, or at least 99% sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. Methods for determining sequence identity over such short windows are described at the NCBI website One of skill in the art will appreciate that these sequence identity ranges are provided for guidance only; it is entirely possible that strongly significant homologs or other variants could be obtained that fall outside of the ranges provided.

Single-stranded DNA (ssDNA) and double-stranded DNA (dsDNA): ssDNA is DNA in a single polynucleotide chain; the DNA bases are not involved in Watson-Crick base pairing with another polynucleotide chain. dsDNA involves two or more complementary polynucleotide chains, in which the two polynucleotide chains are at least partially Watson-Crick base-paired to each other. Note that a segment of DNA may be partially ssDNA and partially dsDNA, for example if there are gaps in one polynucleotide chain of a segment of dsDNA, or there are 5' or 3' overhangs. ssDNA and dsDNA may contain nucleotide analogs, nonnaturally occurring or synthetic nucleotides, biotin, or epitope or fluorescent tags. ssDNA or dsDNA may be labeled; typical labels include radioactive isotopes, ligands, chemiluminescent agents, and enzymes.

Target nucleic acid sequence: The nucleic acid segment which is targeted for homologous recombination. Typically, this is a segment of chromosomal or extrachromosomal DNA in a cell. Extrachromosomal DNA harboring target nucleic acid sequences may include episomal DNA, plasmid DNA, bacterial artificial chromosome, phagemid artificial chromosomes, yeast artificial chromosomes, cosmids, and the like. The target nucleic acid sequence usually harbors a gene or gene fragment which will be mutated in some fashion upon homologous recombination. Examples of target nucleic acid sequences include DNA sequences surrounding the tyr 145 UAG amber mutation of galK, as described in Yu et al., *PNAS* 97:5798–5983, 2000, and in Example 3 of this application; the second exon of mouse hox 1.1 gene, as described in U.S. Pat. No. 5,464,764; the human hemoglobin S gene mutation as described in Example 15 of this application.

Targeting frequency: The frequency with which a target nucleic acid sequence undergoes homologous recombination. For example, extrachromosomal DNA is introduced into a eukaryotic cell. The extrachromosomal DNA has sequences capable of undergoing homologous recombination with a target intrachromosomal DNA sequence. After introducing the extrachromosomal DNA and allowing homologous recombination to proceed, the total number of cells may be determined, and the number of cells having the target DNA sequence altered by homologous recombination may be determined. The targeting frequency is the number of cells having the target DNA sequence altered, divided by the total number of cells. For example, if there are a total number of one million cells, and 1,000 of these cells have the target DNA sequence altered, then the targeting frequency is 1 in 1,000, or $10^{-3}$.

Transformed: As used herein, the term transformation encompasses all techniques by which a nucleic acid molecule might be introduced into such a cell, including transfection with viral vectors, transformation with plasmid vectors, and introduction of DNA (including DNA linked to Beta protein) by electroporation, lipofection, and biolistics.

Transgene: A foreign gene that is placed into an organism by introducing the foreign gene into embryonic stem (ES) cells, newly fertilized eggs or early embryos. In one embodiment, a transgene is a gene sequence, for example, a sequence that encodes a marker polypeptide that can be detected using methods known to one of skill in the art. In another embodiment, the transgene is a conditional knock-out allele.

Transgenic Animal: An animal, for example, a non-human animal such as, but not limited to, a mouse, that has had DNA introduced into one or more of its cells artificially. By way of example, this is commonly done by random integration or by targeted insertion. DNA can be integrated in a random fashion by injecting it into the pronucleus of a fertilized ovum. In this case, the DNA can integrate anywhere in the genome, and multiple copies often integrate in a head-to-tail fashion. There is no need for homology between the injected DNA and the host genome. In most cases, the foreign transgene is transmitted to subsequence generations in a Mendelian fashion (a germ-line transgenic).

Targeted insertion, the other common method of producing transgenic animals, is accomplished by introducing the DNA into embryonic stem (ES) cells and selecting cells in which the DNA has undergone homologous recombination with matching genomic sequences. For this to occur, there is homology between the exogenous and genomic DNA, and positive selectable markers are often included. In addition, negative selectable markers can be used to select against cells that have incorporated DNA by non-homologous recombination (random insertion).

Upstream: Refers to nucleic acid sequences that preceed the codons that are transcribed into a RNA of interest, or to a nucleic acid sequences 5' of a nucleic acid of interest. Similary, "downstream" refers to nucleic acid sequences that follow codons that are transcribed into a RNA of interest, or to nucleic acid sequences 3' of a nucleic acid of interest.

Variants of Amino Acid and Nucleic Acid Sequences: The production of lambda Beta, Exo or Gam, or other ssDNA binding polypeptide can be accomplished in a variety of ways. DNA sequences which encode for the protein, or a fragment of the protein, can be engineered such that they allow the protein to be expressed in eukaryotic cells, bacteria, insects, and/or plants. In order to accomplish this expression, the DNA sequence can be altered and operably linked to other regulatory sequences. The final product, which contains the regulatory sequences and the nucleic acid encoding the therapeutic protein, is operably linked into a vector, allowing stable maintenance in a cell. This vector can then be introduced into the eukaryotic cells, bacteria, insect, and/or plant. Once inside the cell, the vector allows the protein to be produced.

One of ordinary skill in the art will appreciate that the DNA can be altered in numerous ways without affecting the biological activity of the encoded protein. For example, PCR may be used to produce variations in the DNA sequence which encodes lambda Beta, Exo or Gam, or other ssDNA binding proteins. Such variants may be variants that are optimized for codon preference in a host cell that is to be used to express the protein, or other sequence changes that facilitate expression.

In one example, two types of cDNA sequence variants may be produced. In the first type, the variation in the cDNA sequence is not manifested as a change in the amino acid sequence of the encoded polypeptide. These silent variations are simply a reflection of the degeneracy of the genetic code. In the second type, the cDNA sequence variation does result in a change in the amino acid sequence of the encoded protein. In such cases, the variant cDNA sequence produces a variant polypeptide sequence. In order to preserve the functional and immunologic identity of the encoded polypeptide, such amino acid substitutions are ideally conservative in highly conserved regions. Conservative substitutions replace one amino acid with another amino acid that is similar in size, hydrophobicity, etc. Outside of highly conserved regions, non-conservative substitutions can more readily be made without affecting function of the protein. Examples of conservative substitutions are shown in Table 1 below.

TABLE 1

| Original Residue | Conservative Substitution |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |

TABLE 1-continued

| Original Residue | Conservative Substitution |
| --- | --- |
| Tyr | Trp; Phe |
| Val | Ile; Leu |

Variations in the cDNA sequence that result in amino acid changes, whether conservative or not, should be minimized in order to preserve the functional and immunologic identity of the encoded protein. The immunologic identity of the protein may be assessed by determining whether it is recognized by an antibody to the protein; a variant that is recognized by such an antibody is immunologically conserved. Particular examples of cDNA sequence variants introduce no more than 20, fewer than 10 amino acid substitutions, fewer than five amino acid substitutions, or about a single amino acid substitution, into the encoded polypeptide. Variant amino acid sequences may, for example, be at least 80, 90 or even 95% identical to the native amino acid sequence.

Yeast artificial chromosome (YAC): A vector used to clone DNA fragments (up to 400 kb); it is constructed from the telomeric, centromeric, and replication origin sequences needed for replication in yeast cells (see Ausubel et al.).

Use of the Lambda-encoded Red Recombination System in Recombineering Mediated by a Defective Prophage Bacteriophage λ contains a homologous recombination system termed Red, which is functionally analogous to the RecET recombination system of Rac. Like RecET, Red recombination requires two genes: redα or exo, which is analogous to recE, and redβ (or bet), which is analogous to recT). Exo is a 5'-3' exonuclease that acts processively on linear dsDNA. Beta binds to the ssDNA overhangs created by Exo and stimulates annealing to a complementary strand but cannot promote direct strand invasion and exchange on its own. The recombination functions of Exo and Beta are again assisted by λ phage-encoded Gam, which inhibits the RecBCD activity of the host cell. λ Red-mediated recombination events are 10 to 1000 times more efficient than those observed in recBC sbcBC or recD strains. Because homologous recombination is increased dramatically by the addition to the host of phage-encoded protein functions, this procedure is widely applicable to any *E. coli* strain and to other bacterial species as well.

Figure 2:
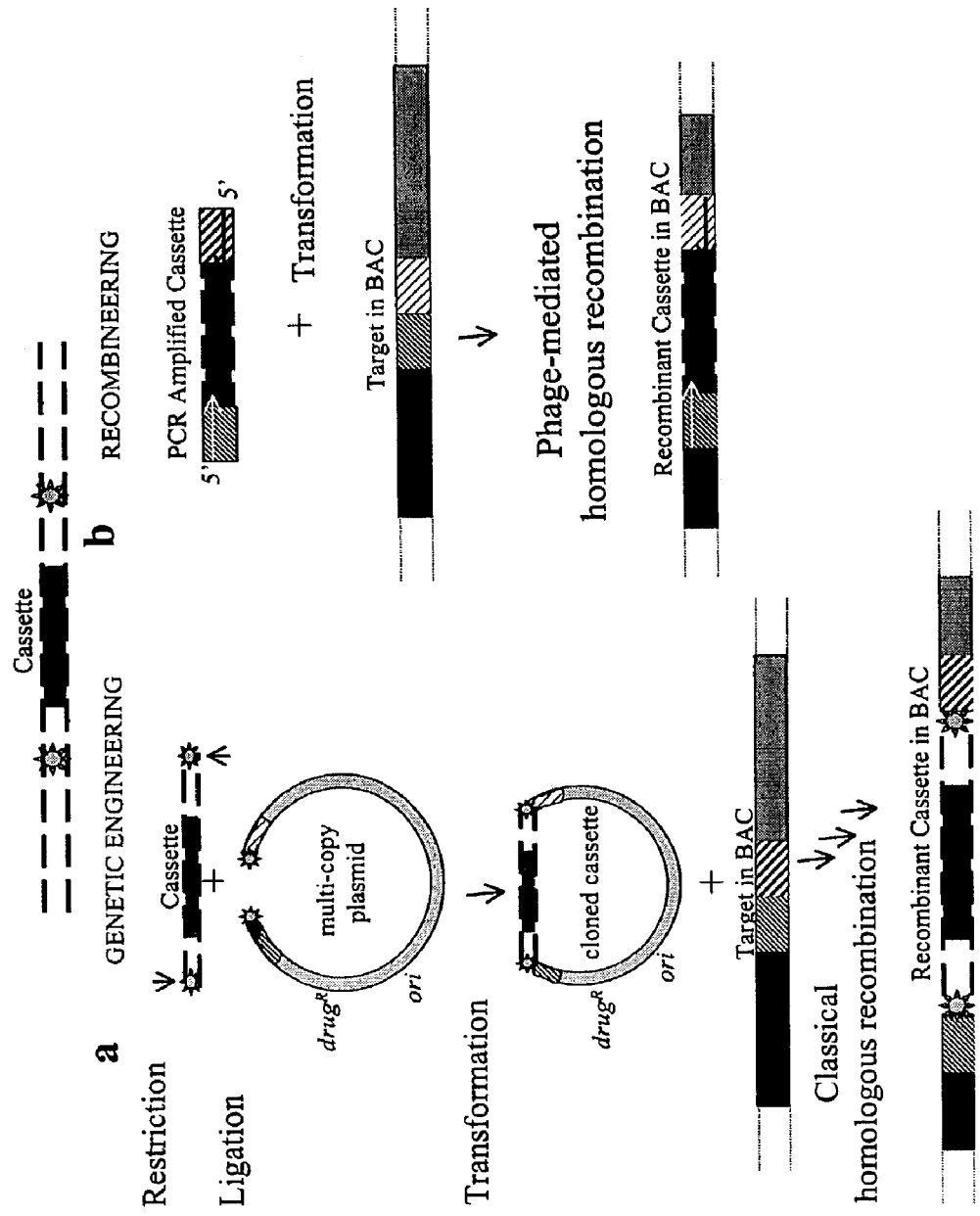
FIG. 2A is a schematic diagram showing classical recombinant technology.
FIG. 2B is a schematic diagram showing "recombineering" using homologous recombination, as disclosed herein.

A defective λ prophage-based system is disclosed herein for Red-mediated recombineering (see FIG. 2). In this system, Gam, Beta, and Exo are encoded by a defective lambda prophage, which is integrated into the *E. coli* chromosome of a bacterial cell (e.g. *E. coli*) (see FIG. 6 and FIG. 9). Expression of Gam, Beta, and Exo is under the tight control of a de-repressible promoter. In the example shown, the de-repressible pL promoter is under the control of the temperature-sensitive λ cI857 repressor. At 32° C., when the repressor is active, expression of the pL promoter and these genes is undetectable. However, when the cells are shifted to 42° C. for about a 15 minute period, the repressor is inactivated and the genes are expressed at very high levels. In contrast, promoters that can be activated, which are present on plasmids, are notoriously difficult to control and Red and Gam functions would be expressed even in the absence of the inducer, such as arabinose. Low-level expression of Gam causes a RecBCD defect, a condition that results in plasmid instability and loss of cell viability.

The tight regulation afforded by the prophage system, combined with the fact that the λ promoter, which drives Gam and Red expression is a very strong promoter, makes it possible to achieve recombination frequencies that are at least 50-fold higher than those found with the plasmid-based system used previously (see Muyrers et al, *Nucleic Acids Res* 27:1555–1557, 1999; Yu et al. *Proc Natl Acad Sci U.S.A.* 97:5978–5983, 2000), and several orders of magnitude higher than previously described strains in which linear recombination has been studied. The prophage itself is genetically stable, unlike plasmids, and does not rely on the presence of drug selection for maintenance.

FIG. 2 illustrates the design of primers for amplification of a dsDNA recombination cassette, and a strategy for generating recombinant DNA molecules and gene replacement. The steps are outlined below.

Classical recombinant DNA technology or genetic engineering has primarily relied upon the presence of restriction enzyme cleavage sites to judiciously cleave DNA and the use of DNA ligase to covalently join different DNAs to make the recombinants wanted. The ability to do genetic engineering has been simplified by the polymerase chain reaction (PCR), which allows restriction sites to be incorporated into linear PCR products thereby allowing more precise positioning of those sites. All genetic engineering technology breaks down, however, when cloning vehicles and the target contain hundreds of kilobases of DNA. Examples include the bacterial chromosome and large genomic BAC clones. Even rare restriction enzyme sites occur frequently on such large DNA molecules making the effort to use unique sites impossible. Furthermore, the in vitro manipulation of linear DNAs of this length is also extremely difficult. Therefore, once large BAC cloning technology became available in *E. coli,* modification of the BAC clones became the primary problem. Initially a combination of genetic engineering technology and classical homologous recombination techniques were adapted to modify the large genomic clones. Classical homologous recombination in *E. coli* depends upon significant (>500 bp) stretches of homology between DNAs.

FIG. 2A depicts a typical genetic engineering protocol to modify a target on a BAC clone with a cassette and compares that technology with the recombineering technology disclosed herein that uses special phage recombination functions. In general, there are many steps required for classical engineering, and the final product cannot be engineered as precisely as by the new recombineering technology. An advance in the recombineering methodology is the use of phage recombination functions that generate recombination products using homologies of 50 bp (or less). Note that the target homologies in FIG. 2A and FIG. 2B are represented by the striped boxes. In the method outlined in FIG. 2A, those boxes must be at least 500 bp long, whereas in the method outlined in FIG. 2B, they need only be about 40 to about 50 bp long.

Thus, in one example, genetic engineering steps to generate BAC recombinant include cleavage of the cassette DNA by a restriction enzyme, cleavage of target on plasmid by a restriction enzyme (wherein the vector has been pre-engineered to contain target fragments). The cassette is joined to the plasmid by DNA ligase, and the DNA is introduced into cells. Drug resistant (drug$^R$) clones are selected, and the plasmid is isolated. The cloned cassette is verified and subsequently transformed into the BAC strain. Several recombination steps are used to introduce the cloned cassette into the BAC.

In contrast, in one non-limiting example, recombineering steps to generate BAC recombinants can include the generation of two primers (white and black arrows, FIG. 2B), and the generation of a PCR amplified cassette with flanking homologies. In the example pictured in FIG. 2B, exemplary striped homology segments shown are 50 base pairs long, but they can be about 100 base pairs in length, or from about 200 to about 500 base pairs in length. Phage recombination functions are induced into a BAC strain or BAC DNA is introduced into strain carrying recombination functions. The cells containing the BAC and the recombination functions are transformed with a PCR cassette. A recombinant is generated in vivo, and can then be detected by selection or counter-selection, by direct screening (colony hybridization), or by detecting a label on the nucleic acid (e.g. when DNA includes a DNA adduct or a marker such as biotin)

As disclosed herein, in one specific, non-limiting example, the defective λ prophage was transferred to the BAC host strain DH10B so that it can be used for BAC engineering. The modified DH10B strain called DY380 can be transformed with BAC DNA at efficiencies of $10^{-6}$ to $10^{-4}$. The utility of DY380 cells for BAC engineering has been demonstrated by introducing a 250 kbp mouse BAC that contains the neuronal-specific enolase 2 (Eno2) gene into DY380 cells by electroporation and then modifying the BAC by introducing a Cre-expressing targeting cassette into the 3' end of the Eno2 gene using Red recombination (see Example 20). The targeting cassette was PCR-amplified from a template plasmid using chimeric 63 nucleotide (nt) primers. The 3' 21 nucleotides of each primer was homologous to the targeting cassette, while the 5' 42 nucleotides was homologous to the last exon of Eno2 where the cassette was to be targeted (see FIG. 10). DY380 cells were then electroporated with the amplified targeting cassette and correctly targeted colonies were obtained at an efficiency approaching $10^{-4}$ following the induction of Red expression; no targeted colonies were obtained in uninduced cells.

As also disclosed herein, the modified full length BAC was purified and injected in mouse zygotes and a BAC transgenic line established. Two other transgenic lines carrying a shorter 25 kbp subclone of the modified Eno2 gene on pBR322 were also established as controls. The 25 kbp subclone carries the entire modified Eno2 coding region as well as 10 kbp of 5' flanking sequence and 5 kbp of 3' flanking sequence. The activity of the Cre gene in the different transgenic lines was then assessed by crossing the mice to ROSA26 reporter mice. These mice carry a lacZ reporter that can be activated by Cre recombinase. In mice carrying the full length BAC transgene, Cre activity was detected in all Eno2-positive neurons. In contrast, not all Eno2-positive neurons expressed Cre in the transgenic mice carrying the smaller 25 kbp subclone, and the pattern of Cre expression varied between the two different 25 kbp subclone lines. These results are consistent with previous studies showing that regulatory sequences can be located hundreds of kilobases from a gene, and highlight the usefulness of BAC engineering for in this case generating Cre-expressing lines for use in conditional knockout experiments.

Arabinose-inducible flpe or Cre genes have also been introduced into the defective prophage carried in strain DY380. flpe is a genetically engineered flp that has a higher recombination frequency than the original flp (Buchholz et al., *Nat Biotechnol* 16:657–662, 1998, herein incorporated by reference). The site-specific recombinases Flpe and Cre are important tools used to add or delete DNA segments (e.g. drug cassettes). Flpe and Cre expression can be induced by the addition of arabinose and used to remove the selection marker from the targeted locus. This will be especially important in cases where the selection marker interferes with the expression of the targeted locus. However, even excision of the selectable marker by Flpe or Cre recombination leaves behind the frt or LoxP site as a scar on the targeted locus.

8Using the methods disclosed herein, conditional knock-out alleles (cko alleles) can be produced. These alleles allow inactivation of a gene of interest under specified biological conditions. Typically, a condition knockout (cko) allele is made by inserting recombination sites, such as, but not limited to, LoxP sites into two introns of a gene, flanking an exon, or at the opposite ends of a gene. Genes of interest include, but are not limited to, genes encoding polypeptides including, but not limited to cytokines, hormones, structural molecules, enzymes, transcriptional factors (e.g. Evi9) and others.

Expression of a recombinase, such as, but not limited to, Cre, in mice carrying the cko allele catalyzes recombination between the LoxP sites and inactivates the gene. In one embodiment, transgenic animals, such as, but not limited to, transgenic mice (cko mice), can be produced including a cko allele. These mice allow a gene to be inactivated in a tissue- or temporal-specific fashion. In one specific, non-limiting example, the mice include a tissue-specific, or temporal-specific promoter operably linked to a nucleic acid encoding a recombinase. Thus, the gene of interest is inactivated when the recombinase is expressed.

In one example of a method to produce a cko allele, two sets of PCR primers are produced and used to amplify two homologous regions of a BAC DNA. The two homologous regions can be about 100 to about 500 base pairs in length, such as about 200 to about 500 base pairs, or about 100 base pair regions. These regions of homology are used to subclone a BAC of interest into a vector, such as a plasmid in a cell. In one embodiment, a genomic fragment of about 5 to about 20 kilobases is inserted into a vector, such as a genomic fragment of about 10 to 15 kilobases in length. A LoxP site is then introduced into the subcloned BAC DNA by introducing a nucleic acid sequence encoding a selection marker flanked by two recombination sites, such as, but not limited to, LoxP sites (e.g., a fLOXed nucleic acid encoding a selection marker), using homologous recombination.

To introduce the nucleic acid sequence encoding a selection marker, a vector is utilized that includes a selection marker flanked by two recombination sites (recombination site 1), which are in turn flanked by sequences homologous to the BAC (homology arms). The homology arms include more than 100 base pairs homologous to the BAC DNA, such as about 200 to about 500 base pairs that are homologous to the BAC DNA.

This vector is utilized to introduce the selection marker flanked by the two recombining sites into the BAC DNA in a host cell. Specifically, expression of Red recombination functions in a cell, such as a bacterial cell, is used to induce recombination. In this manner, homologous recombination is used to introduce the selection marker flanked by two recombination sites (two recombination site 1) into the BAC DNA. The selectable marker can be used to identify cells that have undergone homologous recombination.

Following homologous recombination, expression of a recombinase in the cell results in the excision of the selection marker. In one specific, non-limiting example, the recombinase is Cre, and the recombination sites are LoxP sites. In another specific, non-limiting example, the recombinase is Flpe, and the recombination sites are frt recombination sites. Following expression of the recombinase, such as, but not limited to, Cre, a single recombination site (recombination site 1), such as, but not limited to, a LoxP site, remains in the BAC DNA.

A second corresponding recombination site (recombination site 1, e.g. a LoxP site) is introduced at a second (e.g., a downstream) site in the BAC DNA. In one specific, non-limiting example, the first and the second recombination sites are introduced into the BAC DNA such that they flank at least one exon included in the BAC DNA. In another specific, non-limiting example, the first and the second recombination sites are introduced into a first and a second intron of a single gene, respectively, wherein the first and the second intron are not the same intron.

To introduce the second recombination site, a nucleic acid sequence including (1) a selectable maker flanked by a second pair of recombination sites (recombination site 2) is introduced into the BAC DNA, and (2) a second recombination site (recombination site 1), is introduced into the BAC DNA. In one embodiment, a vector is utilized including, in 5' to 3' orientation, a first recombining site, a hybrid promoter operably linked to a nucleic acid encoding a selection marker, a second recombining site, and a third recombining site, wherein the first recombining site and the second recombining site can undergo recombination with each other in the presence of a single recombinase.

To introduce the nucleic acid sequence including the second recombination site the vector further includes the selection marker flanked by two recombination sites (recombination site 2) and another recombination site (recombination site 1). All of these elements (e.g., 5'-recombination site 2-selection marker-recombination site 2-recombination site 1-3', or 5'-recombination site 1 -recombination site 2-selection marker-recombination site 2-3' are in turn flanked by homology arms. The homology arms include more than 100 base pairs homologous to the BAC DNA,. such as about 200 to about 500 base pairs that are homologous to the BAC DNA.

Thus, in one specific, non-limiting example, a vector is introduced into a cell that includes:

5'-nucleic acid homologous to the BAC DNA-recombination site 2- nucleic acid encoding the selectable marker-recombination site 2-recombination site 1-nucleic acid homologous to the BAC DNA-3'.

Expression of Red recombination functions in a cell such as a bacterial cell, can be used to induce recombination, thereby inserting the selection marker flanked by two recombination sites (recombination site 2) and the additional recombination site (recombination site 1) into the BAC DNA. In one specific, non-limiting example, a nucleic acid is introduced into the BAC DNA having a configuration: 5'-recombination site 2-selectable marker-recombination site 2-recombination site 1-3'. In another embodiment, a nucleic acid is introduced into the BAC DNA having a configuration: 5'-recombination site 1-recombination site 2-selectable marker-recombination site 2-3'. The selectable marker can be used to select those cells having undergone recombination.

Recombination is then induced at recombination sites 2 using a site specific recombinase. In one specific, non-limiting example, if recombination sites 2 are frt recombination sites, Flpe is used to induce recombination. In another specific, non-limiting example, recombination sites 2 are LoxP sites and Cre is used to induce recombination. Following recombination, a recombination site (recombination site 1) remains in the BAC DNA.

Figure 17:
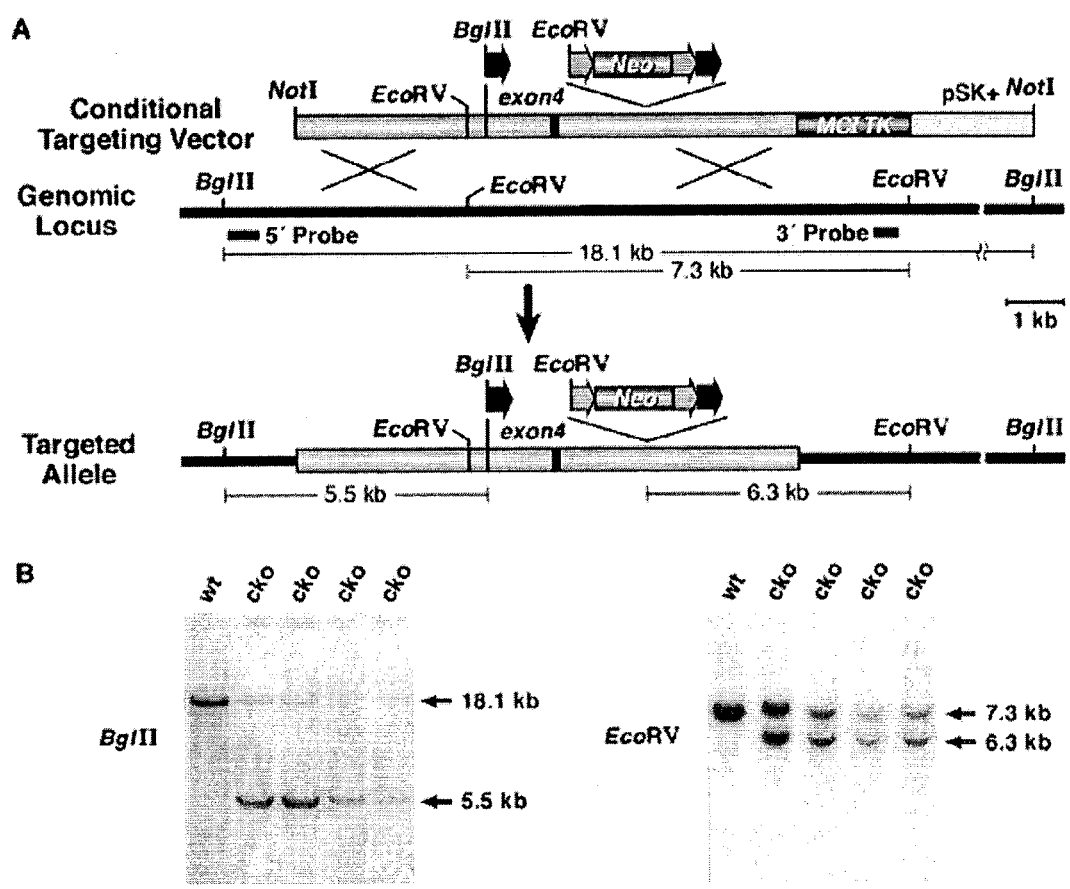
FIGS. 17A and 17B are a schematic diagram and digital image showing the identification of correctly targeted ES cell clones.
Figure 18:
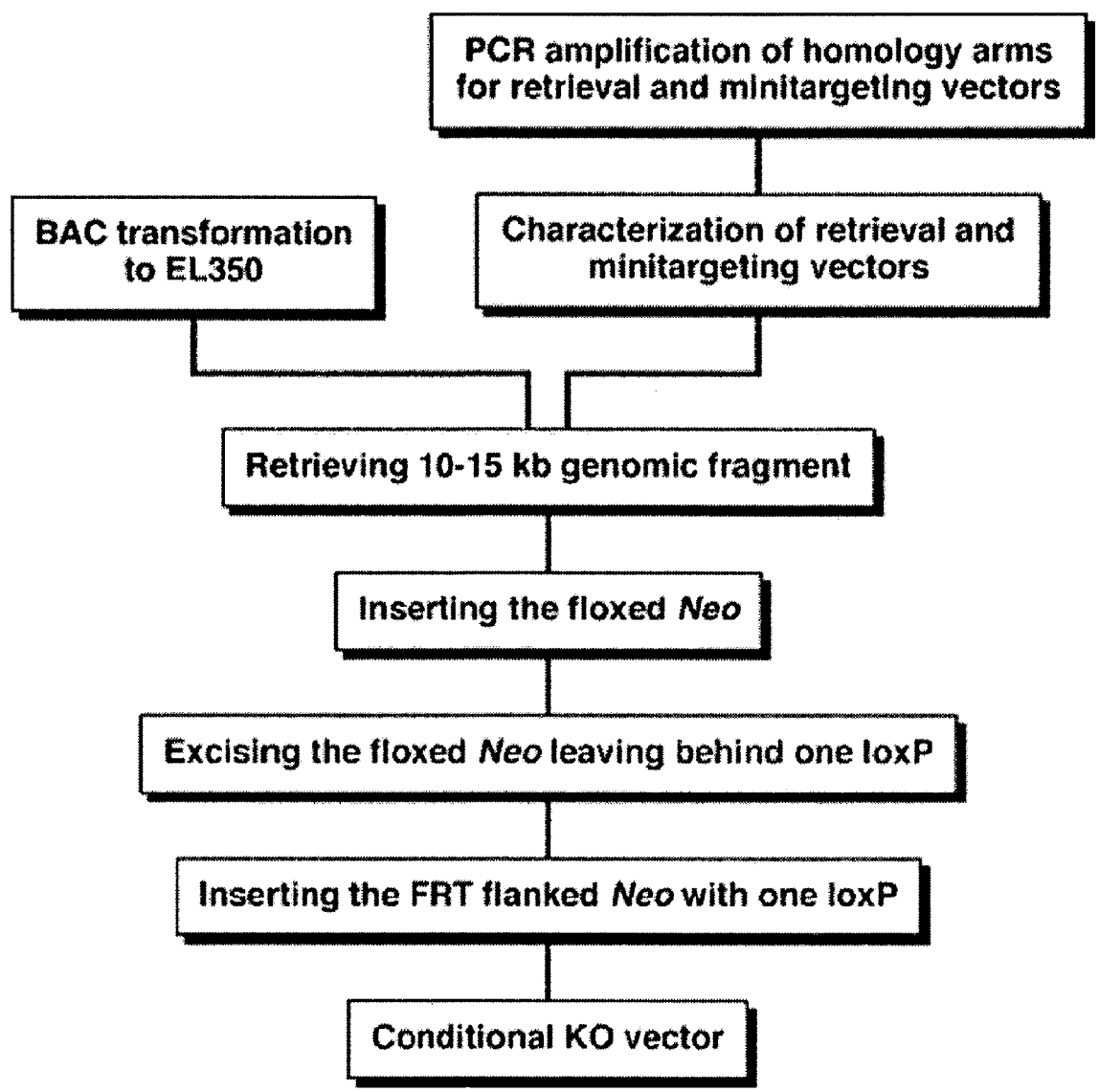
FIG. 18 is a flow chart of making a conditional knockout vector based on recombineering.

In this manner, a first recombination site and a second recombination site (two copies of recombination site that can be recombined using a recombinase, e.g. recombination site 1) are introduced in the BAC DNA to produce a "conditional knockout vector." The first recombination site and the second recombination site can be introduced flanking an exon of a gene of interest. Alternatively, the first recombination site and the second recombination site can be inserted each into a different exon. Upon induction of the expression of a recombinase that specifically induces recombination at the recombination sites, a "knockout" of a gene included in the BAC DNA, as no functional protein can be produced following transcription. A diagram of this process is shown in FIGS. 17 and 18. The conditional knockout vector can be linearized such that the BAC DNA including the gene of interest with the inserted recombination sites remains intact.

In one embodiment, a linearized conditional knockout vector is introduced into embryonic stem cells. Homologous recombination can occur either upstream or downstream of the gene of interest with the inserted recombination sites to stably integrate these nucleic acid sequences into a chromosome of the embryonic stem cell. The embryonic stem cell can be used to produce a transgenic animal. Any animal can be of use in the methods disclosed herein, including human and non-human animals. A "non-human animal" includes, but is not limited to, a non-human primate, a farm animal such as swine, cattle, and poultry, a sport animal or pet such as dogs, cats, horses, hamsters, rodents, or a zoo animal such as lions, tigers, or bears. In one specific, non-limiting example, the non-human animal is a transgenic animal, such as, but not limited to, a transgenic mouse, cow, sheep, or goat. In one specific, non-limiting example, the transgenic animal is a mouse.

Advances in technologies for embryo micromanipulation permit introduction of heterologous DNA into fertilized mammalian ova. For instance, totipotent or pluripotent stem cells, such as embryonic stem cells, can be transformed by microinjection, calcium phosphate mediated precipitation, liposome fusion, retroviral infection or other means. In one embodiment, homologous recombination is induced in an embryonic stem cell, such that an exogenous DNA is integrated into a chromosome of the embryonic stem cell. The transformed cells are then introduced into the embryo, and the embryo then develops into a transgenic animal. Reviews of standard laboratory procedures for the introduction of heterologous DNAs into mammalian (mouse, pig, rabbit, sheep, goat, cow) fertilized ova include: Hogan et al., *Manipulating the Mouse Embryo,* Cold Spring Harbor Press, 1986; Krimpenfort et al., *Bio/Technology* 9:86, 1991; Palmiter et al., *Cell* 41:343, 1985; Kraemer et al., *Genetic Manipulation of the Early Mammalian Embryo,* Cold Spring Harbor Laboratory Press, 1985; Hammer et al., *Nature* 315:680, 1985; Purcel et al., *Science* 244:1281, 1986; Wagner et al., U.S. Pat. No. 5,175,385; Krimpenfort et al., U.S. Pat. No. 5,175,384.

Thus, in one specific, non-limiting example, a "conditional knockout transgenic animal" is generated including the gene of interest including the two recombination sites (e.g. including two copies of recombination site 1 in a gene of interest, such as flanking an exon of a gene included in the BAC). To knockout expression of the gene of interest in the transgenic animal, a recombinase is expressed in a cell of the transgenic animal. In one specific, non-limiting example, to generate a mouse wherein this knockout can occur, a conditional knockout transgenic mouse can be mated to a second transgenic mouse carrying a transgene including a temporal- or tissue-specific promoter operably linked to a transgene encoding the recombinase. Offspring are selected that carry the gene of interest including the two recombination sites, and the gene encoding the recombinase. In these animals, the gene is knocked out in those cells wherein the recombinase is expressed.

Selection cassettes, and vectors including these selection cassettes, for use in these methods disclosed herein are also provided by this specification. In one embodiment, the cassette includes:

Recombinations site 2-hybrid promoter-selection marker 1-recombination site 2-recombination site 1.

Suitable recombination sites include, but are not limited to, frt, LoxP, or Tn3, ISCF-1, a mariner, or a gamma/delta transposon recombination site. In the selection cassette described above, the sequences of recombination site 2 and recombination site 1 differ from each other, and are recognized by different recombinases. Suitable hybrid promoters include PGK-EM7, for example, as included in PL451 (ATCC Deposit No. PTA-4996, deposited Feb. 5, 2003), PL450, PL452 (ATCC Deposit No. PTA-4997, deposited Feb. 5, 2003), and PL459. Suitable selection markers include neomycin resistance, ampicillin resistance, kanamycin resistance, or any sequence that produces sensitivity or resistance to an antibiotic when introduced into a cell. Selection markers further include any polypeptide sequence for which a selection system is available (e.g. beta-galactosidase).

An example of this selection cassette is:
 frt-hybrid promoter-selection marker-frt-LoxP or
  frt-PGK-EM7-selection marker-frt-LoxP or
   frt PGK-EM7-neo-frt LoxP or
 LoxP-hybrid promoter-selection marker LoxP-frt.

Exemplary selection cassettes of use in the methods disclosed herein are PL451 (ATCC Deposit No. PTA-4996, deposited Feb. 5, 2003) and PL452 (ATCC Deposit No. PTA-4997, deposited Feb. 5, 2003).

BAC Modification Without Leaving Markers or 'Scars' at the Target Site and Direct Genomic Modification A two-step procedure for BAC targeting has been developed wherein many kinds of mutations can be introduced into BACs without leaving behind a selectable marker, such as a drug selection marker, at the targeted locus. In one embodiment, a two-step procedure is utilized. This is exemplified in the following specific, non-limiting example. A PCR-generated targeting cassette containing a sacB-neo fusion gene was targeted to a BAC or other DNA. Cells containing the sacB-neo cassette targeted to the genomic DNA of the BAC were then transformed with a second targeting DNA to the same region. This cassette was designed to replace the sacB-neo cassette, and in one instance, contained short genomic sequences that carried a more subtle mutation, such as a small insertion. By placing these newly transformed cells on media with 7% sucrose, selective pressure was applied against SacB expression, which converts sucrose to a bacteriotoxin (Muyrers et al., *EMBO Rep* 1:239–243, 2000). Growth on sucrose plates thus selected for cells that have potentially replaced the sacB-neo targeting cassette with the second targeting cassette containing the small insertion. Because spontaneous mutations occur in sacB to cause sucrose resistance at frequencies approaching 1 in $10^4$, recombinants were identified among sucrose resistant colonies as those that have also become neomycin sensitive. As disclosed herein, by combining the power of Red recombination with selection/counterselection using sacB-neo, other kinds of genetic changes besides insertions can also be generated, including deletions and point mutations, and these mutations can be introduced into virtually any large DNA molecule such as a BAC, PAC, or the E. coli chromosome without any accompanying selectable marker.

The high frequency of recombination generated by the defective prophage system described herein also makes it possible to modify a bacterial genome or a BAC in a single step without drug selection or counterselection. In one specific, non-limiting example, a 24-bp flag tag was introduced into a 125-kbp BAC directly by recombination, without selection into the 5' end of the SRY-box containing gene 4 (Sox4) (e.g., see Examples 17 and 22). The recombinants were found by screening individual cells from the BAC electroporated culture.

Because homologies involved in Red-mediated recombination can be very short, targeting cassettes can also be made by simply annealing two complementary synthetic ssDNA oligonucleotides together. As described herein, a 70 bp targeting cassette constructed in this manner recombines with the E. coli chromosome to create point mutations at frequencies approaching one in a thousand electroporated cells. Point mutations corresponding to human disease-causing mutations can thus be introduced into any human or mammalian gene carried on a BAC with ease and the affect of this mutation on gene function assayed in a transgenic that carries a null mutation in the corresponding mouse gene.

Cloning DNA by Gap Repair

Figure 8:
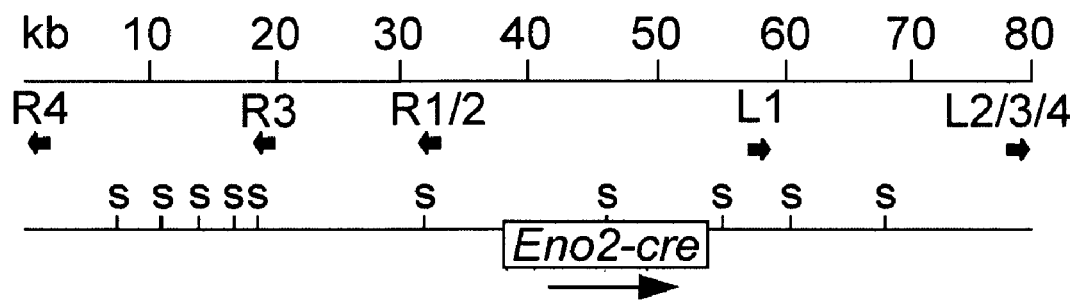
FIG. 8 is a schematic diagram illustrating the use of the gap repair to subclone fragments as large as 80 kbp from BACs.
Figure 8:
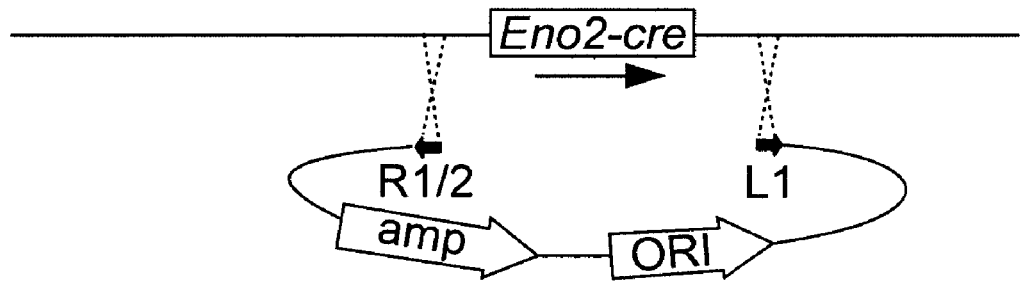
Figure 10:
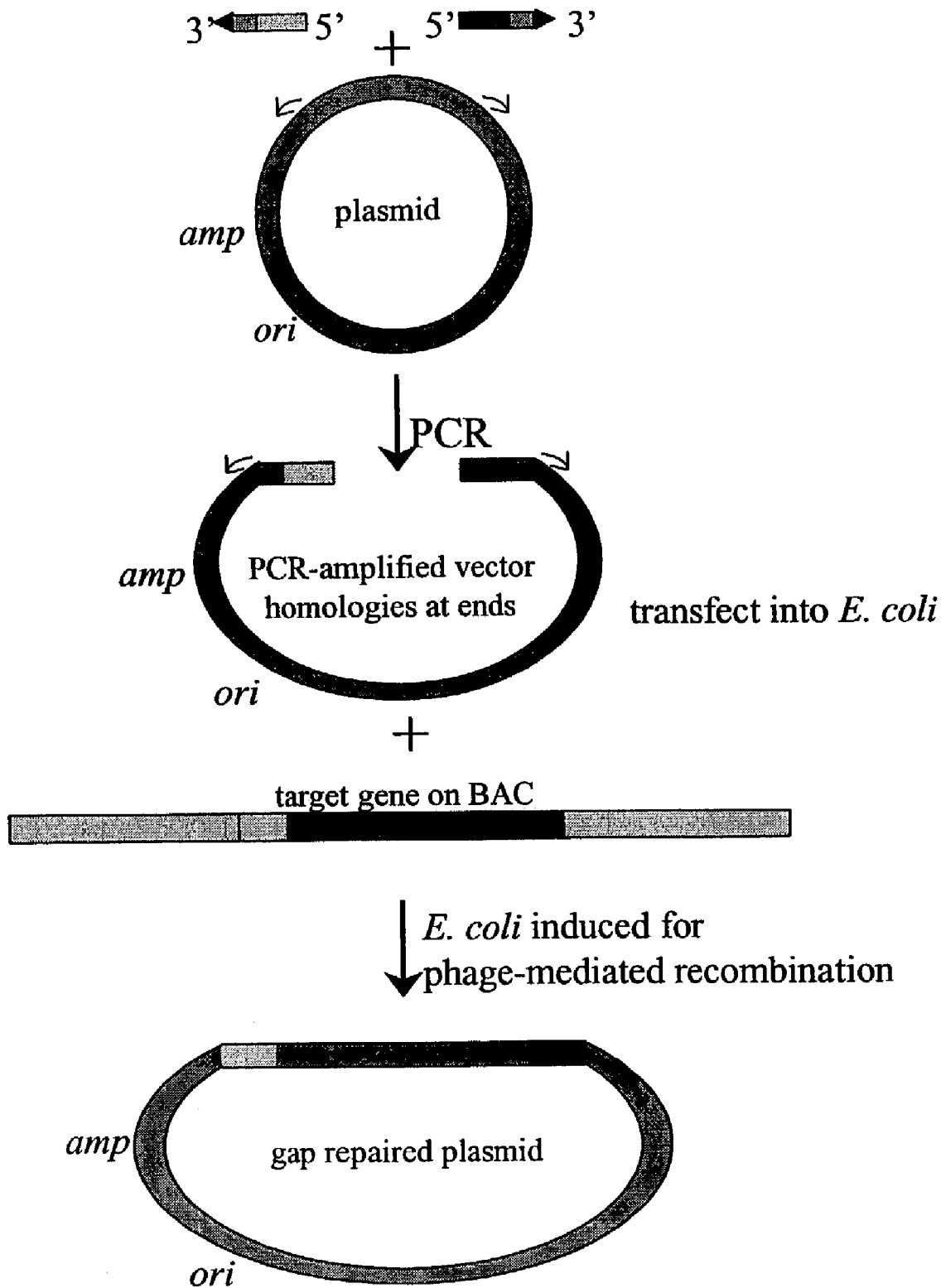
FIG. 10 is a schematic diagram of in vivo cloning by recombination using gap repair of a linear vector plasmid. The method of in vivo cloning uses two linear DNAs, a vector and a target DNA, that have homologies to each other at their ends. Both are electroporated into competent cells to allow recombination and gap repair of the plasmid. The linear vector is made in a similar way to that shown in FIG. 8.
Figure 11:
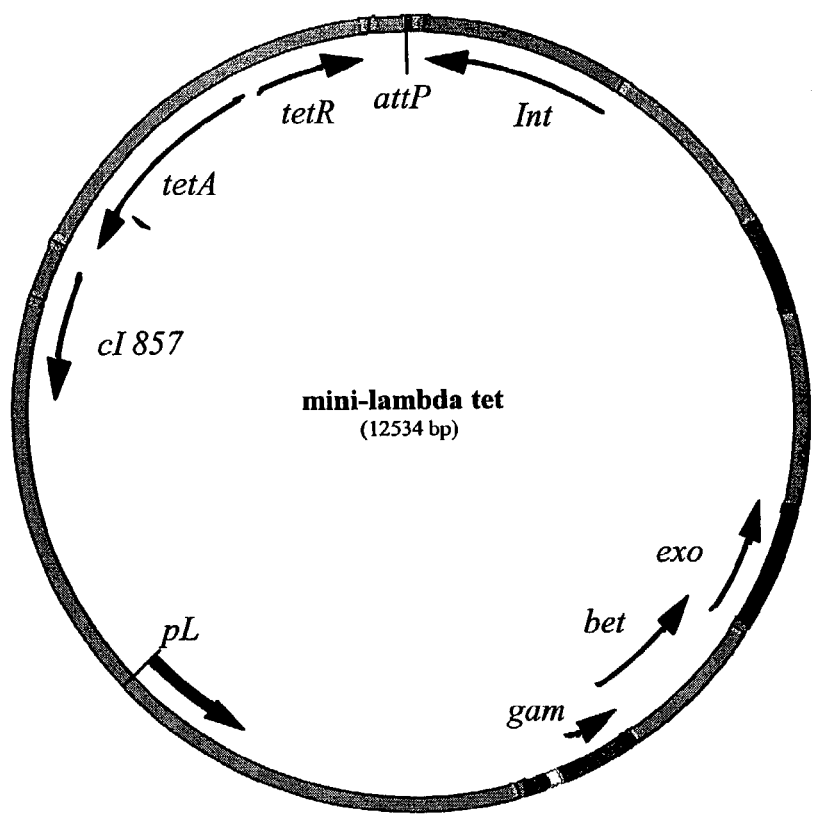
FIG. 11 is a schematic diagram of in vivo retrieving of DNA from BAC clones. Retrieving of segments up to 80 kbp from BACs into PCR-amplified vectors has been possible using recombineering techniques disclosed herein. Here only the plasmid is linearized and transformed into a recombination competent cell containing the BAC. Recombination occurs between homologies on the end of the linear vector and the BAC. This method eliminates standard cloning technology from the BAC, and importantly, the cloned segment is never replicated in vitro, thereby reducing the chance of extraneous changes in the sequence.

Fragments can be subcloned from BACs by Red-mediated recombination without the use of restriction enzymes or DNA ligases. Thus, any region of the BAC is amenable to subcloning, and subcloning does not depend on the placement of appropriate restriction enzyme sites. Subcloning relies on gap repair to recombine the free ends of a linear plasmid vector with homologous sequences carried on the BAC. An example is shown in FIGS. 8 and 10. The linear plasmid vector with, for example, an amp selectable marker and an origin of replication carries the recombinogenic ends. The vector is generated, for example, by polymerase chain reaction (PCR) amplification using two chimeric primers. The 5' end of each primer has homology to the extremities of the BAC sequence to be subcloned; the 3' end of each primer is used to prime and amplify the linear plasmid DNA. Recombination generates a circular plasmid in which the DNA insert is retrieved from the BAC via gap repair. Circular recombinant plasmids are selected by their drug resistance (e.g. Amp$^R$) phenotype. Different sizes of fragments that can be subcloned depending on the cloning vector utilized. With a high copy vector such as pBluescript, fragments up to about 25 kbp are subcloned. However, with a lower copy vector such as pBR322 is used, fragments as large as about 80 kbp can be subcloned. These larger fragments were shown to be more accurately expressed in a tissue specific manner (as was the entire BAC clone, see above).

A Mobilizable Lambda Prophage

Figure 6:
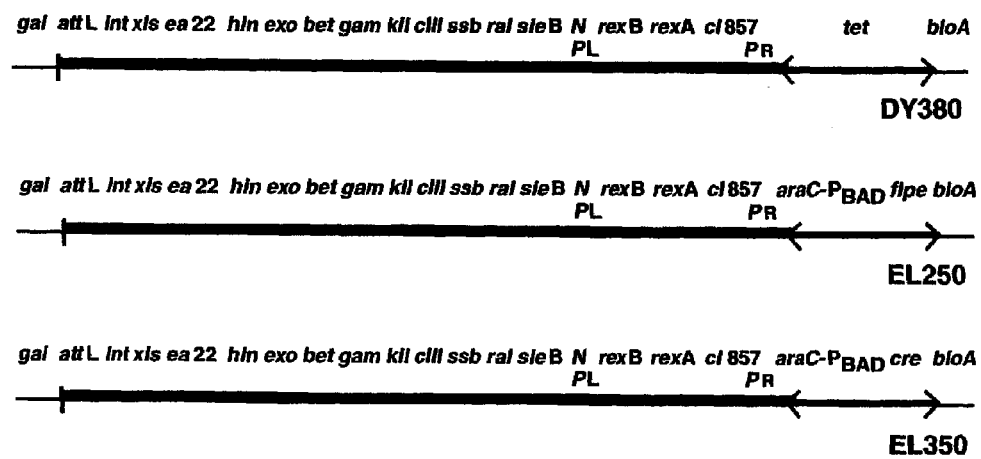
FIG. 6 is a linear depiction of the modified defective lambda prophage as integrated on the $E.$ $coli$ chromosome of DY380, EL250, and EL350 cells. This figure illustrates that the defective prophages used for BAC engineering contain the λ genes from cI857 to int. $P_L$ (or pL) and $P_R$ denote the lambda left and right promoters, respectively. The gam and red genes, exo and bet are under the control of $P_L$, which is repressed by the temperature-sensitive repressor, cI857 at 32° C. and de-repressed at 42° C. tet replaces the segment from cro-bioA in DY380 cells. The araC-$P_{BAD}$flpe cassette or the araC-$P_{BAD}$cre cassette replaces the segment from cro-bioA in EL250 or EL350 cells, respectively. The promoter of the araBAD operon ($P_{BAD}$), which can be induced by L-arabinose, controls the expression of the flpe or Cre genes. Thick black lines designate the prophage while thin lines represent $E.$ $coli$ sequence. < >defines the ends of the cro-bioA region that was replaced with tet, araC-$P_{BAD}$flpe, or araC-$P_{BAD}$cre.
Figure 9:
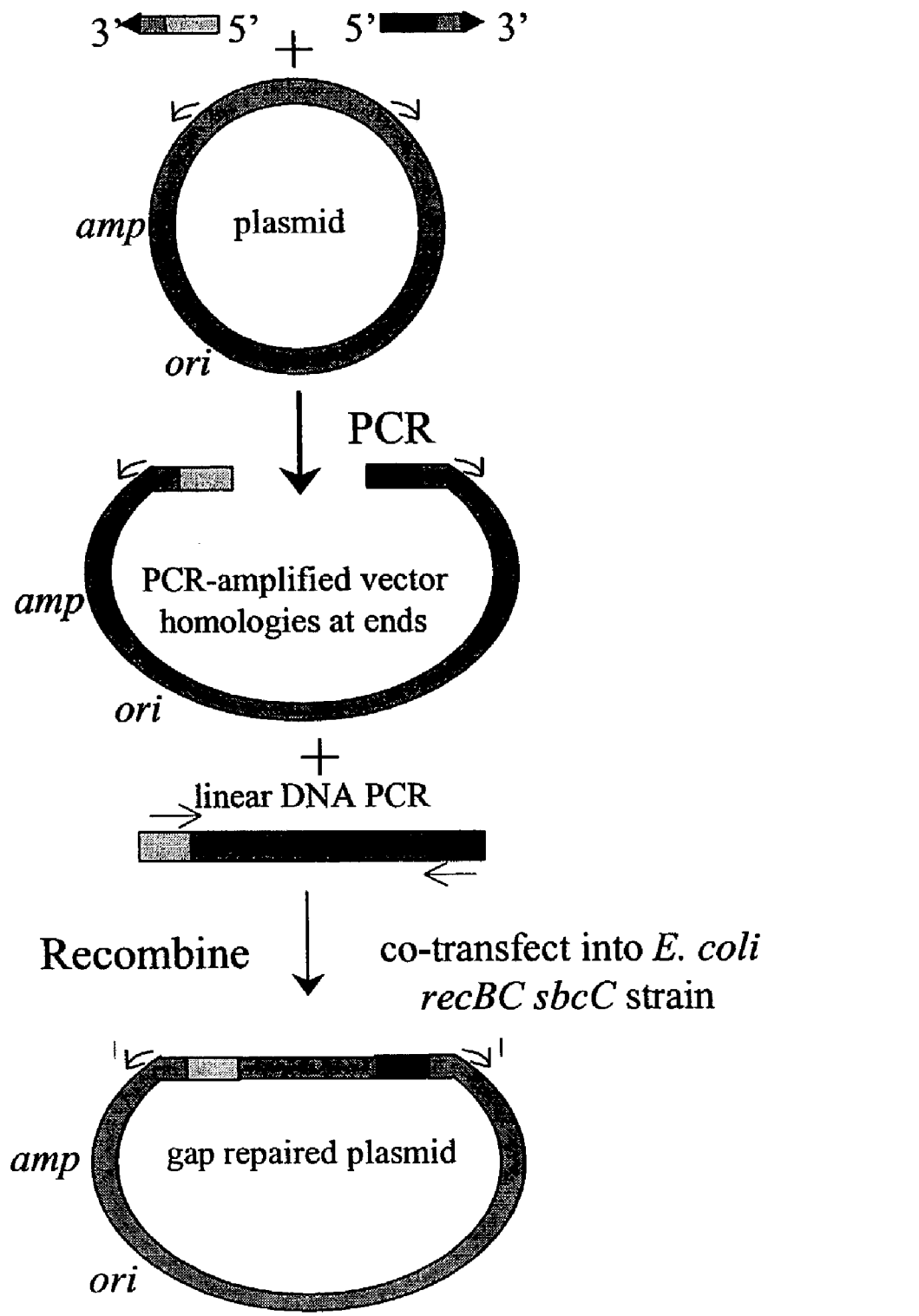
FIG. 9 is a schematic diagram of a defective λ prophage. The defective prophage DY380 expressing the λ Exo, Beta, and Gam functions is shown with the genes under $P_L$ promoter control and the temperature sensitive repressor, CI857. Advantages and disadvantages of the systems are described. The genes encoding Cre and Flpe are present on other derivatives of DY380 (EL250 and EL350) and replace the tet gene as shown.
Figure 12:
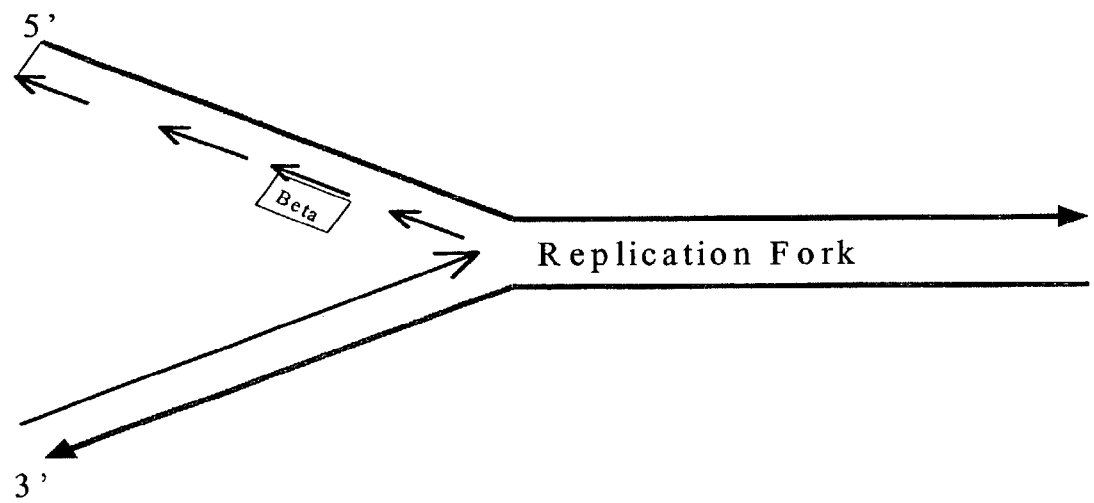
FIG. 12 is a schematic diagram of a mini-lambda DNA circle. This lambda DNA element is not a plasmid and lacks any replication origin activity. It does contain the lambda cI857 repressor and the pL operon that the repressor controls. It also contains a cassette encoding a drug marker, in this case the tet genes. This DNA when transformed into most strains including the BAC strains makes Int protein allowing integration of the circular DNA at the λ attachment site on the bacterial chromosome, and cI857 repressor to allow repression of pL. The integrated mini-lambda is stable but able to be induced at 42° C. to activate Gam, Beta, and Exo expression to make the cell recombination competent.

As disclosed herein, recombination functions were expressed from their native location in the pL operon of a lambda prophage using the natural λ repressor controls (FIG. 9). However, one limitation of the defective prophage system as disclosed in FIGS. 6 and 9 is that BACs under study must be moved into recombination-proficient DY380 cells before the BAC can be manipulated. In order to overcome this limitation, a novel prophage derivative has been generated that is isolated as a mini-lambda circle DNA carrying a selectable marker (e.g. a drug-resistance marker such as tet$^R$ cassette) and containing the exo, bet, and gam genes under control of the temperature inducible cI857 repressor (FIG. 12). This mini-lambda can be transformed into any bacterial cell, such as a DH10B cell that carry a BAC. The mini-lambda then integrates at the lambda attachment site to generate the defective prophage. This mobilizable prophage makes it possible to introduce the prophage into BAC-containing DH10B libraries and obviates the need to transfer the BAC to DY380 cells.

Recombineering Using ssDNA

Recombineering, or the use of a recombinase to mediate recombination using homology arms sufficient to induce recombination, as disclosed herein, can be performed using single-stranded oligos as the targeting cassette). As described in the Examples below (e.g., see Example 3), in E. coli, a single base change has been substituted in the galK gene and a 3.3 kbp insertion removed from the galK gene using single-stranded oligos. Single-stranded oligos have also been used to cure 5 different Tn10 insertions at different places on the E. coli chromosome. Recombineering using single-stranded oligos is very efficient with up to 6% of the electroporated cells being recombinant. Whereas Exo, Beta, and Gam facilitate recombination of PCR amplified dsDNA cassettes with flanking homologies, only Beta is required for ssDNA recombination (see FIG. 13). Maximum recombination is achieved with oligonucleotides of about 70 bases in length, although oligonucleotides of about forty to sixty bases in length can also be used to achieve recombination, albeit at a 5-fold lower frequency. In one embodiment, ssDNA of about 40 to about 70 nucleotides in length is utilized. In another embodiment, ssDNA of about 70 to about 100 nucleotides in length is utilized. In a further embodiment, a ssDNA of about 70 to about 1,000 nucleotides in length is utilized. Interestingly, Beta-mediated recombination activity is less efficient when ssDNA molecules are about 1,000 bases in length. In yet another embodiment, the ssDNA is labeled, such as with a biotinylated nucleotide, a methylated nucleotide, or a DNA adduct.

Figure 13:
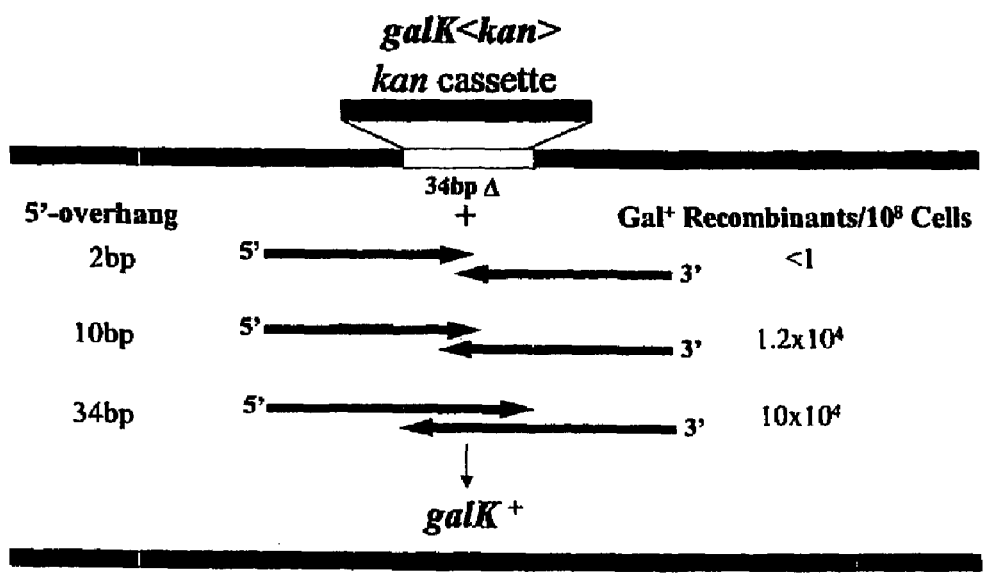
FIG. 13 is a schematic diagram of recombination of ssDNA into the genome. When ssDNA is electroporated into cells, it is bound by Beta protein and recombined into the genome or into a BAC plasmid by homology. Evidence suggests that Beta-bound ssDNA anneals to its ssDNA complement at the replication fork. The strand of DNA corresponding to that made by lagging strand synthesis is most recombinogenic suggesting that Beta simply anneals the ssDNA to a gap caused by DNA replication.

Recombination with either of two complementary DNA oligonucleotides has revealed that although either strand can be efficiently used for recombination, one strand is more competent for recombination than the other. This strand bias has been examined at several positions around the bacterial chromosome with the result that the preferred strand correlates with the lagging strand of DNA replication for each site tested. Without being bound by theory, these results indicated that strand bias is associated with the replication direction through the region being targeted and that ssDNA recombination occurs efficiently near the replication fork. The process of DNA replication results in transient regions of ssDNA that may be accessible to Beta-mediated annealing of the ssDNA oligo. Although recombination occurs on the leading strand, the increased recombination efficiency of the lagging strand oligos may reflect the increased frequency of single-stranded regions during lagging versus leading strand synthesis (FIG. 13). DNA polymerase and DNA ligase could then complete the joining of the annealed oligo to the lagging strand. Without being bound by theory, the increased frequency of ssDNA recombination probably reflects the fact that ssDNA recombination occurs through a simpler mechanism than dsDNA recombination. The ssDNA recombination may require only annealing of one single-stranded oligo to single-stranded regions in the replicating target DNA. Moreover, ssDNA recombination also occurs in yeast with a strand bias that may also be dependent upon replication. The yeast functions required for this recombination are, however, unknown making the finding that only the Beta function from phage λ is required in *E. coli* that much more significant.

Using the methods disclosed herein, point mutations can be introduced into a nucleic acid sequence of interest. In one specific, non-limiting example, a point mutation was engineered into the mouse Brca2 carried on a BAC using a 70 nt oligo. The targeting efficiency was several times higher than would be found with dsDNA created by annealing oligos and at least 50 times higher than with dsDNA generated by PCR and containing large regions of nonhomology in their center. A 140 nt oligonucleotide has also been used to introduce a 29 amino acid in-frame deletion into exon11 of the Brca2 gene and a 1.93 kb deletion into the BAC vector backbone (Swaminathan et al. Genesis 29:14–21, 2001, herein incorporated by reference). Finally, a 164 nt oligo has been used to introduce a 24 bp flag tag into the 5' end of Brca2. The targeting efficiency for the 164 nt oligo (7.7× $10^{-3}$) was nearly the same as the targeting efficiency for generating deletions using 140 nt oligos (8.3×$10^{-3}$ and 5.4×$10^{-3}$, respectively).

The disclosure is illustrated by the following non-limiting Examples.

EXAMPLES

Example 1

Modified Lambda Prophage for Defined Expression of Recombination Proteins

The molecular genetics of lambda bacteriophage, including its lytic and lysogenic growth cycles, is described in Sambrook et al., Bacteriophage Lambda Vectors, Chapter 2 in *Molecular Cloning: a Laboratory Manual*, 2nd Ed., (c) 1989 (hereinafter Sambrook et al., Ch. 2); Stryer, Control of Gene Expression in Procaryotes, Chapter 32 in *Biochemistry* 3rd Ed., pp. 799–823, (c) 1988 (hereinafter Stryer); and Court and Oppenheim, pp. 251–277 in Hendrix et al. eds., *Lambda II*, Cold Spring Harbor Lab Press, (c) 1983 (hereinafter Court and Oppenheim). The complete sequence of lambda is known (see GenBank Accession No. NC 001416, herein incorporated by reference).

Phage lambda has a well-characterized homologous recombination system. Double strand breaks in DNA are the initiation sites for this recombination (Thaler et al., *J. Mol. Biol.* 195:75–87, 1987). Lambda exonuclease (Exo) degrades processively from the 5' ends of these break sites, and lambda Beta binds to the remaining 3' single strand tail, protecting and preparing the recessed DNA for homologous strand invasion (Little, *J. Biol. Chem.* 242:679–686, 1967; Carter et al., *J. Biol. Chem.* 246:2502–2512, 1971).

The lambda recombination system containing exo and bet without gam is efficient at gene replacement using linear substrates with homology arms of more than 1,000 bp in a strain lacking RecBCD nuclease (Murphy, *Journal of Bacteriology* 180:2063–2071, 1998). To test homology arms of less than 100 bp long as substrates for lambda-mediated recombination, a lambda prophage was modified to express high levels of phage recombination functions for a defined amount of time.

FIG. 1 depicts the defective λ prophage on the *E. coli* chromosome. The defective prophage contains λ genes from cI to int. The pL operon is intact and expressed under control of the temperature-sensitive lambda cI-repressor (allele cI857). A deletion (dotted line) removes the right side of the prophage from cro through attR and including bioA (Patterson et al., Gene 132:83–87, 1993). On the chromosome, the nadA and gal operons are to the left of the prophage, and the bio genes without bioA are to the right. Genes of the λ prophage are shown on the solid line, and genes of the host are shown on the broken line. pL and PR indicate the early left and right promoters of λ. attL and attR indicate the left and right attachment sites of λ. The lambda genes and functions are described in Sambrook et al., chapter 2, Stryer, and Court and Oppenheim.

The absence of cro-repressor allows pL operon expression to be fully de-repressed when the temperature sensitive cI-repressor is inactivated at 42° C. The cro to bioA deletion removes the replication and lytic genes of the prophage. The functions encoded by these lytic genes are toxic to the cell and cause cell death within 7 minutes after a normal prophage induction. Functions present in the pL operon are also toxic but kill cells only after 60 minutes of continuous induction (Greer, *Virology* 66:589–604, 1975; Kourilsky et al., *Biochimie* 56:1517–1523, 1974). Thus, shifting of cells containing the pL operon construct from repressed conditions at 32° C. to induced conditions at 42° C. allows pL operon expression. Shifting the cells back from 42° C. to 32° C. (or lower) within 60 minutes reestablishes repression and prevents cell death.

As the following examples will demonstrate, this modified lambda prophage has produced unexpected advantages in mediating homologous recombination. These unexpected advantages include surprisingly high recombination efficiency, precise control of recombination functions, effective recombination with short homology arms, and ability to generate homologous recombinants with polynucleotides other than long double-stranded DNA. Without wishing to be bound by a single explanation of the observed effects, it is likely that these unexpected advantages accrue from incorporation of the lambda red genes on the prophage in their native context, thereby limiting the number of copies of the lambda recombination genes. In addition, use of the pL promoter confers the ability to precisely control the timing and production of large amounts of lambda recombination gene expression.

This system is not limited to expression in *E. coli*, but can also work in other bacteria, such as *Salmonella* and others. It can also work in eukaryotic cells, such as yeast or mammalian cells, with selection of appropriate promoters, and with other modifications of the present to allow expression of the lambda recombinase genes. In one specific, non-limiting example, in another bacteria, genes between gam and N (including N but not gam) can be deleted to remove transcription terminators.

Although the pL promoter is used to illustrate the invention, other de-repressible, inducible or constitutive promoters could be used. Specific, non-limiting examples of inducible promoters are drug inducible promoters (e.g. a tetracycline inducible promoter) metal inducible promoters (e.g. the metallathione promoter), or a hormone inducible promoter (e.g. a steroid responsive element).

The pL promoter could also be used to drive expression of, for example, P22 genes such as erf or of RecE and RecT.

Example 2

Bacterial Strains, Expression of pL Operon, Electroporation Methods, Identification of Recombinants Bacterial strains used in this work are listed in Table 2.

TABLE 2

| Strains | Genotype |
|---|---|
| WJW23 | his ilv rpsl Δ(argF-lac)U169 nadA::Tn10 gal490 λcI857 Δ(cro-bioA) |
| ZH1141 | W3110 Δ(argF-lac)U169 gal490 λN:lacZ Δ(N-int) cI857 Δ(cro-bioA) |
| BR3677 | lacI$^q$ lacZ (M15) Δ(srl-recA)301::Tn10 |
| DY329 | W3110 Δ(argF-lac)U169 nadA::Tn10 gal490 λcI857 Δ(cro-bioA) |
| DY330 | W3110 Δ(argF-lac)U169 gal490 λcI857 Δ(cro-bioA) |
| DY331 | W3110 Δ(argF-lac)U169 Δsrl-recA)301::Tn10 gal490 λcI857 Δ(cro-bioA) |
| DY378 | W3110 λcI857 Δ(cro-bioA) |
| W3110 | "Wild-type" |
| HME5 | Δ(argF-lac)U169 λcI857 Δ(cro-bioA) |
| HME6 | Δ(argF-lac)U169 galK$_{tyr145UAG}$λcI857 Δ(cro-bioA) |
| HME9 | Δ(argF-lac)U169 galK$_{tyr145UAG}$λcI857 Δ(cro-bioA) tyrTV<>cat |
| HME10 | Δ(argF-lac)U169 galK$_{tyr145UAG}$λcI857 Δ(cro-bioA) tyrTV<>cat Δ(srl-recA)301::Tn10 |
| HME31 | Δ(argF-lac)U169 galK><catsacB λcI857 Δ(cro-bioA) |
| HME40 | Δ(argF-lac)U169 INgal[galM$^+$K$_{tyr145UAG}$T$^+$E$^+$] λcI857 Δ(cro-bioA) |
| HME43 | Δ(argF-lac)U169 galK$_{tyr145UAG}$ λ (exo-int)<>cat Δ (gam-N) cI857Δ(cro-bioA) |
| HME47 | galKO34<>kan λexo<>cat cI857Δ(cro-bioA) |
| DY411 | galKO34<>kan λcI857 Δ (cro-bioA) |
| DH10B | F mcrA Δ(mrr-hsdRMS-mcrBC) φ80dlacZΔM15 ΔlacX74 deoR recA1 endA1 araD139 Δ(ara, leu)7649 galU galK rspL nupG |
| DY303 | DH10B [λcI857recA*] |
| DY374 | W3110 gal490 nadA::Tn10 [λcI857 Δ(cro-bioA)] |
| DY363 | W3110 ΔlacU169 gal490 [λcI857 (cro-bioA)<>tet$^a$] |
| DY380 | DH10B [λcI857 (cro-bioA)<>tet] |
| EL11 | DH10B [λcI857 (cro-bioA)<>cat-sacB] |
| EL250 | DH10B [λcI857 (cro-bioA)<>araC-P$_{BAD}$flpe$^b$] |
| EL350 | DH10B [λcI857 (cro-bioA)<>araC-P$_{BAD}$cre] |

$^a$(cro-bioA)<>tet indicates substitution of cro-bioA with tet.
$^b$P$_{BAD}$ represents the promoter of araBAD.

Strain DY329 was constructed by transduction of ZH1141 with P1 phage grown on WJW23, selecting for nadA:Tn10 tetracycline resistance (Tet$^R$) at 32° C. and then screening for the presence of a defective lambda prophage which causes temperature sensitive cell growth at 42° C. Similar P1 transduction was used to create other strains described in Table 2 using standard media, methods, and selections (Sambrook et al., *Molecular Cloning: a Laboratory Manual*, 2$^{nd}$ Ed., (c) 1989; Miller, *Experiments in Molecular Genetics*, Cold Springs Harbor Lab Press, (c) 1972). The symbol <> is used to indicate a replacement generated by homologous recombination. The symbol >< indicates an insertion generated by homologous recombination. A deletion at the point of insertion is indicated in parenthesis following the inserted gene. The entire gal operon in HME40 is inverted (IN).

To induce expression from the pL operon and prepare electroporation-competent cells, overnight cultures grown at 32° C. from isolated colonies were diluted 50-fold in LB medium and were grown at 32° C. with shaking to an OD$_{600}$ of about 0.4–0.8. Induction was performed on a 10 ml culture in a baffled conical flask (50 ml) by placing the flask in a water bath at 42° C. with shaking (200 revolutions/min) for 15 minutes. Immediately after the 15 minute induction, the flask was swirled in an ice water slurry to cool for 10 minutes. An uninduced control culture, maintained at 32° C. throughout, was also placed into the ice slurry. The cooled 10 ml cultures were centrifuged for 8 minutes at 5,500×g at 4° C. Each cell pellet was suspended in 1 ml of ice-cold sterile water, transferred to a 1.5 ml plastic microcentrifuge tube, and was spun for 20 seconds at 4° C. at maximum speed in a microcentrifuge. After washing the cell pellets as described two more times, the cells were suspended in 100 μl of ice cold sterile water. This volume of competent cells is sufficient for two standard electroporation reactions (~10$^8$ cells per reaction). Larger cultures can be prepared for a greater number of reactions or for storage of electrocompetent cells at −80° C. with 12% glycerol present. Fresh competent cells give highest efficiencies of recombination. To transform cells by electroporation, purified linear donor DNA (1 to 10 μl) was mixed with competent cells in a final volume of 50 μl on ice, and then pipetted into a pre-cooled electroporation cuvette (0.1 cm). The amount of donor DNA used per reaction (usually 1 to 100 ng) is indicated for relevant experiments. Electroporation was performed using a Bio-Rad Gene Pulser set at 1.8 kV, 25 μF with Pulse controller of 200 ohms. Two protocols have been used interchangeably to allow segregation of recombinant from parental chromosomes within the electroporated cells. In both protocols, the electroporated cells were immediately diluted with 1 ml of LB medium. In one, the cells were incubated for 1 to 2 hours at 32° C. before selecting for recombinants. In the other, the cells were immediately diluted and spread on sterile nitrocelluose filters (100 mm) on LB agar. After a 2 hour incubation at 32° C., the filters were transferred to the appropriate agar plates required to select for recombinants. Aliquots were also directly spread on LB agar and incubated at 32° C. to determine and examine total viable cells after electroporation. For drug resistant selection, each ml of LB medium contained 10 μg of chloramphenicol, 12.5 μg of tetracycline, 20 μg of kanamycin, 30 μg of ampicillin, or 50 g of spectinomycin.

Although recombinants were verified by more than one method, the primary detection was for an altered phenotype caused by the modified target gene. Disruption or mutation of the galK gene was confirmed by the presence of white colonies on MacConkey galactose indicator agar, disruption of the rnc gene for the endoribonuclease RNaseIII was confirmed by the inability of lambdoid type phage to lysogenize (Court, pp. 71–116 in Belasco et al., eds., *Control of Messenger RNA Stability,* (c) 1993, Academic Press, New York), and deletion of gam, kil, and cIII in the pL operon was scored as an ability of the λ lysogen to survive growth at 42° C. (Court and Oppenheim; Greer, *Virology* 66:589–604, 1975). PCR analysis was used to confirm the altered structure caused by replacement of a gene. Southern hybridization analyses of parental and recombinant DNAs confirmed structural changes, and DNA from the recombinant clones can be amplified by PCR and sequenced.

In addition to electroporation, any suitable method for macromolecular transfer into bacterial cells would be effective for practicing the methods herein disclosed. For example, such methods may include exposure to divalent cations, DMSO and the like as described in a variety of standard laboratory publications, such as Sambrook et al. (see particularly pages 1.74–1.84) and Ausubel et al., eds., *Current Protocols In Molecular Biology,* John Wiley & Sons (c) 1998 (hereinafter Ausubel et al.), herein incorporated in their entirety.

Example 3

Homologous Recombination with Short Linear DNA Fragments

The recombination system described in Examples 1 and 2 were used to generate a single bp mutation in the bacterial galK gene.

The galK gene encodes a galactokinase that phosphorylates galactose and its derivatives. The galK galactokinase phosphorylates 2-deoxygalactose to generate 2-deoxygalactose phosphate (2DGP). While unphosphorylated 2-deoxygalactose has no impact on cell growth, 2DGP is a nonmetabolized sugar phosphate that inhibits cell growth. Thus, cells containing a wild type galK gene grow poorly on 2-deoxygalactose, a phenotype referred to herein as Gal+. In contrast, mutants defective in galK grow well in the presence of 2-deoxygalactose (Dog), and have a phenotype referred to herein as DogR—(Adhya, pages 1503–1512 in *Escherechia coli and Salmonella typhimurium: Cellular and Molecular Biology,* Neihardt et al. eds., American Society of Microbiology, 1987). The DogR-phenotype enables ready selection of cells harboring successful recombination events.

Complementary 70 base pair oligonucleotides were synthesized and annealed to each other. The annealed DNA was homologous to an internal coding segment of the bacterial galK gene, except that a UAU codon (TYR-145) was changed to a UAG amber codon. A homologous recombination event between this 70 base pair DNA fragment and the galK gene introduces a premature stop codon in the galK gene, and is referred to herein as the galK amber mutation. This mutation produces a truncated galK gene product that lacks function.

The 70-bp DNA fragment was transferred by electroporation into galK+ cells (HME5) that had been induced for lambda pL operon expression by growth at 42° C. for 15 minutes. After electroporation with the mutant DNA (100 ng) or mock electroporation without DNA, the cells were spread on minimal 0.4% glycerol agar medium with 0.2% 2-deoxygalactose present. Spontaneous resistant mutants occurred frequently ($10^{-4}$) in the absence of mutant DNA. Despite this, the addition of the mutant DNA enhanced the frequency of resistant mutants dramatically, generating one mutant per 500 electroporated cells.

To determine that temperature induction was required, another batch of cells that had not been induced for recombination function was tested in the same way. In this treatment, no discernable effect of added mutant DNA was observed. This indicated that both induction of pL operon expression and mutant DNA addition were required for the enhanced survival. Without wishing to be bound by a single explanation of the observed effects, it is believed that the expressed lambda functions allowed for efficient recombination of this short linear mutant DNA with the chromosomal galK gene.

Colonies surviving 2-deoxygalactose treatment were screened for their Gal phenotype on indicator plates, and all tested had the Gal—phenotype expected for a galK amber mutant. To test specifically whether the galK amber mutation was present, four independent Gal—colonies were tested by transducing cultures of each with a lambdaimm21 phage that carries the $tRNA_{tyr}$ suppressor allele supF. The four mutants tested were suppressed to a Gal+ phenotype. Finally, the presence of the amber mutation in galK was verified by PCR amplification and sequence analysis of the galK gene segment from the chromosome.

This example demonstrates that controlled expression of lambda recombination genes from a defective lambda prophage promotes surprisingly efficient homologous recombination in bacterial cells, even with short linear segments of DNA having very short homology arms.

Importantly, the high recombination frequency indicates that recombinants were identified without the need to apply positive or negative selection methods. DNA hybridization probes are thus designed to detect point mutations, deletions, insertions or other modifications of cellular DNA. Standard colony hybridization or in situ hybridization techniques can be used to detect cells in which recombination has occurred. Alternatively, enrichment methods for mutation detection are used, particularly for detecting point mutations. Such enrichment methods are described in Gocke et al., *Annals of the New York Academy of Sciences* 906:31–38, 2000, which is herein incorporated by reference in its entirety. One example of a suitable enrichment is the mismatch amplification mutation assay described by Cha et al., *PCR Applications and Methods* 2:14–20, 1992, herein incorporated by reference in its entirety.

The fact that the DNA fragments with short homology arms are able to recombine in vivo opens a vast array of new possibilities for generating recombinant DNA. Several steps normally involved in generating recombinant DNA molecules are eliminated. Restriction enzyme digests are not required to generate DNA fragments, and DNA ligase reactions are not required to join different DNA fragments at novel junctions. The cell generates the completed recombinant precisely joined through homologous recombination.

The efficiency of recombination approaches 0.1% of surviving cells from a standard electroporation. At this efficiency, unselected colonies could be screened for recombinant DNA using colony hybridization techniques, eliminating the need for selection steps. Thus, this recombination protocol makes the bacterial chromosome and plasmid DNA amenable to almost any type of desired change. This includes directed mutagenesis of a gene, a gene segment, or even a base.

Example 4

Preparation of Linear DNA Cassettes Greater than 1000 bp in Length

Standard Polymerase Chain Reaction (PCR) conditions were used to amplify linear DNA fragments with the Expand™ High Fidelity PCR system of Boehringer Mannheim. The chloramphenicol resistant ($Cm^R$) cassette cat was amplified from pPCR-Script Cam (Stratagene) with primers 5'TGTGACGGAAGATCACTTCG (SEQ ID NO: 1) and 5'ACCAGCAATAGACATAAGCG (SEQ ID NO: 2). The tetracycline resistant ($Tet^R$) cassette tet was amplified from Tn10 with primers 5'CTCTTGGGTTATCAAGAGGG (SEQ ID NO: 3) and 5'ACTCGACATCTTGGTTACCG (SEQ ID NO: 4). The ampicillin resistant ($Ap^R$) cassette amp was amplified from pBluescript (Stratagene) with primers 5'CATTCAAATATGTATCCGCTC (SEQ ID NO: 5) and 5'AGAGTTGGTAGCTCTTGATC (SEQ ID NO: 6). The kanamycin resistant cassette kan was amplified from Tn5 with primers 5'TATGGACAGCAAGCGAACCG (SEQ ID NO: 7) and 5'TCAGAAGAACTCGTCAAGAAG (SEQ ID NO: 8). PCR products were purified using Qiagen PCR purification kits and concentrated if necessary by ethanol precipitation. The amplified linear DNAs were suspended in sterile water or TE buffer (10 mM Tris-Cl pH7.5; 1 mM EDTA) and quantified by spectroscopy. DNA in water was stored at −20° C. The inventors avoided PCR product purification schemes from gels in which the DNA is subject to ultraviolet irradiation.

In order to design primers for amplification of a recombination cassette, recombinant oligonucleotides were chemically synthesized with the 5' 30 to 50 nucleotides identical to sequences at the target nucleic acid sequence, and with the 3' 20 nucleotides homologous to the ends of the cassette to be introduced. A cassette is generated by PCR that is flanked by the 30 to 50 base homologies present at the target.

Cells carrying the target DNA either on the chromosome or on a plasmid are induced for Exo, Beta and Gam function. These cells are made competent for electroporation and mixed with the amplified cassette. Following electroporation, recombination occurs between the homologous sequences on the linear cassette and the target replaces the target segment with the cassette.

The 50 nt galK homology segments (rectangles) used for the experiment described in Table 3 are:

Plasmid template DNA can be destroyed by treatment with DpnI following the PCR; DpnI cuts methylated GATC template DNA leaving the newly replicated unmethylated DNA intact. Once a linear cassette has been generated, it can be stored and used as the template for subsequent PCRs.

Example 5

Gene Replacement by Targeted Homologous Recombination

Having demonstrated in Example 3 that 70-bp linear DNA can direct mutations to a specific target, a synthetic DNA having 50-bp galK DNA segments flanking the cat (chloramphenicol resistance, or $Cm^R$) cassette was constructed for targeting a galK gene replacement by cat.

The linear cat cassette with flanking galK DNA was made by PCR using chemically synthesized primers, as described in Example 4.

Data from these experiments are presented in Table 3. DY330 competent cells were electroporated with 100 ng of the cat cassette targeted to replace either galK (galK<>cat) or prophage genes cIII kil gam (cIII kil gam<>cat; see FIG. 1 for map of prophage genes). Total recombinants per electroporation are shown in the rightmost column, "CmR recombinants." The cat cassette was transferred by electroporation into galK+ cells which had either been heat-induced for pL operon expression (15 minute temperature shift to 42° C., as indicated by "15" in the center column of Table 3) or not induced (maintained at 32° C.; indicated by "0" in the center column of Table 3). See also Example 2 for description of induction and other methods. After electroporation, $Cm^R$ recombinants were selected at 32° C., and then quantified.

As shown in Table 3, $Cm^R$ colonies were only found in the heat-induced culture. All 50 $Cm^R$ colonies tested had a Gal-phenotype on MacConkey galactose indicator agar, indicating the presence of the galK<>cat replacement. The symbol <> indicates a replacement generated by homologous recombination techniques, for example, galK<>cat indicates that the bacterial galK gene is replaced by cat using homologous recombination techniques.

```
5'GTTTGCGCGCAGTCAGCGATATCCATTTTCGCGAATCCGGAGTGTAAGAA  (SEQ ID NO: 9)
and

5"TTCATATTGTTCAGCGACAGCTTGCTGTACGGCAGGCACCAGCTCTTCC   (SEQ ID NO: 10)
G
```

In one embodiment, the cassette is a drug resistance marker but can be any DNA if the target sequence in the subsequent steps can be counter-selected. The transcription of the marker cassette has been oriented arbitrarily in the same direction as the target region being replaced. The primers contain two parts: a 5' end homologous to flanking regions of the target DNA, and a 3' end that primes the cassette DNA for replication. The PCR using these primers and a DNA template containing the marker cassette generates a linear DNA product with the cassette flanked by target homology. Note that if transformation with the template DNA will generate the selected phenotype (for example, the template is a plasmid), the template is then eliminated.

TABLE 3

| Target Site* | 42° C., min | $Cm^R$ Recombinants |
|---|---|---|
| GalK | 0 | <1 |
| GalK | 15 | $2.5 \times 10^4$ |
| CIII kil gam | 0 | <1 |
| CIII kil gam | 15 | $5.0 \times 10^4$ |

In similar experiments using the same 50-bp homologous arms, the galK has been exchanged for kan, amp, and tet cassettes by selecting for KM$^R$, Amp$^R$, and Tet$^R$, creating galK< >kan, galK< >amp, and galK< >tet replacements, respectively.

To test whether this approach also works at other positions on the bacterial chromosome, a linear cat cassette was created flanked by 50-bp DNA segments found immediately upstream and downstream of the rnc gene encoding RNaseIII. The rnc gene is thought to be non-essential (Takiff et al., *Journal of Bacteriology* 171:2581–2590, 1989); therefore, it was tested whether an exact substitution of the cat coding region for the rnc coding region (from AUG to codon 224) could be made using the recombination techniques herein described. In this construct, cat is transcribed from the rnc promoter, and the 5' primer used to generate cat started at the cat initiation codon.

Following procedures used for galK as described in Examples 2 and 3, Cm$^R$ colonies were found, but only in the induced culture. The Cm$^R$ colonies tested had a Rnc mutant phenotype, as described in Example 2.

Two other rnc< > cat recombinants were made. One replaced sequence from the AUG start to codon 126 of rnc, and the other from the AUG start to codon 192 of rnc. These two recombinants generate cat: :rnc gene fusions with an mc mutant phenotype. Different sets of primers were chosen to detect unambiguously the wild type and/or recombinant alleles. This PCR procedure follows guidelines set forth by yeast researchers in characterizing chromosomal replacements in yeast (Winzeler et al., *Science* 285: 901–906, 1989). The PCR analysis of the recombinants verified the loss of the rnc+ gene and the predicted structures of the three rnc< > cat gene replacements.

In this example, several different genes on the bacterial chromosome and on plasmids have been substituted with drug resistance markers. However, it is also possible to create recombinants in which the desired product does not include a selectable marker. Genes have been fused to cassettes encoding specific tags such as the green fluorescent protein. Fusion tags can be placed precisely in the gene to be modified, for example, by any of the following strategies. In one, the unselected cassette is joined to a selectable drug marker, and both are recombined into the chosen location selecting for drug resistance. In another, the cassette is recombined into its location by substituting it for a negative selection marker like sacB (Bloomfield et al., *Mol Microbiol* 5:1447–57, 1991). This strategy permits cloning of any DNA. In a third strategy, the recombinants are screened non-selectively by DNA hybridization with probes specific to the cassette.

In these experiments, the desired recombination product was usually obtained. However, some recombination products were unexpected. In two cases, an attempt was made to knockout essential genes, and surprisingly it was possible to select a few rare recombinants. These turned out to be diploid for the region of the targeted gene, since they carried the wild type and the mutant copy of the gene as determined by PCR analysis. Rare diploid regions of the bacterial chromosome are known to occur spontaneously in growing cells at a frequency of about 0.1% (Haack and Roth, *Genetics* 14:1245–1252, 1995). Because an essential gene was targeted, these rare diploids were selected. This was only possible because the recombination is so efficient.

This example demonstrates that the methods of this invention can be used to promote efficient gene replacement by homologous recombination. The gene replacements were made throughout the bacterial chromosome. In Example 7, it is shown that the methods can be used to modify extra-chromosomal nucleic acids, such as plasmids, bacterial artificial chromosomes, cosmids, phagemids, and the like.

Example 6

Induction Time, DNA Amount, and Homology Arm Length Affect Targeting Efficiency

Induction time. FIG. 3 shows the effect of induction time on recombination. The strain DY330 was grown at 32° C. to $OD_{600}$=0.4 to 0.8, heat-induced at 42° C. for the times indicated and then made electrocompetent (see Example 2 for description of methods). A linear cat cassette (10 ng) was used to target the cIII kil gam genes of the prophage. Total Cm$^R$ recombinants were plotted versus the time of induction.

Induction of pL operon expression for only five minutes enhanced recombination activity. FIG. 3 reveals that by 7.5 minutes of heat induction a maximum efficiency is reached. This maximum level is maintained for induction times from 7.5 to 17.5 minutes with some reduction occurring for times longer than 17.5 minutes. Expression of the pL operon for longer than 60 minutes causes cell death.

Cells harboring the defective lambda prophage may be grown at temperatures other than 32° C. In general, it is undesirable to grow cells at temperatures >37° C., because such temperatures lead to partial inactivation of the cI repressor, and leaky expression from the pL promoter. In general, it is also undesirable to grow cells at temperatures below 20° C., because of slow growth. One skilled in the art would also recognize that there is a considerable degree of latitude with regard to time and temperature of induction. For example, expression of lambda recombination genes from the pL operon could be induced at temperatures as low as 38° C., generally allowing for longer times of induction. The limit for protein expression in *E. coli* is about 45° C.

Figure 4:
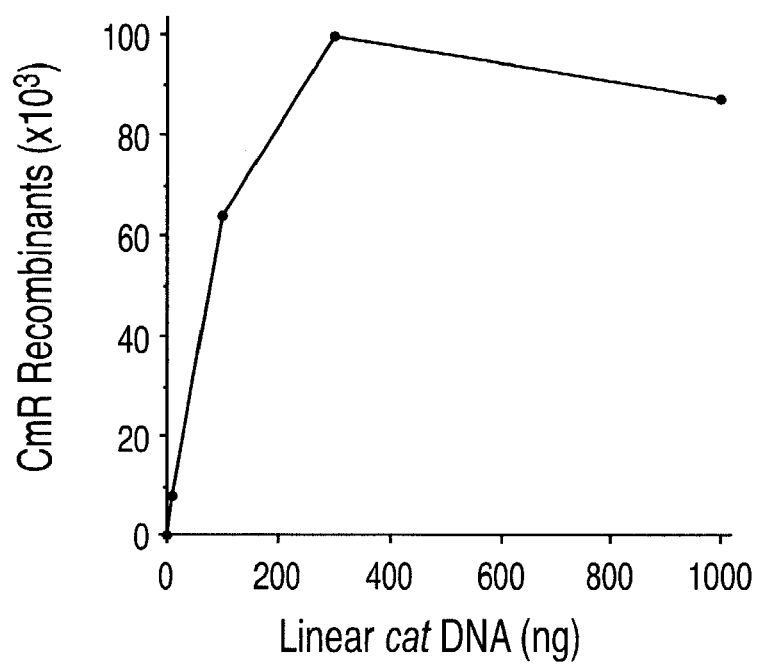
FIG. 4 is a graph that shows the effect of linear DNA amount on recombination. The $E.$ $Coli$ strain DY330 was induced at 42° C. for 15 minutes, and DNA encoding a linear chloramphenicol resistance cassette (<cat>) at the indicated concentration was electroporated into cells. DNA concentration encoding <cat> is plotted on the x-axis, against number of chloramphenicol-resistant recombinants obtained on the y-axis.

Donor DNA amount. FIG. 4 shows the effect of amount of the linear DNA cassette on recombination. The strain DY330 was grown at 32° C. to $OD_{600}$=0.4 to 0.8, induced at 42° C. for 15 minutes and then made electrocompetent. Different amounts (1, 10, 100, 300, 1,000 ng) of a linear cat cassette (1 kbp in length) were used to target the cIII kil gam genes of the prophage. Total Cm$^R$ recombinants were plotted versus the DNA amount at 42° C.

FIG. 4 shows that targeting efficiency increased in a near linear relationship with increasing concentration of donor DNA in the range from $10^8$ (1 ng) to $10^{10}$ (100 ng) molecules per electroporation. A saturating level of linear DNA is reached at $3 \times 10^{10}$ molecules yielding $7.5 \times 10^4$ recombinants per ~$2 \times 10^8$ cells electroporated. Thus, the methods of this invention may be practiced over a broad range of oligonucleotide concentrations.

Figure 5:
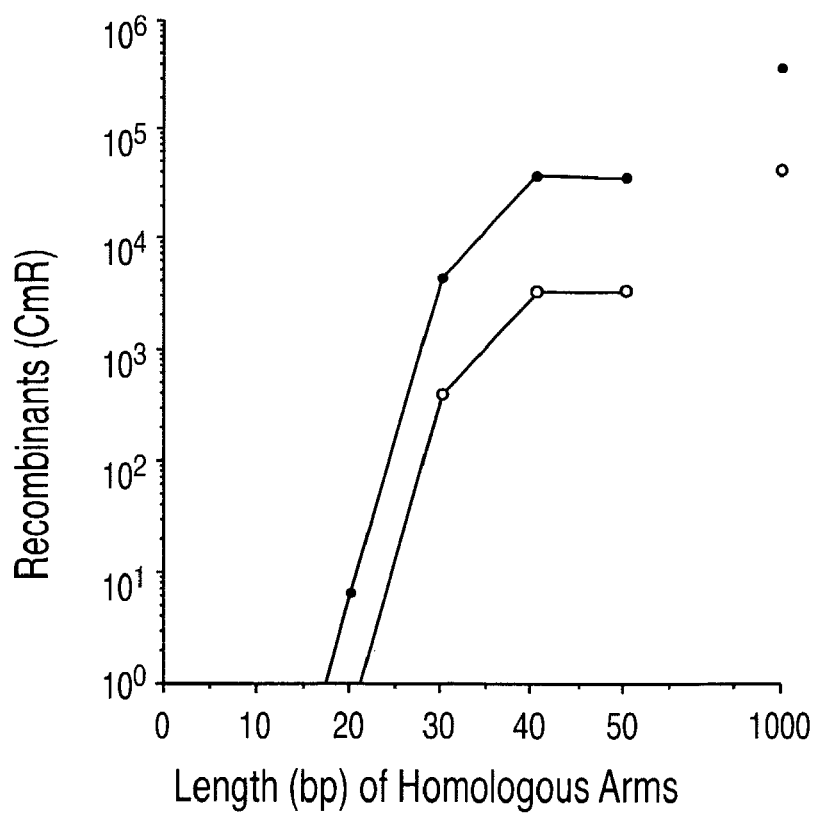
FIG. 5 is a graph which shows the effect of homologous arm length on recombination in $E.$ $coli$ cells induced for expression of lambda recombination proteins Beta, Exo, and Gam. A chloramphenicol resistance cassette was synthesized with homologous arms of the indicated length at its 5' and 3' end. Homologous arm length was varied from 0 to 1,000 base pairs. Length of homologous arms is plotted on the x-axis, against number of chloramphenicol-resistant recombinants (log scale) on the y-axis.

Homology length. FIG. 5 shows the effect of homologous arm length on recombination. The strains DY330 (recA+) (filled circles) and DY331 (recA−)(open circles) were grown at 32° C., induced at 42° C. for 15 minutes and then made electrocompetent. A linear cat cassette (100 ng) was used to target the cIII kil gam genes of the prophage. The homologous arm length of the cassette was varied from 0 to 1,000 bp. The primers containing the 0 to 50 bp homologies were chemically synthesized as described (FIG. 2). The cassette containing 1,000 bp homologous arms was made by PCR using primers 1,000 bp away on each side of an existing (cIII kil gam)<>cat disruption in the cell. Total Cm$^R$ recombinants were plotted versus the homologous arm length.

Several pairs of primers were made to amplify the cat cassette for targeting the chromosome and designed each pair with a different length of flanking homology. The length of the homology segment on the primers varied by increments of 10 bases from 10 to 50 bases. A nested set of linear cat cassettes was made with the primers. Another linear cat cassette was constructed flanked by 1,000 bp of homology. This set of linear DNAs was then tested for recombinational targeting efficiency as shown in FIG. 5. No recombinants were found with 10 bp of homology and less than ten recombinants were found in each of three experiments with 20 bp of homology. From 20 bp to 40 bp of homology, homologous recombination increased by four orders of magnitude. From 40 bp to 1,000 bp of homology, recombination increased 10-fold.

These data indicate that the methods herein disclosed may be practiced with surprisingly short homology arms, as few as 20–40 residues. However, homology arms of 30 or greater residues increase efficiency.

Example 7

Gene Replacement on Plasmids and BACs: in vivo Cloning

To determine if this method could be used to modify plasmid DNA, the procedures described in Examples 2–3 were followed to modify plasmid pGB2, a derivative of pSC101 (Bernardi et al., *Nucleic Acids Res.* 12:9415–9426, 1984). A cat cassette was synthesized in vitro and recombined in vivo with pGB2 to replace the spectinomycin resistance gene with cat conferring $Cm^R$ on the cell carrying the recombinant plasmid.

The same experiment, performed on pBR322 derivatives, generated recombinants, but they were joined in tandem to non-recombinant plasmids as dimers and higher multimers. Induction of Gam expression from our prophage inactivates RecBCD nuclease. In the absence of RecBCD, pBR322 derivatives replicate by a rolling circle mode (Feiss et al, *Gene* 17:123–130, 1982), and the plasmid converts from monomers to multimers. This is specific for pBR322-type replicons as the pGB2 type did not form multimers.

To generate simple recombinants of pBR322 derivatives, the protocol was modified by coelectroporating the recA⁻ strain DY331 with circular plasmid DNA (0.1 ng) and a linear drug cassette. Recombinant plasmid monomers were readily selected and isolated.

In addition to plasmids, the method is also suitable for targeting genes on bacterial artificial chromosomes, phagemid artificial chromosomes, yeast artificial chromosomes, cosmids, and the like. Homologous recombination between target nucleic acid sequences on BACs and synthetic oligonucleotides (such as ds DNA fragments or PCR fragments) is carried out in bacterial cells bearing the defective lambda prophage shown in FIG. 1 and described in Example 1. Synthetic oligonucleotides (such as short annealed dsDNA fragments or PCR fragments) are electroporated into bacterial cells as described in Example 2. Analysis for successful recombination events is by selective PCR amplification using specific primers for the introduced sequence, or by selective amplification approaches such as the mismatch amplification mutation assay described by Cha et al., *PCR Applications and Methods* 2:14–20, 1992, or by direct hybridization using specific probes. Using this approach recombination frequencies of up to 1:500 have been observed, regardless of the strand targeted. Thus, this system is extremely useful in manipulation of and rapid screening for recombinants in BAC vectors. The unexpectedly high efficiencies eliminate the need for introducing selectable markers, or modifying such markers on the BAC.

Example 8

Requirement of RecA for Targeted Recombination

The requirement for RecA were tested in targeted homologous recombination by repeating the experiment described in FIG. 5 but using a recA⁻ strain. Surprisingly, recombination efficiency was depressed only about 10-fold in the recA–mutant for the arm lengths tested (FIG. 5). Thus, RecA function is not required, and recA–strains mediate efficient homologous recombination with linear DNA fragments having homology arms of 30 bp or greater.

This result was unexpected. The λ recombination system is known to function in cells lacking the bacterial RecA function (Brooks and Clark, *J. Virol.* 1:283–293, 1967). However, the recombination in recA mutants under conditions used by others is reduced more than 50-fold relative to levels in recA⁺ cells (Stahl et al., *Genetics* 77:395–408, 1974; Murphy, *J. Bacteriol.* 180:2063–2071, 1998).

Example 9

Lambda Genes Promote Targeted Recombination of dsDNA in Wild Type *E. coli*

To determine which lambda genes promote targeted recombination of dsDNA, a set of replacement deletions were generated in the pL operon of the prophage using cat and amp cassettes. In the center column of Table 4, the parentheses indicate the deletions made by the recombination event within the prophage (refer to FIG. 1 for a linear map of the prophage genes). Each of these newly made deletions was verified structurally by PCR analysis and tested for targeted recombination of a tet gene cassette into galK.

Electrocompetent cells from strains indicated in Table 4 were heat-induced for 15 minutes at 42° C., and electroporated with 10 ng of linear galK<>tet. The results are presented as total number of $Tet^R$ recombinants per electroporation in the right hand column of Table 4.

TABLE 4

| Strain | Prophage | Recombinant |
| --- | --- | --- |
| DY330 | wild-type | 4,100 |
| DY392 | (hin-int)<>amp | 2,000 |
| DY351 | (sieB-kil)<>cat | 4,400 |
| DY386 | (hin-int)<>amp (sieB-kil)<>cat | 1,650 |
| DY349 | (gam)<>cat | 0 |
| DY360 | (bet)<>cat | 0 |
| DY359 | (exo)<>cat | 0 |

Table 4 shows that only exo, bet, and gam deletions affected galK<>tet targeted recombination. Deletion of any one of these three genes eliminated the recombination, whereas deletion of all other genes in the pL operon had little if any effect.

To show that the gam<>cat substitution was not polar on bet and exo, the gam gene was expressed in trans and shown to complement the defect. Thus, although the entire pL operon was used in studies described here, only exo bet and gam functions are needed for recombination with double-stranded DNA cassettes >100–200 bp made by PCR.

Example 10

Efficient Recombination with Single-Strand DNA

To evaluate recombination between exogenous single-strand DNA and the *E. coli* chromosome, the experiments described in this Example were performed. In addition, the experiments also address the role of the bacterial recA recombination genes in mediating the observed effects.

Expression from the pL operon was heat-induced, cells were made electroporation-competent, and 70-mer oligonucleotides were electroporated into cells, all as described in Example 2. Strains HME9 and HME10 both harbor the galK amber mutation, and are therefore Gal-in phenotype. They differ from each other in that HME9 is recA+, whereas HME10 is recA−. Thus in this experiment recombination efficiencies in recA+ and recA−cells are compared.

The 70-mer single-stranded oligonucleotides used in this experiment were designed to restore wild type galK gene activity (hereinafter galK+) upon successful recombination, thereby producing a Gal+ phenotype (i.e., ability to grow on minimal media with galactose as the sole carbon source). The 70-mer corresponding to the transcriptional non-template DNA strand of galK was 5'AAGTCGCGGTCG-GAACCGTATTGCAGCAGCTTTATCATCTGCCGCTGG ACGGCGCACAAATCGCGCTTAA (SEQ ID NO: 11).

70-mer single-stranded DNA of either SEQ ID NO: 11 or its complement was electroporated into cells. Alternatively, the two 70-mers were first annealed to each other and then electroporated into cells as double strand DNA. A successful recombination event was identified by restoration of the Gal+ phenotype. Table 5 indicates the number of galK+ recombinants per viable cell, ×10$^{-4}$.

Table 5 presents the number of recombinants observed ×10$^{-4}$ after electroporation of the HME9 or HME10 strains with DNA in the indicated forms. Efficient recombination was observed with double strand DNA, similar to that previously described in Examples 3 and 5. Surprisingly, single-strand DNA was about equally or even more efficient than double-stranded DNA in producing homologous recombination, regardless of strand used. In this experiment, recombination efficiencies for the double-stranded DNA was about 1 in 3800 cells (2.6–2.7×10$^{-4}$), whereas recombination efficiency for single-stranded counterclockwise DNA was 3- to 7-fold higher. In other strains (e.g. DY374) recombination of single strand linear DNA as frequent as one nadA$^+$ recombinant per 20 viable cells has been observed. In addition, efficient recombination was observed in both recA+ and recA− cells, establishing that the recombination events did not require the bacterial recA gene products.

TABLE 5

| | DNA used in electroporation | | |
|---|---|---|---|
| Strain Used | dsDNA (about 1 µg) | cc-ssDNA (about 0.7 µg) | cw-ssDNA (about 0.6 µg) |
| HME9 galK$^{am}$λCI857Δ(cro-bio) | 2.6 | 18.5 | 2.2 |
| HME10 galK$^{am}$λCI857Δ(cro-bio) recA$^-$ | 2.7 | 9 | 0.35 | cc = clockwise (strand with the 5' to 3' orientation relative to transcription)
cw = counterclockwise (strand with the 3' to 5' orientation)

Example 11

Efficient Generation of Large Deletions by Recombination with Single-strand DNA Example 10 demonstrates efficient lambda-mediated recombination using ssDNA to generate a single base change in the *E. coli* chromosome. This example demonstrates similar high efficiency when the approach is used to generate large deletions.

Using the methods described in Examples 2, 3, and 10, lambda operon expression was heat-induced, cells were rendered electroporation-competent, and 70-mer single-stranded DNA of either SEQ ID NO: 11 or its complement was electroporated into cells. The DNA was electroporated into two strains: one containing the galK amber mutation, and one in which the galK gene was interrupted by a cat-sacB cassette precisely inserted at the position of the amber mutation in galK. The strains were otherwise genetically identical. A successful recombination event was identified by restoration of the Gal+ phenotype. Table 6 indicates the number of galK+ recombinants per viable cell, ×10$^{-4}$.

The data in Table 6 demonstrate that recombination efficiency is similar using the same oligonucleotide, regardless of whether lambda-mediated ssDNA recombination is being used to generate a single base change or a large deletion, removal of the 3264 bp cat-sacB cassette. In both cases, the method is highly efficient in generating recombinants.

TABLE 6

| | DNA used in electroporation | |
|---|---|---|
| Strain Used | cc-ssDNA (200 ng) | cw-ssDNA (200 ng) |
| HME6 galK$^{am}$λCI857Δ(cro-bio) | 15 | 3 |
| HME31 galK<>catsacB λCI857Δ(cro-bio) | 10 | 0.5 |

Figure 14:
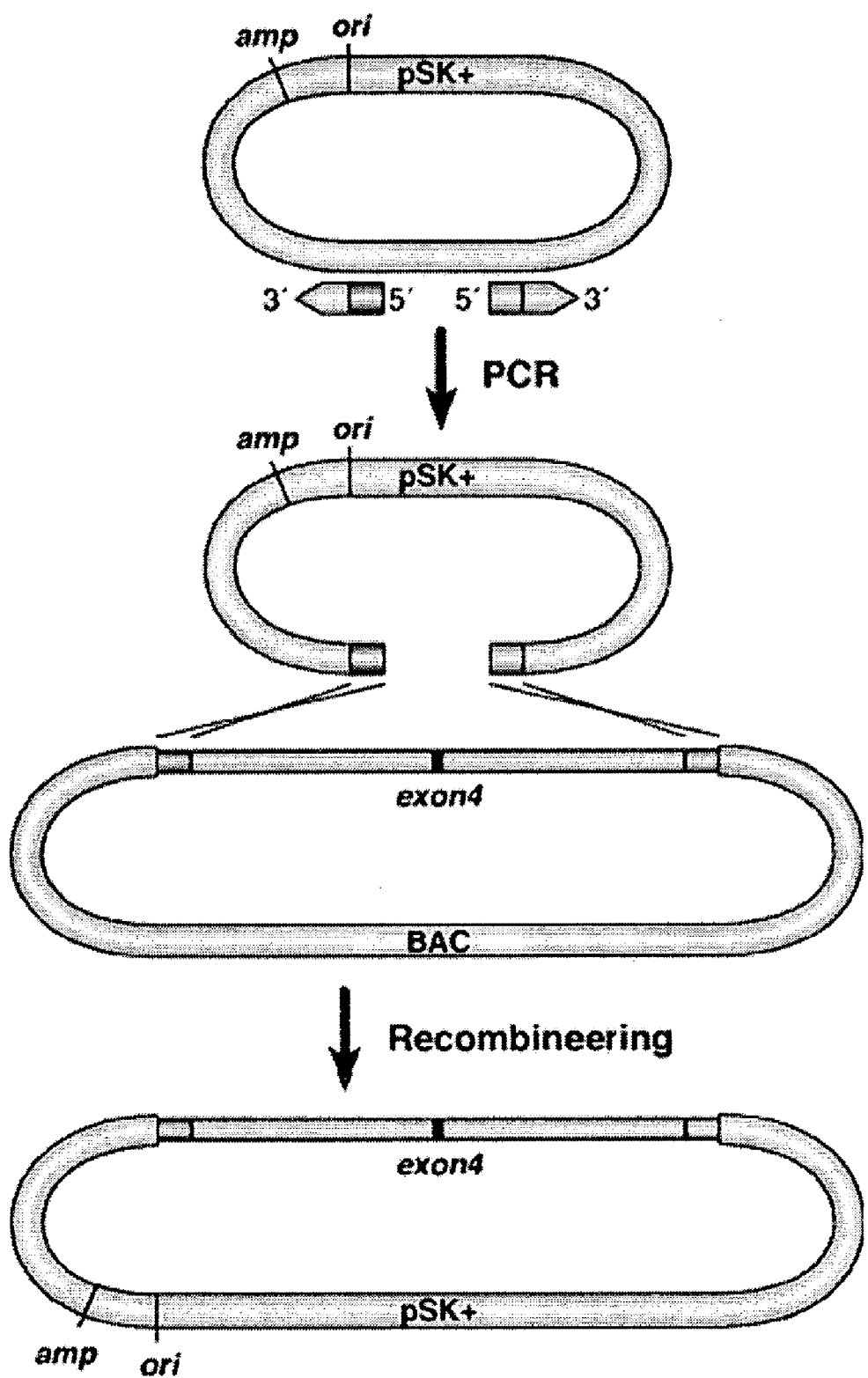
FIG. 14 is a schematic diagram of subcloning a DNA fragment from a BAC into pBluescript (pSK$^+$) by gap repair with short homology arms via recombineering. Primers that have 20 bp of homology (arrows) to pBluescript (circle) at their 3' end, and 50 bp (dark area) of homology at their 5' ends to one of two ends of the BAC DNA to be subcloned (thinner areas, exon 4 in center), are used to amplify pBluescript. The PCR-amplified, linearized, pBluescript containing the two homology arms is then transformed into recombination-competent cells that carry the BAC. Gap-repaired plasmids are selected by their ampicillin resistance. The black bar denotes the location of Evi9 exon 4.

The length that is reasonable to synthesize chemically limits the length of single strand oligonucleotides used for recombination. It is demonstrated herein that two oligonucleotides that have a complementary overlap region at their 3' ends, when co-electroporated into DY411 cells, can anneal and generate recombinants with chromosomal or extrachromosomal DNA (FIG. 14). This recombination requires the induction of the pL operon and the Gam, Beta, and Exo functions. A galK mutation in which the kan cassette was placed in galK in a way to delete 34 bp of the galK gene was created by recombineering. Two oligos were synthesized that were 70 bases long, with 34 bases of the deleted region at their 3' ends, that were complementary and can act to anneal the two oligos together. The 5' end of each oligo contained 36 bases of homology to each side of the 34 bp deletion caused by kan. Each oligo alone cannot generate gal+ recombinants but mixed together they generated up to 10$^5$ recombinants per 10$^8$ cells electroporated. Oligos with the same sequence but shortened from their 3' end to overlap by only 2 bases did not yield recombinants. However, overlaps of 10 bases or more generated recombinants. Pre-annealing was not required and the two oligos can be mixed and used directly for electroporation.

If the ends of the overlaps are filled in by DNA polymerase a 104 bp duplex is generated. This dsDNA generates only slightly more recombinants then the DNA with 10 to 34 base overhangs. Thus, multiple overlapping (by >10 bases) oligonucleotides of any even number can be used to yeild recombinants, in which the most outside oligonucleotides have 5' overlaps. The end oligonucleotides also have 30–50 bases of homology to the targeted region. The use of multiple overlapping oligonucleotides allows production of long recombination substrates without use of PCR. The central oligonucleotide(s) can be any cassette envisioned to be used for dsDNA recombination. This recombination with overlapping oligonucleotides having outside 5' overhangs is most efficient with Exo, Beta, and Gam, but can be recombined by Beta alone (without Exo and Gam) in the cell. This greatly simplifies the recombination procedure (as only Beta is required). Although the 104 bp duplex DNA recombines more efficiently if Exo, Beta and Gam are present, recombination also occurs in the absence of Gam, albeit at a lower efficiency (the duplex requires both Exo and Beta for recombination).

Similar overlapping synthetic oligonucleotides can be generated with 3' overhangs of 34 bases that can be coelectroporated into cells. These are also recombined into targets defined by homology at the ends. Again, only Beta is required for this recombination. In this case, Exo is not required, and further Exo does not stimulate recombination. In one embodiment, multiple oligonucleotides can be overlapped as above to span longer distance. As long as the outermost oligonucleotides have 3' overhangs, recombination will be Exo independent. The efficiencies of the present system allows the detection of recombinants in this case.

Examples 10 and 11, taken together, document that the methods disclosed herein can be practiced with ssDNA oligonucleotides. This surprising result enables high efficiency homologous recombination with synthetic DNA of single or double strandedness.

The present system allows the limit of synthetic oligonucleotide size to be increased dramatically by overlapping oligonucleotides. In addition, the system allows recombination of these DNAs to be carried out with Beta alone, or Exo with Beta but without Gam. Recombination without the requirement for Gam is important because Gam is the toxic function that was a limiting factor in the previously described methods. As the present system requires only Beta, a constitutive promoter can be utilized.

Example 12

Effect of ssDNA Length on Recombination Efficiency

In Examples 10 and 11, lambda-mediated recombination was used to efficiently incorporate 70-mer ssDNAs into the *E. coli* chromosome. In this example, the effect of oligonucleotide length on recombination efficiency was investigated.

Using the methods described in Examples 2, 3, 5, 10 and 11, lambda operon expression was heat-induced, cells were rendered electroporation-competent, and ssDNA oligonucleotides (200 ng each) were electroporated into *E. coli* HME9 strain cells. The electroporated ssDNA oligonucleotides included the 70-mer of SEQ ID NO: 11, a 60-mer constructed by removing the last 5 nucleotides from both the 5' and 3' ends of SEQ ID NO: 11, and a 50-mer, 40-mer, 30-mer, or 20-mer constructed by removing the last 10, 15, 20, or 25 nucleotides, respectively, from both the 5' and 3' ends of SEQ ID NO: 11. As in example 10, the ssDNA oligonucleotides used in this experiment were all designed to restore the galK+ gene upon successful recombination, thereby conferring upon the cell a Gal+ phenotype. Table 7 indicates the number of galK+ recombinants per viable cell, ×$10^{-4}$.

TABLE 7

| | 11/22 Oligonucleotide length | | | | | | |
|---|---|---|---|---|---|---|---|
| | 0 | 20 | 30 | 40 | 50 | 60 | 70 |
| Efficiency (×$10^{-4}$) | 0.004 | 0.01 | 0.47 | 4 | 4 | 6 | 22 |

As the data in Table 7 demonstrate, recombination efficiency increases with increasing ssDNA length. Recombination efficiency was low when the ssDNA used was a 20-mer, but increased considerably with a 30-mer. Efficiency was near optimal with a 40-mer, and increased to 1 in 450 viable cells with a 70-mer. Hence, specific examples of the invention use single-stranded DNA molecules at least about 40 nucleotides in length.

Without wishing to be bound by a single explanation of the observed effects, the inventors currently believe that observed length-efficiency relationship may reflect published data indicating that lambda Beta protein binds stably to DNA sequences of 36 bases or longer, but does not bind as well to shorter oligonucleotides (Mythili et al,, *Gene* 182:81–87, 1996).

Example 13

Lambda Beta Protein Mediates Efficient Recombination with ssDNA

To determine whether lambda Beta protein was sufficient to mediate recombination between exogenous ssDNA and the *E. coli* chromosome, the efficiency of recombination was investigated in a strain that expressed lambda Beta, but not Exo or Gam.

For these experiments, the HME43 strain was used. Its genotype is identical to the HME6 strain, except that the lambda prophage contains additional genetic deletions, from int through exo and from gam through N (see FIG. 1). In addition, the cat gene conferring the CmR phenotype is inserted between attL and bet.

Using the methods described in Examples 2, 3, and 10–12, expression of the modified lambda operon was heat-induced, cells were rendered electroporation-competent, and 70-mer ssDNA of SEQ ID NO: 11 (200 ng) was electroporated into cells. Using this procedure, the HME43 strain expresses lambda Beta protein, but does not express gam, exo, or any other prophage encoded genes. A successful recombination event was identified by restoration of the Gal+ phenotype. Table 8 indicates the number of galK+ recombinants per viable cell, ×$10^{-4}$.

TABLE 8

| Strain | Prophage Modifications | Recombination Efficiency (×$10^{-4}$) |
|---|---|---|
| HME43 | (int-exo)<>cat, (gam-N)<>Δ | 7.7 |

In contrast to Example 9 using PCR-generated double-stranded DNA, the data presented in this example establish that lambda Beta alone is sufficient to mediate efficient recombination between ssDNA and the *E. coli* chromosome. Moreover, two or more overlapping oligonucleotides may be used, if they have a 3' overhang and more than about 10 bp of overlap. Overlapping oligonucleotides with a 5' overhang also promote homologous recombination with Beta alone. However, for 5' overhangs, exo and gam (or a similar exonuclease and RecBCD-inhibition function) appear to enhance maximal efficiency.

A modification of the method is to place DNA encoding other ssDNA binding polypeptides under control of the pL promoter. For example, the strain HME43 is further modified to delete bet and insert DNA encoding P22 Erf, RecT, or Rad52. Expression of the ssDNA binding polypeptide is induced by temperature shift as it is for induction of lambda bet expression. Exo and Gam, or proteins with similar function, can also be placed under control of the pL promoter. Moreover, other inducible or constituitive promoters can be used.

Example 14

Ex Vivo Combination of ssDNA with Lambda Beta Mediates Efficient Homologous Recombination Single-strand DNA can be combined with lambda Beta protein prior to electroporation into cells, and mediated efficient recombination between the ssDNA and the host DNA.

Lambda Beta proteins may be prepared by techniques known in the art (Karakousis et al., *J. Mol. Biol.* 276: 721–731, 1998), and preincubated at 37° C. with single-strand oligonucleotides of 20-mer or greater length. In this example, ssDNA oligonucleotides of SEQ ID NO: 11, a 60-mer constructed by removing the last 5 nucleotides from both the 5' and 3' ends of SEQ ID NO: 11, and a 50-mer constructed by removing the last 10 nucleotides from both the 5' and 3' ends of SEQ ID NO: 11 were used. Typically, lambda Beta protein concentration is about 2.5 µM and DNA concentration about 5 µM, but the method is effective with a broad range of protein and DNA concentrations (for example, from 0.1 µM to 10 mM protein, and 0.01 µM to 10 mM ssDNA). Alternatively, the Beta protein and ssDNA can be coelectroporated into cells without premixture or preincubation.

The DNA and protein is electoporated into *E. coli* using methods described in Examples 2 and 3. In this example HME 43 strain is used, but numerous other strains are suitable. Expression of the modified lambda operon is one set of cells is heat-induced, and a second set of cells is maintained at 32° C. Both sets of cells are rendered electroporation-competent, and 70-mer ssDNA of SEQ ID NO: 11 (200 ng) is electroporated into both heat-induced and uninduced cells. Using this procedure, the HME43 strain expresses lambda Beta protein upon temperature shift to 42° C., but does not express Beta from bet or any other prophage-encoded genes in the absence of a temperature shift. A successful recombination event is identified by restoration of the Gal+ phenotype.

In this experiment, high efficiency recombination is observed in both heat-induced and uninduced cells. Moreover, it is believed that approximately equally high efficiency recombination is observed when these techniques are followed in *E. coli* strains that contain no lambda prophage genes.

This approach can be modified by substituting other ssDNA binding polypeptides for lambda Beta, such as p22 Erf, RecT and Rad52. The target nucleic acid sequence may be on the bacterial chromosome, or on exogenous DNA such as a bacterial artificial chromosome, phagemid artificial chromosome, plasmid, cosmid, or the like. Moreover, there is no particular requirement for a specific bacterial species; these single-strand DNA binding polypeptides will mediate efficient recombination in a broad range of bacteria. Indeed, these polypeptides will mediate efficient recombination in eukaryotic cells as well, as in Example 15.

Example 15

Lambda Beta Protein Mediates Efficient Homologous Recombination in Eukaryotic Cells The ex vivo approach described in Example 14 may be used to target genes in eukaryotic cells for homologous recombination. In eukaryotic cells, transfection of the ssDNA with lambda Beta protein may be accomplished by electroporation as in Examples 2, 3 and 14, or by the methods of Chang et al., *Biochimica et Biophysica Acta*, 153–160, 1992, Keating and Toneguzzo, *Bone Marrow Purging and Processing*, 491–498, 1990, or other electroporation protocols known in the art. In addition, a variety of means for macromolecular transfer methods are known to the art, including calcium phosphate-DNA co-precipitation (Ausubel et al.), DEAE-dextran-mediated transfection (Matthews et al., *Experimental Hematology* 21:697–702, 1993) polybrene-mediated transfection (Costello et al., *Gene Therapy* 7:596–604, 2000), microinjection (Davis et al., *Blood* 95:437–44, 2000), liposome fusion and lipofection (Veit et al., *Cardiovascular Research* 43:808–22, 1999), protoplast fusion (Schaffner, *Proc. Natl. Acad. Sci. U.S.A.* 77:2163, 1980), inactivated adenovirus-mediated transfer (Wagner et al., *Proc Natl Acad Sci U.S.A.* 89:6099–6103, 1992), hemagglutin virus of Japan-(HVJ)-mediated transfer (Morishita et al., *Journal of Clinical Investigation* 93:1458–1464, 1994), biolistics (particle bombardment) and the like. Any such macromolecular transfer approach is suitable. Design of dsDNA molecules for facilitating homologous recombination with eukaryotic genes is well known in the art (for example, as described in Mansour, *Nature* 336:348–352, 1988; Shesely, *PNAS* 88:4294–4298, 1991; Capecchi, M. R., *Trends in Genetics* 5:70–76, 1989; U.S. Pat. No. 6,063,630).

Cells to be transfected with exogenous DNA are combined with a DNA construct comprising the exogenous DNA, targeting DNA sequences and, optionally, DNA encoding one or more selectable markers. The resulting combination is treated in such a manner that the DNA construct enters the cells. This is accomplished by subjecting the combination to electroporation, microinjection, or other method of introducing DNA into vertebrate cells. Once in the cell, the exogenous ssDNA is integrated into cellular DNA by homologous recombination between DNA sequences in the DNA construct and DNA sequences in the cellular DNA.

For example, the target nucleic acid is the beta-globin gene in hematopoietic stem cells from a patient with sickle cell anemia (Beutler, Disorders of Hemoglobin, Ch. 107 in Harrison's Principles of Internal Medicine, 14$^{th}$ ed. © 1998, herein incorporated by reference). The sickle cell Beta globin gene harbors a point mutation that substitutes a Val for Glu at position six of the polypeptide chain, resulting in an abnormal hemoglobin which is prone to inappropriate polymerization. The methods of this invention can be used to correct the mutation.

Hematopoetic stem cells from a sickle cell patient are isolated, cultured, and expanded ex vivo as is known in the art (Brugger, *Seminars in Hematology* 37[1 Suppl 2]:42–49, 2000; Dao et al., *Blood* 92:4612–21, 1998; Aglietta et al., Haematologica 83:824–48, 1998; Emerson, *Blood* 87:3082–8, 1996). A 60-mer ssDNA oligonucleotide of SEQ ID NO: 12 (AACAGACACC ATGGTGCACC TGACTC-CTGA GGAGAAGTCT GCCGTTACTG CCCTGTGGGG) is synthesized and partially purified by standard techniques (Pfleiderer et al., *Acta Biochimica Polonica* 43:37–44, 1996; Anderson et al., *Applied Biochemistry & Biotechnology* 54:19–42, 1995, herein incorporated by reference).

After culture and ex vivo expansion, about $10^6$ hematopoetic stem cells are suspended in 0.4 mL PBS containing 0.1% glucose, about 10 µM purified lambda Beta protein, and about 1 µg ssDNA oligonucleotide of SEQ ID NO: 12. The cell suspension is electroporated in a 1-mL cuvette at 280V and 250 µF with a Gene Pulser (Bio-Rad Laboratories Inc., Hercules, Calif., USA). Cells are then plated and cultured. Homologous recombinants harboring the mutation are identified and clonally isolated, further expanded ex vivo, and may be returned to the patient, or cultured for additional in vitro study.

Those skilled in the art will recognize that a broad range of ssDNA and ssDNA binding polypeptide concentrations will be effective, as in Example 14. For example, both ssDNA and ssDNA binding protein may be present in concentrations ranging from 0.001 µM to 100 mM; or from 0.1 mM to 1 µM; or from 1 µM to 100 µM. Oligonucleotide length can be varied in accordance with parameters presented in Example 12. There is no particular upper limit on oligonucleotide length. In addition, two or more oligonucleotides can be included which have complementary 5' ends, thereby creating 3' overhangs which are effective substrates for ssDNA binding polypeptides such as lambda Beta. In addition, RecT, P22 Erf, Rad52, and other double strand break repair ssDNA binding polypeptides may be substituted for lambda Beta. Culture and electroporation conditions are readily variable without materially reducing homologous recombination. Moreover, nucleic acid may be introduced into the cell by any suitable macromolecular transfer method.

Other types of stem cells can be used to correct the specific gene defects associated with cells derived from such stem cells. Such other stem cells include epithelial, liver, lung, muscle, endothelial, mesenchymal, neural and bone stem cells.

Alternatively, certain disease states can be treated by modifying the genome of cells in a way that does not correct a genetic defect per se but provides for the supplementation of the gene product of a defective gene. For example, endothelial cells can be used as targets for human gene therapy to treat disorders affecting factors normally present in the systemic circulation. In model studies using both dogs and pigs endothelial cells have been shown to form primary cultures, to be transformable with DNA in culture, and to be capable of expressing a transgene upon re-implantation in arterial grafts into the host organism (Wilson et al., *Science* 244:1344, 1989; Nabel et al., *Science* 244:1342, 1989). Since endothelial cells form an integral part of the graft, such transformed cells can be used to produce proteins to be secreted into the circulatory system and thus serve as therapeutic agents in the treatment of genetic disorders affecting circulating factors. Examples of such diseases include insulin-deficient diabetes, alpha-1-antitrypsin deficiency, and hemophilia. Epithelial cells, myocytes and hepatocytes are also useful cell types for therapeutic production of proteins.

The method is also useful for knockout or modification of genes in embryonic stem (ES) cells. Such cells have been manipulated to introduce transgenes. ES cells are obtained from pre-implantation embryos cultured in vitro (Evans et al., *Nature* 292:154–156, 1981; Bradley et al., *Nature* 309:255–258, 1984; Gossler et al., *Proc. Natl. Acad. Sci. U.S.A.* 83:9065–9069, 1986; Robertson et al., *Nature* 322:445–448, 1986; U.S. Pat. No. 5,464,764). Oligonucleotides designed to target specific gene segments in the ES cell are combined with lambda Beta protein or other ssDNA binding polypeptide and introduced into ES cells by electroporation or other transformation methods. The oligonucleotides may be designed as a series of overlapping segments with 3' overhangs. Such transformed ES cells can thereafter be combined with blastocysts from a non-human animal. The ES cells thereafter colonize the embryo and can contribute to the germ line of the resulting chimeric animal (Jaenisch, *Science* 240:1468–1474, 1988).

For example, sequences encoding positive selection marker neomycin resistance gene are synthesized as a series of overlapping 70-mer oligonucleotides, 20 base pairs of overlap and 3' overhangs. The 3' terminal oligonucleotides are designed to insert into the second exon of the mouse hox 1.1 gene as described in U.S. Pat. No. 5,464,764. Because the overlapping oligonucleotides combine to encode a promoterless neomycin resistance gene, only those that successfully incorporate into the targeted mouse hox 1.1 second exon will express the neo gene product and have the neomycin resistance phenotype. The targeting is designed to provide the synthetic neomycin resistance gene with an operable promoter and translation start derived from the mouse hox 1.1 gene. The targeting DNA is also designed so that random incorporations elsewhere in the ES cell genome are unlikely to be operably linked to any promoter to allow transcription and translation.

The series of overlapping oligonucleotides with 3' overhangs (about 200 nanograms each) are combined with 10 µM lambda Beta protein and introduced into ES cells by electroporation using the Promega Biotech X-Cell 2000. Rapidly growing cells are trypsinized, washed in DMEM, counted and resuspended in buffer containing 20 mM HEPES (pH 7.0), 137 mM NaCl, 5 mM KCl, 0.7 mM $Na_2HPO_4$, 6 mM dextrose, and 0.1 mM beta-mercaptoethanol. Just prior to electroporation, the oligonucleotides and lambda Beta protein are added to $10^7$ ES cells in each 1 ml-cuvette. Cells and DNA are exposed to two sequential 625 V/cm pulses at room temperature, allowed to remain in the buffer for 10 minutes, then plated in non-selective media onto feeder cells.

Following two days of non-selective growth, the cells are trypsinized and replated onto G418 (250 µg/ml) media. The positive-selection is applied for three days. Because of the high efficiency of lambda Beta-mediated recombination, the need for further selection (for example, negative selection by introducing a thymidine kinase gene and selecting with ganciclovir) can be obviated. Appropriately transformed, G418-resistant cells are grown in non-selective media for 2–5 days prior to injection into blastocysts (according to the method of Bradley in: *Teratocarcinomas and Embryonic Stem Cells, A Practical Approach,* edited by E. J. Robertson, IRL Press, Oxford (1987), p. 125).

Blastocysts containing the targeted ES cells are implanted into pseudo-pregnant females and allowed to develop to term. Chimeric offspring are identified by coat-color markers and those males showing chimerism were selected for breeding offspring. Those offspring which carry the mutant allele can be identified by coat color, and the presence of the mutant allele reaffirmed by DNA analysis by tail-blot, DNA analysis.

Thus, the method markedly simplifies the construction of gene knockouts and gene modifications in ES cells. In addition to its possible relevance to plant, animal and human gene therapy, the method will simplify the construction of transgenic animals harboring either gene knockouts or gene modifications.

As described for stem cells and in Example 14, a broad range of ssDNA and ssDNA binding polypeptide concentrations will be effective. For example, both ssDNA and ssDNA binding protein may be present in amounts ranging from 0.001 µM to 100 mM; or from 0.1 µM to 1 µM; or from 1 µM to 100 µM. Oligonucleotide length can be varied in accordance with parameters presented in Example 12. There is no particular upper limit on oligonucleotide length. In addition, two or more oligonucleotides can be included which have complementary 5' ends (for example with 10, 20, 30, 40 bp complementary 5' ends), thereby creating 3' overhangs which are effective substrates for ssDNA binding polypeptides such as lambda Beta. In addition, RecT, P22 Erf, Rad52, and other double strand break repair ssDNA binding polypeptides can be substituted for lambda Beta, in the same ranges described for lambda Beta. Those skilled in the art will recognize that culture and electroporation conditions are readily variable without materially reducing homologous recombination. Moreover, nucleic acid may be introduced into the cell by any suitable macromolecular transfer method.

Example 16

Homologous Recombination in Plants

The methods disclosed herein are also applicable to the manipulation of plant cells and ultimately the genome of the entire plant. A wide variety of transgenic plants have been reported, including herbaceous dicots, woody dicots and monocots. For a summary, see Gasser et al., *Science* 244: 1293–1299 (1989). A number of different gene transfer techniques have been developed for producing such transgenic plants and transformed plant cells. One technique used *Agrobacterium tumefaciens* as a gene transfer system (Rogers et al., *Methods Enzymol.* 118, 627–640, 1986). A closely related transformation utilizes the bacterium *Agrobacterium rhizogenes*. In each of these systems a Ti or Ri plant transformation vector can be constructed containing border regions which define the DNA sequence to be inserted into the plant genome. These systems previously have been used to randomly integrate exogenous DNA to plant genomes.

Preferably, DNA designed for homologous recombination with a target DNA sequence in plants are combined with lambda Beta protein or other ssDNA protein and directly transferred to plant protoplasts by way of methods analogous to that previously used to introduce transgenes into protoplasts. Concentration of the DNA and ssDNA binding proteins are as described in Example 15 (see, e.g. Paszkowski et al., *EMBO J.*, 3:2717–2722, 1984; Hain et al., *Mol. Gen. Genet.*, 199, 161–168, 1985; Shillito et al. *Bio./Technology* 3:1099–1103, 1985; and Negrutiu et al., *Plant Mol. Bio.* 8:363–373, 1987). Alternatively, the PNS vector is contained within a liposome which can be fused to a plant protoplast (see, e.g. Deshayes et al., *EMBO J.* 4:2731–2738, 1985) or is directly inserted to plant protoplast by way of intranuclear microinjection (see, e.g. Crossway et al., *Mol. Gen Genet.* 202:179–185, 1986, and Reich et al., *Bio/Technology* 4:1001–1004, 1986). Microinjection can be used for transfecting protoplasts. The DNA and ssDNA binding proteins can also be microinjected into meristematic inflorescences. De la Pena et al., *Nature* 325:274–276, 1987. Finally, tissue explants can be transfected by way of a high velocity microprojectile coated with the DNA and ssDNA binding proteins analogous to the methods used for insertion of transgenes (see, e.g. Vasil, *Bio/Technology* 6:397, 1988; Klein et al., *Nature* 327:70, 1987; Klein et al., *Proc. Natl. Acad. Sci. U.S.A.* 85:8502, 1988; McCabe et al., *Bio/Technology* 6:923, 1988; and Klein et al., *Genetic Engineering,* Vol 11, J. K. Setlow editor (Academic Press, N.Y., 1989)). Such transformed explants can be used to regenerate for example various serial crops. Vasil, *Bio/Technology* 6:397, 1988.

Once the DNA and ssDNA binding protein have been inserted into the plant cell by any of the foregoing methods, homologous recombination targets the oligonucleotide to the appropriate site in the plant genome. As in previous examples, the oligonucleotide may be a series of overlapping ssDNAs with 5' or 3' overhangs. Depending upon the methodology used to transfect, selection is performed on tissue cultures of the transformed protoplast or plant cell. In some instances, cells amenable to tissue culture may be excised from a transformed plant either from the F0 or a subsequent generation.

The amino acid composition of various storage proteins in wheat and corn, for example, which are known to be deficient in lysine and tryptophan may also be modified. PNS vectors can be readily designed to alter specific codons within such storage proteins to encode lysine and/or tryptophan thereby increasing the nutritional value of such crops. For example, the zein protein in corn (Pederson et al., *Cell* 29:1015, 1982) can be modified to have a higher content of lysine and tryptophan by the vectors and methods disclosed herein.

Example 17

Materials and Methods Used in Examples 18–22

Bacterial strains. All of the strains used except DH10B were maintained at 32° C. because of the temperature inducible prophage. DY303 was constructed by infecting DH10B cells (Gibco) with a λ phage carrying recA (λcI857 recA$^+$) (a gift from F. W. Stahl) and lysogens were selected. Strain EL11 was constructed by replacing the tet gene of DY380 with a cassette containing the cat and sacB genes by selecting CmR. EL11 cells are Tet$^S$, Cm$^R$ and sensitive to 2% sucrose. Strain EL250 was constructed by replacing the cat-sacB cassette of EL11 cells with araC and the arabinose promoter-driven flpe recombinase gene (P$_{BAD}$flpe) selecting in the presence of sucrose. EL250 cells are resistant to 2% sucrose. Strain EL350 was constructed in a similar manner except for Cre instead of flpe.

Construction of plasmids. The IRES-eGFPcre-FRT-kan-FRT targeting cassette was PCR amplified from pICGN21, which was constructed by subcloning a 1.9 kbp HindIII/AccI-digested and filled-in FRT-kan-FRT fragment from pFRTneo into the NotI/BclI-digested and filled-in cloning site of pIRESeGC. The FRTneo was constructed by amplifying the kan gene along with the Beta lactamase promotor from pEGFP-C1 (Clontech) with primers
5'CTGCAAGGCGATTAAGTTGGGTAACGC-CAGGGTTTTCGTCAGGTGGC ACTTTCGGG (SEQ ID NO: 13) and 5'CTCAGAAGAACTCGTCAAGAAGG (SEQ ID NO: 14). The amplified fragment was then targeted between the frt sites in pNeoβ-gal (Stratagene). The pIRESeGC was generated by inserting the 2 kbp NheI/MluI-digested and filled-in eGFPcre fragment from pEGC into the 3.5 kbp BamHI-digested and filled-in cloning site of pNTR-lacZPGKneoloxP (Arango et al., *Cell* 99: 409–19, 1999). The pEGC was generated by subcloning a 1.05 kbp EcoRI/KpnI PCR fragment containing the Cre gene from pGKmncre into the EcoRI/KpnI site of pEGFP-C1. This PCR fragment was generated by amplifying the Cre gene from pGKmncre with primers 5'GTAGGTACCTCGAGAATCGCCATCTTCCAGCAGGC (SEQ ID NO: 15) and 5'TCGAATTTTCTGCATCCAATTTACTGACCGTACACC (SEQ ID NO: 16), which contain EcoRI and KpnI cleavage sites, respectively, at their 5' ends.

To construct the pTamp vector, the amp-targeted pBeloBAC11 was first generated by replacing the LoxP site in pBeloBAC11 (Shizuya et al., *Proc. Natl. Acad. Sci.* 89: 8794–7, 1992) with the PCR amplified amp gene from pEGFP (Clontech). The primers used for amplification are 5'GCAAGTGTGTCGCTGTCGACGAGCTCGCGAGCTCGGACATGAGGTTGTCTTAGACGTCAGGTGGCAC (SEQ ID NO: 17) and 5' CATAGTTAAGCCAGCCCCGACACCCGCCAACACCCGCTGACGCGAACCTCACGTTAAGGGATTTTGGTC (SEQ ID NO: 18), which are homologous to the amp gene of pEGFP (in plain) and to sequences flanking the LoxP site in pBeloBAC11 (in italic). A 2.4-kbp PCR fragment amplified from amp-targeted pBeloBac11 with primers 5'GCAGGATCCAGTTTGCTCCTGGAGCGACA (SEQ ID NO: 19) and 5'TGCAGGTCGACTCTAGAGGATC (SEQ ID NO: 20) was then cloned into the XhoI/XbaI and filled-in site of pCS (Stratagene) to create the pTamp vector. The 2.4 kbp amp cassette containing an amp gene along with 920 bp of 5', and 370 bp of 3', pBe10BAC11 vector sequence flanking the LoxP site can be released by BamH1 digestion and used directly to replace the LoxP site in any pBeloBAC11-derived BACs with amp.

The pKO4 vector containing the cat-sacB targeting cassette is a derivative of pKO3 (Link et al., *J Bacteriol.* 179: 6228–37, 1997) in which 605 bp had been deleted between cat and sacB.

The araC-$P_{BAD}$flpe targeting cassette was amplified from pBADflpe, which was constructed by subcloning a 1.4 kb PstI/KpnI fragment from pOGFlpe (Buchholz et al., Nat. Biotechnol. 16: 657–62, 1998) into pBAD/MycHis-A (Invitrogen). The araC-$P_{BAD}$cre targeting cassette was amplified from pBADcre, which was constructed by introducing a 1.2 kb HindIII/NcoI fragment from pGKmncre into pBAD/His-C (Invitrogene).

Amplification primers for targeting or GAP repair cassette DNAs. For all primers listed below, nucleotides in italics are homologous to the targeted sequence, while those in plain text are homologous to amplification cassettes. The Tet$^R$ cassette used for targeting cro-bio in DY330 was amplified from Tn10 with primers: 5'TGGCGGTGATAATGGTTGCATGTACTAAGGAGGTTGTATGCTCTTGGGTTATCAAGAGGG (SEQ ID NO: 21) and 5'GGCGCTGCAAAAATTCTTTGTCGAACAGGGTGTCTGGATCACTCGACATCTTG GTTACCG (SEQ ID NO: 22). The cat-sacB cassette used for replacing the tet gene in DY363 was amplified from pKO4 with primers: 5'TGGCGGTGATAATGGTTGCATGTACTAAGGAGGTTGTATGCTGTGACGGAAGATCACTTCG (SEQ ID NO: 23) and 5'GGCGCTGCAAAAATTCTTTGTCGAACAGGGTGTCTGGATCCTGAGGTTCTTAT GGCTCTTG (SEQ ID NO: 24). The araC-$P_{BAD}$flpe and araC-$P_{BAD}$cre cassettes used for replacing the cat-sacB in EL11 were amplified from pBADflpe and pBADcre with primers: 5'TGGCGGTGATAATGGTTGCATGTACTAAG GAGGTTGTATGAAGCGGCATGCATAATGTGC (SEQ ID NO: 25) and 5'GGCGCTGCAAAAATTCTTTGTCGAACAGGGTGTCTGGATCCTGTGTCCTACTCAGGA GAGCGTTC (SEQ ID NO: 26). The IRES-eGFPcre-FRT-kan-FRT cassette used for targeting the Eno2 locus was amplified from pIGCN21 with primers: 5'CGCTTCGCGGGACATAATTTCCGAAATCCCAGTGTGCTGTGAGCCAAGCTATCGAATTCCGCC (SEQ ID NO: 27) and 5'GAGGCTCCAGGAGAATGAGATGTTCCCGCGTTCAGGCAAGCGCTATTCCAGA AGTAGTGAGGA (SEQ ID NO: 28). The oligonucleotides used to target the flag cassette into the 5' end of the Sox4 gene were annealed and polymerase-extended using primers: 5'GCGAGCGTGTGAGCGCGCGTGGGCGCCCGGCAAGCCGGGGCCATGGATTACAAGGATGACGACGATAAGGTACAACAGA (SEQ ID NO: 29) and 5'GGCCAGCAGAGCCTCAGTGTTCTCCGCGTTGTTGGTCTGTTGTACCTTATCGTCGTCATCCTTGTAATCCATGGCCCCC (SEQ ID NO: 30).

The linear pBR322 derivative used to subclone the 25-kbp fragment from the modified Eno2 locus was amplified with primers: 5'CTCTCCATGCCTGTCTGGGTGAGGGTGGCCCAGGGGCGATGGCTATGAGAGAGGTCGACTTCTTAGACGTCAGGTGGCAC (SEQ ID NO: 31) (Eno2-C-L1) and GCAATGCAGAGAAGCCTTGTACTGGGATGACAGAGACGGAGGGGAAGAGGAGGCGGCCGCGATACGCGAGCGAACGTGA (SEQ ID NO: 32) (Eno2-C-R1/2). The amplification primers for the other experiments were: 48-kbp modified fragment, 5'GACTTCTATGACCTGTACGGAGGGGAGAAGTTTGCGACGTGACAGAGCTGGTCGTCGACTTCTTAGACGTCAGGTGGCAC (SEQ ID NO: 33) (Eno2-C-L2/3/4) and Eno2-C-R1/2; 60-kbp modified fragment, Eno2-C-L2/3/4 and 5'GCCCCATACACGTAAATGTACATAGAATCACACAGCATCACTTCTATGGATGCGGCGGCCGCGATACGCGAGCGAACGTGA (SEQ ID NO: 34) (Eno2-C-R3); 80-kbp modified fragment, Eno2-C-L2/3/4 and 5'CATCCAGTAGAACTTGGGAGTGAAGCTAGAGCCAAGGCCATCTAAGTGACAGGCGGCCGCGATACGCGAGCGAACGTGA (SEQ ID NO: 35) (Eno2-C-R4). These primers contained 5' regions homologous to the target sequence and 3' regions homologous to pBR322. PCR products were purified using a Qiaex II gel extraction kit (Qiagen) and digested with DpnI to remove contaminated template.

Preparation of electrocompetent cells and generation of recombinants. For BAC modification, overnight cultures containing the BAC were grown from single colonies and were diluted 50-fold in LB medium and grown to an $OD_{600}=0.5$–0.7. 10-ml cultures were then induced for Beta, Exo, and Gam expression by shifting the cells to 42° C. for 15 minutes followed by chilling on ice for 20 minutes. Cells then were centrifuged for 5 minutes at 5,500 g at 4° C. and washed with 1.5 ml of ice-cold sterile water three times. Cells were then resuspended in 50 µl of ice-cold sterile water and electroporated. For BAC transformation, the induction step was omitted.

Cell transformation was performed by electroporation of 100–300 ng linear DNA into 50 µl of ice-cold competent cells in cuvettes (0.1 cm) using a Bio-Rad gene pulser set at 1.75 kV, 25 µF with pulse controller set at 200 ohms. 1 ml of LB medium was added after electroporation. Cells were incubated at 32° C. for 1.5 hours with shaking and spread on appropriate selective or nonselective agar media.

Production of transgenic mice. Modified BAC and the p25-kbp subclone DNAs were purified using cesium chloride gradients as described (Antoch et al., 1997). The 25-kbp subclone DNA was linearized by NotI digestion before microinjection. BAC DNA (1 µg/ml) and 25-kbp subclone DNA (2 µg/ml) were microinjected into the pronucleus of (C3H/HeN-Mtv⁻ X C57BL/6Ncr) $F_2$ zygotes. Transgenic founders were subsequently identified by Southern analysis using a Cre probe or by PCR using primers 5'CTGCTG-GAAGATGGCGATTCTCG (SEQ ID NO: 36) and 5'AACAGCAGGAGCGGTGAGTC (SEQ ID NO: 37) that flank the 3' insertional junction.

Histochemical analysis of β-galactosidase expression. Mice at 4 to 5 weeks of age were sacrificed in $CO_2$ and perfused with 4% paraformaldehyde in PBS (pH 7.3). The brains, spinal cords and eyes were removed and postfixed for 3 hours. Vibratome sections (20 µm) of brains were mounted on slides and used directly for X-gal staining or for immunocytochemistry. For spinal cords and eyes, cryostat sections (20 µm) were used that were made by cryoprotecting tissues in 30% sucrose in PBS overnight and embedding the tissues in freezing compound (OCT, Sakura). Before X-gal staining, samples on slides were postfixed with 0.25% glutaraldehyde in PBS and briefly washed with rinse solution (0.1 phosphate buffer pH7.3, 0.1% deoxycholic acid, 0.2% NP40 and 2 mM $MgCl_2$). X-gal staining was performed by incubating samples in staining buffer (2.5 mg/ml X-gal, 5 mM potassium ferricyanide and 5 mM potassium ferrocyanide in staining buffer) for 2 hours at 37° C. followed by counterstaining with 0.25% eosin (Fisher).

Immunocytochemistry. Immunostaining was carried out using the ABC Vectastain kit (Vector Labs) on 20 µm vibratome sections. Sections were blocked with PBS (pH7.3 containing 0.2% Triton X-100, 1.5% bovine serum albumin and 5% normal goat serum) at room temperature for 2 hours and incubated with primary Eno2 antibody, a poly clonal rabbit anti-Eno2 antiserum (Chemicon) at 1:100 dilution in PBS solution. After incubation with a secondary biotinylated antibody and the ABC reagent, peroxidase was reacted with 0.05% diaminobenzidine tetrahydrochloride (DAB) and 0.003% hydrogen peroxide.

Example 18

Creation of Improved Bacterial Host Strains for Lambda-Mediated Recombination in BACs Transfer of Lambda Recombination Genes to DH10B cells.

To facilitate the use of lambda-mediated recombination with BACs, an improved phage-mediated recombination system has been created for efficient recombination using BACs. The DH10B strain unlike most other strains of E. coli is efficiently transformed with BAC DNA and contains many of the BAC genomic libraries; it was judged to be a good host strain for subsequent modification.

Because DH10B is recA defective, standard genetic crosses cannot be used to place the defective lambda prophage used for lambda-mediated recombination into the DH10B strain of E. coli. To circumvent this problem, DH10B was first converted to recA+, then the lambda recombination genes were crossed in and the strain was again made recA− but now carrying the lambda genes.

To make DH10B recA+, a lambda transducing phage carrying the recA+ gene was used to lysogenize DH10B creating the derivative DY303. In strain DY330 used for λ mediated recombination, the tet gene conferring tetracycline resistance was inserted by homologous recombination where the cro-bioA deletion exists creating strain DY363. A P1 lysate made on DY363 was used to infect DY303 and by standard bacterial genetics the tet gene in the cro-bioA deletion was crossed into DY303. This deletes a large segment of the λ DNA of the lysogen including the recA+ gene. This new derivative of DH10B and DY303 is named DY380, is RecA− and carries the tet selectable marker substituted for the cro-bioA segment. It was observed that DY380 cells were transformed with BAC DNA at efficiencies of $10^{-6}$ to $10^{-4}$.

Creation of DY380 Derivatives Containing Arabinose-inducible Cre or Flpe Genes

BAC targeting often makes use of a selectable marker to introduce the targeting cassette into the targeted locus. The selectable marker can, however, interfere with the subsequent function of the targeted locus. To circumvent this problem, the inventors noted that a selectable marker flanked with either frt or LoxP sites can be removed by either Flp or Cre recombinases, respectively. Thus, the inventors have created two new strains, EL250 and EL350, by ultimately replacing the tet gene in DY380 with araC and placing the flpe and Cre genes under an arabinose-inducible promoter. The genotypes of DY380, EL250, and EL350 are shown schematically in FIG. 6. Although the arabinose-inducible promoter $p_{BAD}$ was used in this example, essentially any inducible promoter may be used to activate flpe and Cre expression.

In DY380's prophage, tet is located between cI857 and bioA. In EL250's prophage, flpe replaces tet (flpe is a genetically engineered flp that has a higher recombination efficiency than the original flp gene; Buchholz et al., Nature Biotechnology 16:657–662, 1998). Thus, as illustrated in FIG. 6, both EL250 and EL350 have heat-inducible homologous recombination (the λ red genes) and arabinose-inducible site-specific recombination (flpe or Cre) functions. This dual regulation allows both selective targeting by recombination as well as the subsequent removal of the selection marker from the targeted locus by site-specific recombination.

Improved Approach for Introducing Defective Lambda Prophages into Bacteria: Mini Lambda Circles A method has been developed for introducing the λ-mediated recombination system directly into nearly any E. coli strain including recA defective DH10B derivatives. These derivatives can carry BACs, PACs, or other vectors.

The DY330 strain carries deletion of prophage genes from cro through bioA. This deleted segment of λ and bioA were replaced to create a derivative that contains a fully normal λcI857 single-copy lysogen. Lysogens of this type can be induced at 42° C. to express λ functions including the Red recombination functions. Because the λ carries all of the replication and lytic genes, induction for longer than 6 minutes causes death of cells carrying the lysogen. However, by inducing for less than 6 minutes, for example 4 minutes, recombination functions are only partially activated, but cells survive when returned to grow at 32° C. Using, for example, a 4-minute time of induction, λ-mediated recombinants can be generated between linear, electroporated DNA and the chromosome including the DNA of the prophage. Thus, phage lambda itself can be used to lysogenize and generate recombinants in BAC strains. However, recombination efficiency would be low because of the short induction time.

PCR cassettes containing 5 genes for different drug resistance markers were amplified [cat, kan, amp, tet, spec (strep)] with flanking homologies so as to replace prophage genes from cro through ea59 with the respective drug markers selecting with that drug for resistant recombinants at 32° C. A contiguous prophage DNA segment from base position 38,044 of the λ map in cro to base position 25,737 of the λ map in sib are replaced by the drug cassettes (see Court and Oppenheim). This deletion eliminates all replication and lysis genes of the prophage creating a defective prophage similar to that of the original DY330. The difference is that this prophage has both attachment sites attL and attR at the termini of the prophage whereas DY330 has attR through bioA deleted as part of the cro-bioA deletion.

This set of strains (with respective drug cassettes) can be induced for longer times than the complete lambda without killing the cells thereby providing maximal homologous recombination activity just as with DY330. The $P_L$ operon of these prophages include the int and xis genes. Induction activates their expression and because both attL and attR are present causes site specific excision of the prophage as a DNA circle carrying its associated drug marker. Cells undergoing induction for 15 minutes may lose the original prophage. This happens in about 50% of the cells. The other 50% still have the prophage. The 50% with the prophage are likely to occur by reintegration of the circular DNA at the vacated attB site through Int-mediated site specific recombination.

The defective prophage DNA can be isolated and purified from these lysogens, if after a 15 minute induction, cells are lysed and DNA is isolated by plasmid purification protocols, i.e. by Qiagen columns. The circular phage DNA with its drug markers can be purified. This DNA cannot replicate upon retransfection into E. coli strains but it can express its pL operon and Int function to allow integration of the circular DNA by site specific recombination between attP in the circular DNA and attB in the bacterial chromosome. Only Int and the host IHF functions are required for site-specific recombination. Such integrated DNAs are stable, are immune and can be selected by the drug marker each carries.

Because RecA is not required for site specific Int-mediated recombination, DH10B derivatives can be used for transformation and for integration of the circular defective phage DNA selecting for its appropriate drug marker.

The defective mini-prophage can also be induced as part of a di-lysogen in which a complete λ cI857 phage is also present. The phage lysate created by this 90 minutes induction at 42 degrees in L-Broth generates normal lambda phage particles as well as particles that contain the defective mini-prophage DNA (in λ terminology docL particles). Infection of these lysates into cells (e.g. DH10B) allows DNA injection of the mini-prophage DNA, site specific recombination, and selection for the drug marker carried on that DNA.

Example 19

An Improved Strategy and Improved Reagents for BAC Engineering

To test the prophage system of Example 17 in BAC engineering, the efficiency of BAC recombination in EL250 cells was investigated. In the experiments described in this example, a selectable cassette was targeted to a mouse neuron-specific locus in a 250 kb BAC. The BAC was then further modified to enhance its usefulness in subsequent mouse genetic studies. These experiments validated an improved strategy and provided improved reagents for BAC engineering using the lambda recombination system.

The Eno2 gene is located in the middle of 284H12, a fully sequenced BAC (obtained from Research Genetics; Ansari-Lari et al., Genome Research 8:29–40, 1998). The Eno2 gene was targeted because it is neural-specific and expressed in most mature neurons (Marangos and Schmechel, Annual Review of Neuroscience 10:269–295, 1987). By knocking out eno2 and replacing it with a Cre-containing cassette, a BAC transgenic line that expresses Cre in all mature neurons was created (described in Example 21). This BAC transgenic line is useful for subsequent conditional knockout studies. The inventors used a BAC approach in part because BACs are large enough to contain all the important regulatory sequences required for proper regulation of gene expression.

The following describes the construction of the BAC transgenic line with neuronal-specific Cre expression.

Generation of the Targeting Cassette and BAC-containing EL250 Cells

The IRES-eGFPcre-FRT-kan-FRT targeting cassette was PCR amplified from pICGN21, which was constructed by subcloning a 1.9 kbp HindIII/AccI-digested and filled-in FRT-kan-FRT fragment from pFRTneo into the NotI/BclI-digested and filled-in cloning site of pIRESeGC. The IRES-eGFPcre-FRT-kan-FRT cassette was amplified using chimeric 63 nt primers. The 3' 21 nt of each primer was homologous to the targeting cassette used for amplification while the 5' 42 nt was homologous to the last exon of Eno2 where the cassette was to be targeted by recombination. The primers were designed to precisely target the cassette downstream of the Eno2 stop codon and upstream of its polyA site.

The Eno2-containing 284H12 BAC was electroporated into EL250 cells and six chloramphenicol resistant ($Cm^R$) colonies selected. Digestion of BAC DNA from six $Cm^R$ colonies with EcoRI or HindIII showed that one had an abnormal digestion pattern. However, in other BAC electroporation experiments involving the analysis of more than 76 additional colonies, no abnormal BACs were identified. These results indicate that BAC rearrangements during electroporation are rare. Subsequent experiments were carried out with $Cm^R$-resistant EL250 colonies harboring BACs having proper EcoRI and/or HindIII digestion patterns.

Generating and Isolating a BAC with a Disrupted Eno2 Locus

Next, the 284H12 BAC was modified to disrupt the eno2 locus with the IRES-eGFPcre-FRT-kan-FRT targeting cassette. The methods used in these experiments were similar to those described extensively herein (and in Yu et al., Proc. Natl. Acad. Sci. U.S.A. 97:5978–5983, 2000). The approach is illustrated schematically in FIG. 7.

EL250 cells carrying the 284H12 BAC were shifted to 42° C. for 15 minutes to induce lambda Exo, Beta, and Gam expression. The cells were then electroporated with 300 ng of the amplified IRES-eGFPcre-FRT-kan-FRT cassette, and kanamycin-resistant ($Km^R$) colonies were selected. A kanamycin-resistant phenotype indicated that the targeting cassette was successfully integrated into the 284H12 BAC (illustrated as "Targeting," FIG. 7, middle). Approximately 5200 $Km^R$ colonies were obtained from $10^8$ electroporated cells for a targeting efficiency of about $10^{-5}$. No colonies were obtained from control cells that were not heat-induced. Thus, lambda recombinase expression was required for efficient recombination.

Twenty-four kanamycin resistant colonies were analyzed with whole-cell PCR using primers that flanked the targeted locus. The PCR results indicated that all were correctly targeted. Sequencing of the targeted region from six colonies, however, showed that three carried point mutations. To determine whether these point mutations were introduced during PCR amplification or during homologous recombination, the targeting was repeated. This time, however, the PCR-amplified IRES-eGFPcre-FRT-kan-FRT cassette was subcloned into the SmaI site of pBluescript by blunt-end ligation before targeting, and plasmids carrying wild type amplified cassettes identified by DNA sequencing. These cassettes were then released from the plasmid by BamHI digestion and used for targeting. Using this two-step method, all twelve targeted BACs that were subsequently sequenced contained wild type IRES-eGFPcre-FRT-kan-FRT cassettes. These results indicate that the point mutations were introduced by the primers used or during PCR amplification of the targeting cassette rather than during targeting.

Removing the Kanamycin-resistance Marker

Figure 7:
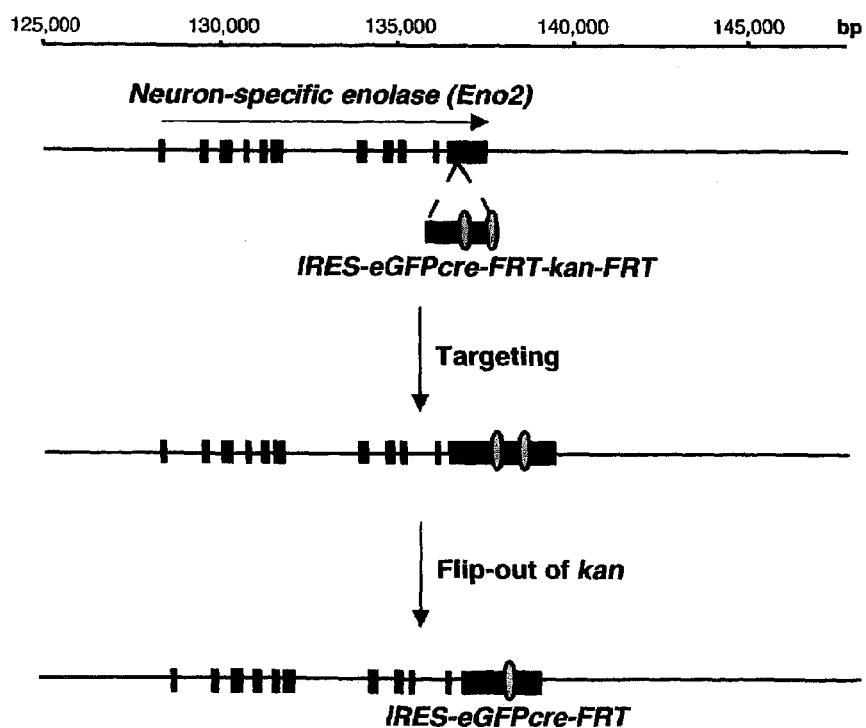
FIG. 7 illustrates a strategy for BAC engineering. This figure illustrates the relative position of the Eno2 gene in the fully sequenced 250-kbp BAC, 284H12 and the different steps used to introduce Cre into the last exon of Eno2. In the targeting cassette, frt sites are denoted by ellipses, the kan gene by a red rectangle and the GFPcre fusion gene by a blue rectangle. The green boxes represent Eno2 exons.

Next, the kan selectable marker was removed from the BAC to prevent it from possibly interfering with Cre expression. This process was initiated by arabinose treatment, which induces EL250 cells to express the Flpe recombinase. The process is illustrated in FIG. 7, bottom line ("Flip-out of kan").

Overnight cultures from single $Km^R$ colonies were diluted 50-fold in LB medium and grown till $OD_{600}$=0.5. Flpe expression from the EL250 cells was then induced by incubating the cultures with 0.1% L-arabinose for 1 hour. The bacterial cells were subsequently diluted 10-fold in LB medium, grown for an additional hour, and spread on chloramphenicol plates (12.5 ug/ml). The next day, 100 $Cm^R$ colonies were picked and replated on kan plates (25 ug/ml) to test for loss of kanamycin resistance. Chloramphenicol resistance indicates that the cell retained the BAC, whereas kanamycin sensitivity indicates that kan has been successfully removed from the BAC. All colonies were $Km^s$ and contained a single frt site at the targeted locus.

Without being bound by theory, it is likely that the surprisingly high recombination efficiency reflects the tight control of Flpe expression afforded by the single copy $P_{BAD}$ promoter and flpe gene, and the fact that the frt sites are located in cis rather than in trans to each other.

Removing an Undesirable LoxP Site in the BAC Vector Backbone

A LoxP site contained in the BAC vector backbone (pBeloBAC11; Shizuya et al., *Proc. Natl. Acad. Sci. U.S.A.* 89:8794–8797, 1992) was removed by a final round of gene targeting.

To facilitate the removal of this undesirable LoxP site, a new plasmid, pTamp, was constructed that contains an amp gene flanked by 920 bp of pBeloBAC11 sequence located 5' of the LoxP site and 370 bp of pBeloBAC11 sequence located 3' of the LoxP site. This amp insert can be released from pTamp by BamHI digestion and used to replace the LoxP site in the BAC transgene by gene targeting. This targeting reaction is very efficient due to the large amount of homology between the amp cassette and the pBeloBAC11 vector (56,200 colonies per $10^8$ electroporated cells).

Upon removal of the undesirable LoxP site, the modified 284H12 BAC was used in the transgenic mouse studies described in Example 21.

Example 20

Subcloning by GAP Repair

This λ-mediated recombination system can also be used to subclone fragments from BACs without the use of restriction enzymes or DNA ligases. This form of subcloning relies on gap repair to recombine the free ends of a linear plasmid vector with homologous sequences carried on the BAC (FIG. 8). The method is readily adaptable to other forms of intramolecular and extrachromosomal DNA, such as plasmids, yeast artificial chromosomes, P1 artificial chromosomes, and cosmids. This novel method combines lambda mediated recombination with gap repair to enable recombination of very large DNA segments onto an extrachromosomal vector.

The linear plasmid vector with an amp selectable marker and an origin of replication carries the recombinogenic ends (FIG. 8B). The vector is generated by PCR amplification using two chimeric primers. The 5' 45–52 nt of each primer is homologous to the two ends of the BAC sequence to be subcloned while the 3' 20 nt is homologous to plasmid DNA. Recombination generates a circular plasmid in which the DNA insert was retrieved from the BAC DNA via gap repair. Circular plasmids are selected by their $Amp^R$.

To determine the maximum sized fragment that can be subcloned from BACs using this method, several different pairs of primers were generated in which the homology segments were located 25 kb, 48 kb, 60 kb, or 80 kb apart in the Eno2 BAC DNA (FIG. 8A). Rare cutter NotI and SalI restriction sites were also incorporated into these primers so that the subcloned fragments could be released from the recombinant clones intact. Using pBluescript as the cloning vector, it was possible to subclone the 25 kb fragment. However, attempts to subclone larger fragments were unsuccessful. As a possible explanation for this result, it was hypothesized that subclones containing larger fragments on a high copy vector such as pBluescript were toxic to the cell.

To determine if the hypothesis was correct, a lower copy number vector (pBR322, with its copy number control element intact) was used as the cloning vector. Fragments as large as 80 kb could be subcloned with a pBR322 vector. Not all subclones obtained by gap repair had the correct inserts (as determined by restriction enzyme pattern analysis). Some subclones lacked inserts while others contained inserts with aberrant restriction patterns. In order to confirm that the correct insert has been subcloned, when using subcloning by gap repair, a method of screening subclones can be used to assure that the selected subcloned contains the desired insert. Such methods include restriction mapping, sequencing, PCR analysis, Southern analysis, etc., and other methods well known to those of skill in the art.

The ability to subclone large fragments of genomic DNA by gap repair should facilitate many studies in genome research that were difficult or impossible to perform previously. For example, Gap repair for cloning on to vectors can be used with many different vectors used for protein expression in bacteria, plants and animal cells, mutagenesis, cloning, transcription, etc. Targeting vectors or transgenic constructs can be subcloned with ease, and virtually any region of the engineered BAC can now be included in the desired subclone.

Lambda mediated recombination combined with gap repair makes it possible to subclone fragments from complex mixtures without first purifying the DNA to be subcloned. This greatly facilitates the subcloning process and allows for high throughput subcloning of tens of thousands of genes or DNA molecules into many different vector backbones. This will greatly facilitate studies designed to determine the function of genes uncovered in large scale sequencing projects. For example, cDNA clones for genes of unknown function can be subcloned into many different expression vectors and the function of these genes studies in cell-based assays in vitro or in the whole animal. This type of subcloning does not rely on PCR amplification, which can introduce unwanted mutations into the subcloned sequences.

Subcloning by gap repair also facilitates the identification of locus control regions or other regulatory elements that may be located at some distance from the gene. Many such potential elements are presently being identified by techniques such as comparative genome sequencing. Examples include pathogenicity islands, replicative origins and segregation elements. The ability to modify precisely these regulatory sequences on BACs, combined with the ability to include or exclude them during the subcloning process, will make it possible to dissect the function of these sequences in the whole animal or in vitro at a level not previously possible.

Example 21

Production of Transgenic Mice Using BACs

Examples 18–20 describe the construction of a modified BAC believed to contain all of the regulatory sequences needed for neural-specific Cre expression in transgenic mice. To investigate this hypothesis, the modified BAC described in Example 18 was injected into (C3H/HeN-Mtv$^-$ X C57BL/6Ncr) $F_2$ zygotes. A BAC transgenic line carrying approximately two copies of the transgene was then established.

In addition to the BAC transgenic line, two transgenic lines carrying 25-kbp subclones of the BAC were also established. The 25-kbp subclones contains the entire modified Eno2 coding region as well as 10 kbp of 5' and 5 kbp of 3' flanking sequences, respectively. One transgenic line, 25 kbp-1 carries approximately four copies of the transgene, while the second, 25 kbp-2 carries approximately five copies of the transgene. Thus, Cre expression in the BAC transgenic line could be compared to Cre expression in the transgenic lines carrying the subclone.

The transgenic mice were crossed to ROSA26 reporter mice, which contain a lacZ reporter that can be activated by Cre recombinase (Soriano, *Nature Genetics* 221:70–71, 1999). Double heterozygotes were subsequently analyzed by X-gal staining at 4 weeks of age.

Several different tissues were examined for X-gal expression including the brain, spinal cord, eye, lung, heart, intestine, muscle, liver, spleen, and kidney. Blue stained cells were found only in neural tissue in the three transgenic lines, indicating that both the BAC and the 25-kbp subclone contain the regulatory elements needed for neural-specific expression. The pattern of Cre activity was, however, different in the three lines. Vibratome sections of the brain from the BAC transgenic mice showed blue-stained cells throughout the gray matter but not in the white matter, indicative of Cre activity in most neurons but not in glial cells. In contrast, X-gal staining in the 25 kbp-1 and 25 kbp-2 transgenic mice was present in only a subset of neurons and expression was variable between the two different lines.

Higher power magnification of the cerebellum of the BAC transgenic mice showed that Cre was expressed in virtually all neuronal cells. This included Purkinje cells in the Purkinje cell layer, granule and Golgi cells in the granular layer, basket cells and stellate cells in the molecular layer and neurons of the deep cerebellar nuclei. In contrast, in the 25 kbp-1 line, Cre was expressed in only a subset of Golgi cells in addition to a few cells in the granule and Purkinje cell layers. Glial cells of white matter also expressed Cre indicative of leaky expression. In the 25 kbp-2 line, Cre expression was limited to the gray matter and included a variety of neuronal cell types, including most basket cells, stellate cells, Purkinje cells and neurons of the deep cerebellar nuclei. In contrast, few granule cells and Golgi cells in the granule layer expressed Cre.

Higher power magnification of the hippocampus and cortex showed similar results. In the hippocampus of BAC transgenic mice, virtually all neurons in the cornu Ammonis (CA) region and the dentate gyrus (DG) expressed Cre. The same was true in the cortex, where all six layers of the cortex that contained neurons (layers II–VI) expressed Cre. In contrast, the hippocampus of 25 kbp-1 transgenic mice showed reduced Cre expression in the DG (FIG. 4E) and layers II and III of cortex. The 25 kbp-2 transgenic mice showed even lower levels of Cre expression in the DG. The CA1 and CA2 regions of the CA also failed to express Cre. Cre expression was also greatly reduced in the cortex, with layers II and III showing most the reduction.

Cre activity in the spinal cord, dorsal root ganglion (DRG) and retina of the transgenic mice was also examined in order to determine whether Cre was expressed in mature neurons within the peripheral nervous system. Similar to what was observed for the central nervous system, Cre was expressed in most mature peripheral neurons in the BAC transgenic mice while fewer peripheral neurons expressed Cre in the two 25 kbp transgenic lines.

To determine whether Cre was expressed in all Eno2 protein-positive neurons, a section from the brain of a BAC transgenic animal was immunostained with an anti-Eno2 antibody followed by X-gal staining for Cre activity. Virtually all Eno2-positive neurons were active for Cre. Thus, Cre expression in BAC transgenic animals correlated tightly with native mouse Eno2 promoter-enhancer activity.

The present application, particularly Examples 17–20, describes a highly efficient recombination system for manipulating BAC DNA in *E coli*. The recombination system uses a defective λ prophage to supply functions that protect and recombine the electroporated linear DNA targeting cassette with the BAC sequence. Because the recombination functions are expressed from a defective prophage rather that a plasmid, the recombination functions are not lost during cell growth as often happens with plasmid-based systems. Another advantage of this prophage system is that the λ gam and red recombination genes are under the control of the temperature sensitive λ repressor that provides a much tighter control of gam and red expression than can be obtained on plasmids. This tight regulation, combined with the strong λ pL promoter, which drives gam and red expression to very high levels, makes it possible to achieve recombination frequencies that are surprisingly efficient (at least 50–100 fold higher than those obtained with plasmid-based systems; Narayanan et al., *Gene Therapy* 6:446: 442–447,1999; Muyers et al., *Nucleic Acids Research* 27:1555–1557, 1999). The tight control prevents expression of any recombination functions except for the 15 minute temperature induction.

The ability to precisely manipulate large fragments of genomic DNA, independent of the location of appropriate restriction enzyme sites, has many applications for functional genomics, both in the mouse and in other organisms. As shown herein, Cre can be introduced into the coding regions of genes carried on BACs facilitating the generation of Cre-expressing transgenic lines for use in conditional knockout studies or for use in conditional gene expression studies. Genes can also be epitope tagged and microinjected into the germline of mice carrying a mutation in the gene. If the epitope tagged transgene rescues the mutant phenotype, the epitope tagged protein is functional and the epitope tag can serve as a marker for expression of the gene. Likewise, a gene carried on a BAC can be replaced with another gene and the function of the "knock-in" mutation assayed in transgenic mice.

This recombination system also facilitates the generation of complicated conditional targeting vectors. While the generation of such vectors often used to take several months it can now be done in a only few weeks time. The ability to reversibly express Cre or Flpe recombinases in *E. coli* speeds this process even further. Moreover, as demonstrated in Example 18, a selectable marker flanked with LoxP or frt sites can be now be introduced into an intron of a gene and then removed by transient Cre or Flpe expression leaving behind a solo LoxP or frt site in the intron (see also Examples 24–27).

Example 22

BAC Recombination without Drug Selection

The high efficiency of recombination described in Example 18 and elsewhere in these examples suggested that targeting could be done without drug selection. Direct targeting without drug selection would offer a number of significant advantages. In particular, it would facilitate genomic experiments in which the presence of a selectable marker, or even a frt or LoxP, scar might be undesirable.

To demonstrate that targeting can be achieved without drug selection, a 24 bp FLAG tag was targeted to the 5' end of the SRY-box containing gene 4 (Sox4) gene carried on a 125 kb BAC. For these experiments, a 114 bp targeting cassette was generated in which two 45-bp arms homologous to the Sox4 gene flanked the 24-bp FLAG sequence. This DNA fragment was created by synthesizing two 79-bp oligonucleotides that overlapped at their 3' ends by 44 bp. These overlaps were annealed and filled in by Taq polymerase.

Expression of lambda recombinase genes from the defective prophage was heat-induced in DY380 cells carrying the Sox4 BAC. Then, the FLAG-tagged cassette was introduced into the cells by electroporation. The cells were then spread on LB plates to a density of ~2,000 cells per plate. Colonies containing the FLAG tag were subsequently identified by colony hybridization using a 30-bp FLAG-specific oligonucleotide probe (24 bp FLAG tag and 3 bp on each side that was homologous to the Sox4 targeted site).

Among 3,800 colonies screened from uninduced cells, no FLAG-positive colonies were identified. In contrast, seven FLAG-positive colonies were identified in 4,210 colonies obtained from induced cells for an overall targeting frequency of $1.7 \times 10^{-3}$. PCR amplification and direct sequencing showed that each of the seven FLAG-positive colonies was correctly targeted.

As unequivocally demonstrated in this example, the surprisingly high recombination efficiency offered by this recombination system makes it possible to manipulate BAC or other DNA without drug selection. Point mutations, deletions, or insertions can now be engineered into any gene on a BAC in the absence of a confounding linked drug selection marker or a LoxP or frt site. In cases where the gene is mutated in human disease, the exact disease-causing mutations can be engineered on the BAC and the effect of these mutations analyzed in transgenic mice.

Example 23

Materials and Methods for Examples 24–27

Bacterial Strains. The *E. coli* strains used in Examples 24–27 are listed in Table 9, below.

TABLE 9

| Recombineering reagents | |
|---|---|
| | Genotype |
| Strains | |
| DH10B | F⁻ mcrA Δ(mrr-hsdRMS-mcrBC) Ø80dlacZΔM15 ΔlacX74 deoR recA1 endA1 araD139 Δ(ara, leu)7649 galU galK rspL nupG |
| DY380 | DH10B [λcI857 (cro-bioA <> tet] |
| EL250 | DH10B [[λcI857 (cro-bioA <> araC-P$_{BAD}$flpe] |
| EL350 | DH10B [[λcI857 (cro-bioA <> araC-P$_{BAD}$cre] |
| Selection Cassettes | |
| PL451 | FRT-PGK-EM7-NeobpA-FRT-loxP |
| PL452 | LoxP-PGK-EM7-NeobpA-loxP |
| Other Plasmids | |
| pSK+ | pBluescript |
| PL253 | Modified MC1TK |

EL350 cells were derived by transferring the defective λ prophage present in DY330 cells (Yu et al., *Proc Natl Acad Sci U.S.A.* 97:5978–5983, 2000) into DH10B cells, to create DY380 cells (Lee et al., *Genomics* 73: 56–65, 2001). An arabinose-inducible Cre gene (P$_{BAD}$-cre) was then introduced into the defective λ prophage present in DY380 cells to create EL350 cells (Lee et al., supra, 2001). DH10B cells have been used to construct most BAC libraries and are highly permissive for BAC transformation, while DY330 cells are relatively resistant to BAC transformation. BACs were identified from the CITB BAC library constructed from CJ7 (129/Sv) ES cells (Research Genetics). DH10B electrocompetent cells were purchased from Invitrogen.

Construction of Retrieval and Targeting Vectors: PCR primers were designed using MacVector. Primer sequences used for constructing the Evi9 conditional knockout vector are listed below:

```
Primer A: NotIEvi9-ex4-Ret-5'-1,      5'-ATAAGCGGCCGCTCTAATACAGAC-TGGCACCTG-3'      (SEQ ID NO: 38)

Primer B: H3Evi9-ex4-ret-5'-2,        5'-GTCAAGCTTTAAAGA-GATCCCTGCTATAAA-3';         (SEQ ID NO: 39)

Primer Y: H3Evi9-ex4-Ret-3'-1,        5'-GTCAAGCTTCCTGTTTCCAGCGTAG-GTGAA-3';         (SEQ ID NO: 40)

Primer Z: SpeIEvi9-ex4-ret-3'-2,      5'-TCTACTAGTCTCACC-ACCTGTACAGTAAGT-3';         (SEQ ID NO: 41)

Primer C: NotIEvi9-ex4-5'L-1,         5'ATAAGCGGCC-GCAACAATTAGTGTGTTTCCAGTT-3';      (SEQ ID NO: 42)

Primer D: EcoRI-BglII-Evi9-ex4-5'L-2, 5'-GTCGAATTCAGATCTAAATGG-GGTACTGAGACAAG-3';    (SEQ ID NO: 44)
```

```
Primer E: BamHIEvi9-ex4-5'R-1,      5'-ATAGGATC-CAACCAATGAGACAGTGGCACA-3';       (SEQ ID NO: 45)

Primer F: SalIEvi9-ex4-5'R-2,       5'-GTC-GTCGCACTTATTCATGTTCCAAC-AA-CCA-3;    (SEQ ID NO: 46)

Primer G: NotIEvi9-ex4-3'L-1        5'-ATAAGCGGCCGCCTTAACT-TAGACAGCATGTAT-3',   (SEQ ID NO: 47), Primer H: EcoRI-Evi9-exon4-3'L-2,   5'-GTCGAAT-TCGTCTGCAGAGGGTTAGTCAA-3';       (SEQ ID NO: 48)

Primer I: BamHI-Evi9-ex4-3'R-1,     5'-ATAGGATCCAGAGCAGATAGCAGTGAAAA-3';        (SEQ ID NO: 49)

Primer J: SalIEvi9-ex4-3'R-2,       5'GTCGTCGCATATTACCTCACCCAATGC-TA-G-3'.     (SEQ ID NO: 50)
These primers amplify the following size fragments:
500 bp with primers A, B;
295 bp with primers Y, Z;
222 bp with primers C, D;
276 bp with primers E, F;
277 bp with primers G, H;
and 227 bp with primers I, J.
```

PCR amplification: (ROCHE Expand High-Fidelity Taq kit) was performed by setting up the first reaction mixture containing 1 μl dNTP (10 mM), 1 μl DNA (10 ng BAC DNA), 1 μl (10 μM) of each primer, and 21 μl water. Then, a second reaction mixture was set up that contained 5 μl of 10× PCR buffer (#2), 0.75 μl high-fidelity Taq (5 μl/μl), and 20 μl water. The two reaction mixtures were then combined. PCR was performed using a PE-9700 PCR machine with the following settings: 94° C. for 2 minutes, then 10 cycles of 94° C. for 15 seconds, 55° C. for 30 seconds, 70° C. for 1 minutes. This was followed by 15 cycles of 94° C. for 15 seconds, 55° C. for 30 seconds, 70° C. for 1 minutes, with an additional 5 sec extension time each cycle. 5 μl of the 50 μl PCR reaction mixture was loaded onto a gel to check the PCR reaction. The remaining 45 μl was mixed with 225 μl PB from Qiagen and loaded onto a Qiagen mini-preparation spin column. After a 30-second spin, the column was washed once with 750 μl PE buffer. The PCR fragments were eluted using 30 μl of EB from Qiagen. 3 μl of restriction buffer (10×) and 1 μl of restriction enzyme was added and the mixture incubated at 37° C. for 1 hour. The digested PCR fragments were purified again with the columns and were ready for ligation.

The retrieval vector was generated by mixing 3μl of PCR product 1 (left arm, NotI/HindIII), 3 μl PCR product 2 (right arm, HindIII/SpeI), 2 μl MC1TK (PL253) (NotI/SpeI), 1 μl 10× ligation buffer and 1 μl T4 DNA ligase.

The Neo-targeting vector was generated by mixing 3 μl of PCR product 1 (left arm, NotI/EcoRI), 3 μl PCR product 2 (right arm, BamHI/SalI), 2 μl floxed Neo cassette (PL452 or PL451) (EcoRI/BamHI), 1 μl pSK+(NotI/SalI), 1.2 μl 10× ligation buffer and 1 μl T4 DNA ligase. The ligation mixtures were incubated at 16° C. for 2 hours and 0.5 μl was transformed into electro-competent DH10B cells (Invitrogen).

Transformation of BAC or Plasmid DNA into Recombinogenic Strains. E. coli cells with BACs were grown overnight in 5 ml LB broth with chloramphenicol. The LB broth used in contained only 5 g NaCl per liter. Cells were collected in three eppendorf tubes (2 ml) and were resuspended in 250 μl P1 from Qiagen. 250 μl P2 and 350 μl P3 were then added to each tube and the tubes spun for 4 minutes. The supernatant fluid from these tubes was transferred to new 1.5 ml eppendorf tubes, which were spun for another 4 minutes to clear the supernatant fluids. Finally, 750 μl isopropanol was added to precipitate the DNA (room temperature for 10 minutes) and the DNA collected by spinning the tubes for 10 minutes at the maximal speed. The DNA pellet was washed once with 1.0 ml 70% ethanol, dried and resuspended in 50 μl TE (total from 3 tubes). 1 μl DNA was used for electroporation and 10 μl for digestion (20 ng RNase was added to clear the RNA). Only freshly prepared BAC DNA was used for transformation.

EL350 or DY380 cells were grown in 5 ml LB broth in a Falcon 14 ml polypropylene round-bottom tube at 32° C. overnight with shaking. The next day the cells (OD600=1.2) were collected by centrifuging at 4000 rpm (0° C.) for 5 minutes in Oak Ridge tubes. Cell pellets were resuspended in 888 μl ice-cold water. Cells were transferred to a 1.5 ml eppendorf tube (on ice) and centrifuged using a benchtop centrifuge for 15–20 seconds at room temperature. The tubes were placed on ice and the supernatant fluids aspirated. The process was repeated two more times. Finally, the cell pellet was resuspended in 50 μl ice-cold water and transferred to a pre-cooled electroporation cuvette (0.1 cm gap). 1 μl BAC DNA (100 ng) or plasmid DNA (1.0 ng) was added and mixed. Electroporation was performed using a BIO-RAD electroporator under the following condition: 1.75 kV, 25 uF with pulse controller set at 200 ohms. The time constant was usually set at 4.0. 1.0 ml LB was added to each cuvette, which was incubated at 32° C. for one hour. Cells were spread on plates with the appropriate antibiotics.

Retrieving: EL350 cells containing BAC-A12 were inoculated into 5 ml of LB broth in a Falcon 14 ml polypropylene round-bottom tube and grown at 32° C. overnight with shaking. The next day, 1.0 ml of the overnight culture (OD600=1.2) was transferred to 20 ml LB (OD600=0.05–0.1) and incubated for 2 hours with shaking (180 rpm, OD600=0.5). 10 ml of the cells were then transferred to a new flask and shaken in a 42° C. water bath for 15 minutes. The cells were put into wet ice and the flask shaken to make sure that the temperature of the flask dropped as fast as possible. The flask was left in wet ice for another 5 minutes. The cells were transferred to 25 ml glass centrifuge tubes and spun at 4000 rpm (0° C.) for 5 minutes (with rubber adaptors). Cells were resuspended in 888 μl ice-cold water and transferred to a 1.5 ml eppendorf tube (on ice) and washed three times with ice-cold water as described above. Finally, the cell pellet was resuspended in 50 μl ice-cold water. 1–2 μl of the purified PCR or plasmid fragment was added and electroporated as described above.

Targeting: Frozen EL350 electro-competent cells were used for targeting in co-electroporation. The frozen cells were produced by adding a 10 ml overnight culture of EL350 (grown in two 14 ml tubes, OD600=1.2) to 500 ml LB broth in a 2-liter flask. The culture was then placed in a waterbath shaker at 32° C. until OD600=0.5 (~2.0 hour). The flask was then transferred to a 42° C. waterbath shaker and incubated for 15 minutes. The flask was immediately put into an ice slurry and shaken for 5 minutes by hand to make sure the temperature dropped as fast as possible. The flask was put on ice for an additional 10 minutes. Cells were collected at 4000 rpm at 0° C. for 5 minutes and washed three times with ice-cold water and once with cold 15% glycerol in water. Finally, cells were resuspended in 4 ml ice-cold 15% glycerol in water. 50 µl of the cells were aliquoted to pre-cooled eppendorf tubes (80 tubes total) and stored at −80° C.

For electroporation, the frozen cells were thawed at room temperature and quickly put on ice. Co-transformation of the purified targeting cassette (100 ng in 1 µl EB) and the template plasmid DNA (10 ng in 1 µl EB) was performed using with a BIO-RAD electroporator as described previously.

Excision of the Neo Cassette: Frozen EL350 cells induced for Cre expression by prior growth in arabinose-containing medium were used for excision of the floxed Neo cassette. A 10 ml overnight culture of EL350 cells was added to 500 ml of LB broth in a 2-liter flask. The culture was placed in a water bath shaker at 32° C. until OD600=0.4 (2.0 hours, 180 rpm). 5 ml of 10% L(+)arabinose (Sigma A–3256) in $H_2O$ was added to the culture to a final concentration of 0.1 % and shaken at 32° C. for another hour. Cells were collected, cell pellets washed, and frozen as described above. 1 ng plasmid DNA was electroporated into 50 µl frozen competent cells. 1.0 ml LB broth was added to the electroporation cuvette. 10–100 µl of the cells were subsequently plated on an ampicillin plate and 100 µl on a kanamycin plate and incubated at 32° C. overnight. The ampicillin plate ideally has 10–100 colonies, and no colonies on the kanamycin plate. The following antibiotic concentrations were used in the experiments: kanamycin and chloramphenicol, 12.5 µg/ml for BACs, 25 µg/ml for multicopy plasmids; Ampicillin, 25 µg/ml for BACs, 100 µg/ml for pBluescript.

Gene Targeting in Mouse ES Cells : 20 ug NotI-linearized Evi9 cko-targeting vector (PL460) DNA was electroporated into 10×10⁶ CJ7 ES cells that were growing on mitomycin-C-inactivated STO cells. Transfectants were selected in M15 medium (15% fetal bovine serum in DMEM with 2 mM L-glutamine) with G418 (180 µg/ml) and ganciclovir (2 µM). Targeted clones were identified on Southern blots with the 5' and 3' probes.

Example 24

Subcloning DNA by GAP Repair

Conditional knockout (cko) targeting vectors can be made by using recombineering to introduce LoxP sites, and positive and negative selection markers, into BAC DNA by homologous recombination. The region of the BAC containing the LoxP sites, and positive and negative selection markers, is then excised from the BAC and transformed into ES cells. The introduction of LoxP sites into BACs is complicated, however, because most BAC vector backbones carry Lox sites. These sites must be removed before any further Lox sites are introduced into the BAC DNA. Additionally, BAC integrity needs to be examined after each modification, and this is difficult when the BAC inserts are large. By subcloning a 10–15 kb fragment of BAC DNA into a high copy plasmid vector such as pBluescript (pSK+) before the Lox sites are introduced, these problems can be eliminated.

Homologous recombination via a process known as gap repair provides a convenient method for subcloning DNA from BACs into pBluescript. The gap repair method used previously for subcloning BAC DNA is shown in FIG. 14. Here, the linearized pBluescript vector used for gap repair is generated by PCR amplification using two chimeric primers (Zhang et al. *Nat Genet* 30: 31–39, 2000; Lee et al., *Genomics* 73:56–65 2001). The 5' 50 nucleotides of each primer are homologous to the two ends of the BAC sequence to be subcloned, while the 3' 20 nucleotides of each primer are homologous to pBluescript DNA. The linearized, PCR-amplified pBluescript vector is electroporated into *E. coli* cells induced for exo, bet, and gam expression, and which carry the BAC. Homologous recombination between the BAC DNA and the linearized pBluescript vector generates a circular plasmid that can replicate in *E. coli*. Ampicillin resistance ($Amp^r$) can be used to select these circular products (FIG. 14).

In order to make subcloning by GAP repair possible, a BAC must be first transferred from its strain of origin (DH10B) into an *E. coli* strain that contains exo, bet, and gam. In the experiments described herein, BACs are transferred into EL350 *E. coli* cells (Examples 20–21). EL350 cells were made by constructing a defective lambda prophage in DH10B cells, to create DY380 cells (Example 18) since DH10B is one of the few *E. coli* strains known that can be efficiently transformed with BAC DNA. A Cre gene under the control of the arabinose inducible promoter, $P_{BAD}$, was then introduced into the defective prophage carried in DY380 cells, to produce EL350 cells (Lee et al., *Genomics* 73:56–65, 2001). In EL350 cells, the homologous recombination functions encoded by the red genes can be controlled by temperature, while the Cre gene can be controlled by arabinose. As disclosed herein, it is much easier to transform electro-competent EL350 or DY380 cells produced from overnight cultures, than from exponentially growing cells. When BAC DNA is electroporated into stationary electro-competent cells and the BAC-containing cells selected using the chloramphenicol resistance ($Cam^r$) gene that is carried in the BAC vector backbone, 100 to 1000 $Cam^r$ colonies are routinely obtained from 50 ng of BAC DNA, and virtually all of the colonies contain unrearranged BACs. A complete list of the reagents used in these studies can be found in Table 9.

Figure 15:
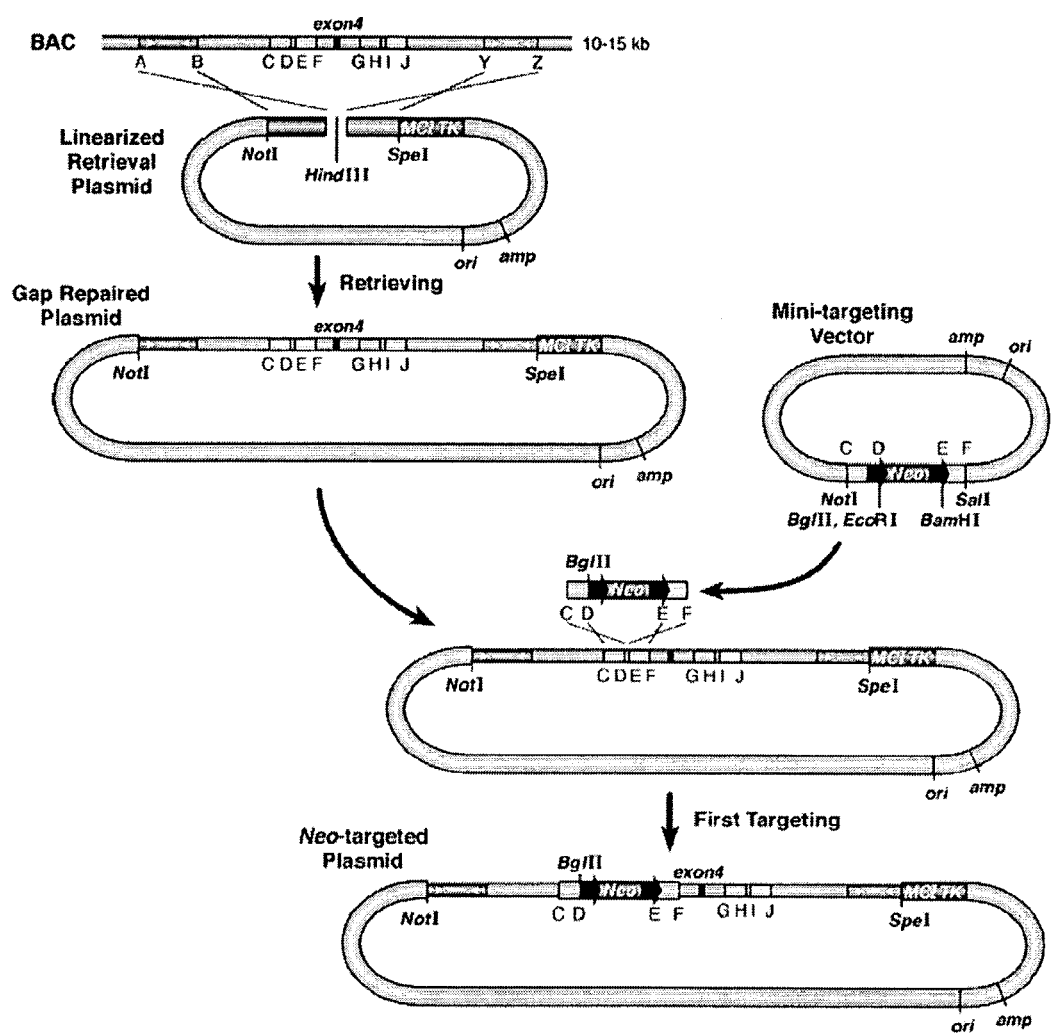
FIG. 15 is a schematic diagram of an improved procedure for subcloning DNA from BACs and for constructing cko-targeting vectors. The homology arms used for gap repair (subcloning) and for targeting, are PCR-amplified from BAC DNA. The two-homology arms (arrow, segments ending with AB or YZ, homologies indicated by light lines to plasmid), amplified using primers A and B or primers Y and Z, were cloned into a MC1TK-containing plasmid, to generate the gap repair (retrieval) plasmid for subcloning. The gap repair plasmid was linearized with HindIII to create a DNA double strand break for gap repair. A mini-targeting vector was constructed by ligating together the two PCR products generated by amplification of BAC DNA with primers C and D (segment indicated as ending with CD) or primers E and F (segments indicated as ending with EF), a floxed Neo selection cassette (black arrow: LoxP site), and pBluescript. A BglII restriction site was included in the mini-targeting vector for diagnosing gene targeting in ES cells. The black arrows denote LoxP sites. The targeting cassette was excised by NotI and SalI digestion, or by PCR amplification, using primers C and F. The gap-repaired plasmid, and the excised targeting cassette, were co-transformed into recombination-competent DY380 or EL350 cells. The recombinants had a floxed Neo cassette inserted between primers D and E and can be selected on kanamycin plates. The Neo cassette was excised with Cre recombinase, leaving a single LoxP site at the targeted locus (see FIG. 16). Similarly, a Neo selection cassette can be inserted between primers H and I using homology arms amplified by primers G, H (segment indicated as ending with GH), and I, J (segments indicated as ending with IJ).

An alternative method was used to subclone an 11.0 kb fragment of Evi9 spanning exon4, an alternative method for generating gap-repaired plasmids was designed that makes use of longer homology arms (200–500 bp; FIG. 17). As shown below, these larger homology arms significantly increase the frequency of subcloning by gap repair, and because of this, unwanted recombination products were rare. Another advantage of this alternative method is that the gap repair plasmid is not PCR amplified, which eliminates potential PCR artifacts introduced into the plasmid by PCR. In this alternative method, two sets of PCR primers were produced and used to amplify two 200–500 bp regions of the BAC (primers A and B and Y and Z; FIG. 15). Ultimately these two regions will mark the ends of the fragment to be subcloned by gap repair. The PCR products were purified using spin columns and digested with either NotI and HindIII or HindIII and SpeI. Restriction sites for these enzymes were included in the amplification primers in order to permit directional cloning of the PCR products into pBluescript. The digested-fragments were again purified and ligated to NotI- and SpeI-cut pBluescript DNA that also has a TK gene (MC1TK) gene for use in negative selection in ES cells. The retrieval vector was subsequently linearized with HindIII to create a DNA double strand break for gap repair.

Figure 16:
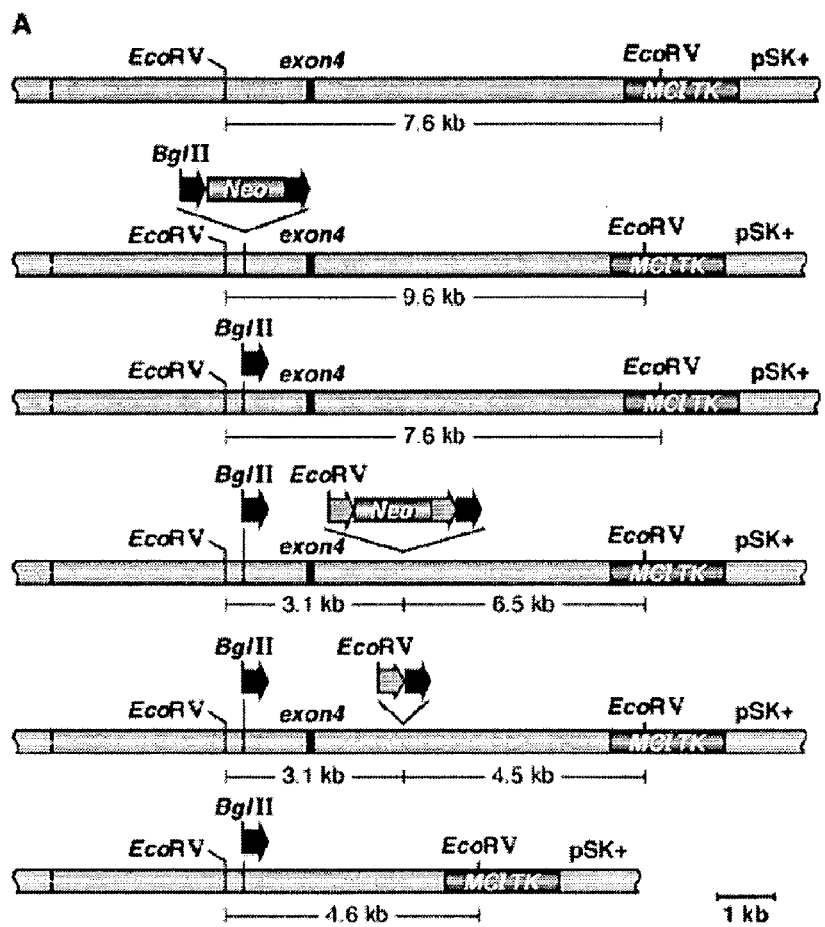
FIGS. 16A and 16B are sets of schematic diagrams and a digital image of the construction of an Evi9 conditional knockout allele.
Figure 16:
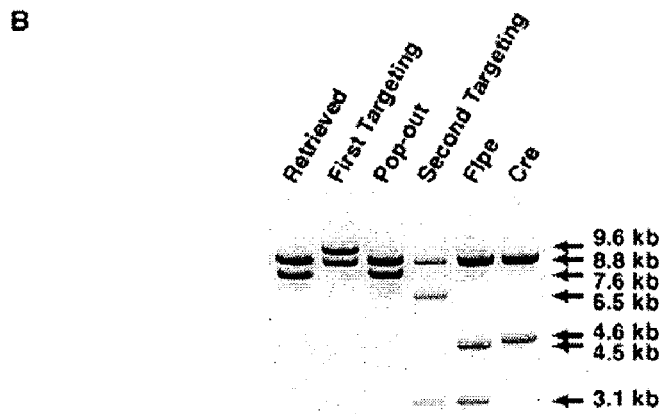

When 1 µl (50–100 ng) of the linear gap repair plasmid was electroporated into electro-competent EL350 cells, which contained Evi9 BAC A12, and which had been induced for exo, bet, and gam expression by prior growth at 42° C. for 15 minutes (FIG. 14), it was found that several thousand Amp$^r$ colonies were routinely generated in a single electroporation experiment. About 5% of these Amp$^r$ colonies were background colonies derived either from self-ligation of the linearized gap repair plasmid or from uncut DNA. The other 95% of the colonies contained gap-repaired plasmids with the expected genomic inserts (FIG. 16B, lane 1).

During the gap repair process, RecBCD is inhibited by Gam so that the linear gap repair plasmid is stable. However, in the absence of RecBCD, ColE1-derivative plasmids such as pBluescript can replicate by rolling circle replication. This type of replication will eventually convert the plasmid monomers into plasmid multimers (Feiss et al. *Gene* 17:123–130, 1982). As a result, huge plasmid complexes are produced in RecBCD-deficient cells. To select against these plasmid multimers following gap repair, a small amount of the gap-repaired plasmid DNA (1 ng) was re-transformed into wild type DH10B cells, and Amp$^r$ colonies selected. Empirically, it was determined that re-transformation selects for plasmids monomers and eliminates plasmid multimers.

Example 25

Targeting the First LoxP Site into the Subcloned Plasmid DNA

The next step in creating a cko-targeting vector is the introduction of a LoxP site into the subcloned DNA: in this case, 5' of Evi9 exon 4 (FIG. 15A). This is accomplished by introducing a floxed neomycin resistance (Neo) cassette (PL452) via homologous recombination into the subcloned plasmid DNA, and by removing the Neo gene via Cre recombinase. The floxed Neo gene in PL452 is expressed from a hybrid PGK-EM7 promoter. PGK permits efficient Neo expression in mammalian cells, while EM7 allows Neo to be expressed in bacterial cells. Subsequent removal of the floxed Neo gene via Cre recombinase leaves behind a single LoxP site at the targeted locus. In order to introduce a floxed Neo gene at the correct location, it is first flanked with 100–300 bp arms that are homologous to the targeting site. These homology arms, as described above, are generated by PCR amplification of the BAC DNA. In this case, the PCR primer pairs were engineered to contain NotI and EcoRI (primers C and D) or BamHI and SalI (primers E and F) restriction sites (FIG. 14). These restriction sites allow for the directional cloning of the homology arms, and the floxed Neo gene, into pBluescript. Primer D also contains a BglII site internal to the EcoRI site. The BglII site marks the presence of the LoxP site at the targeted locus following recombination in ES cells (see below). An EcoRV site was also incorporated into primer G for 3' side diagnosis of the targeting in ES cells (see below). Following PCR amplification, the products were purified, restriction digested and ligated to the floxed Neo cassette excised from PL452 with EcoRI and BamHI, and to pBluescript that was linearized by NotI and SalI digestion (FIG. 14). Four to six colonies selected by their kanamycin resistance, conferred by Neo, were picked and checked by restriction enzyme digestion to ensure that they were properly constructed. Usually, all of the Kan$^r$ colonies were properly constructed. This plasmid was referred to as the mini-targeting vector. The floxed Neo gene, together with the homology arms, was excised from pBluescript by NotI and SalI digestion, and gel-purified. The purified Neo cassette (150 ng) was co-electroporated along with the gap-repaired subcloned DNA (PL441, 10 ng) into EL350 cells, which had been induced for Red recombination functions by prior growth at 42° C. for 15 minutes, and frozen at −80° C. Transformants were selected on kanamycin plates.

In one experiment, 84 Kan$^r$ colonies were obtained following electroporation of induced EL350 cells, while only 6 colonies were obtained from uninduced cells. All the six colonies were identical to the original mini-targeting vector, suggesting that they represented uncut plasmid. Plasmids from six of the Kan$^r$ colonies from induced EL350 cells were examined by restriction enzyme digestion to make sure they were the correct recombinants. All 6 colonies gave the expected restriction patterns (FIG. 16B, lane 2).

Not all plasmids in a Kan$^r$ cell will carry the Neo cassette. This is especially true for high copy plasmids such as pBluescript since one recombinant plasmid molecule will render the cell Kan$^r$. The cells will therefore carry mixtures of targeted and non-targeted plasmids following recombination. This problem can be reduced if only a small amount of the gap-repaired subcloned plasmid DNA (1 ng) is used for co-electroporation. Alternatively, the mixed plasmids can be retransformed into DH10B cells and grown on kanamycin plates. Since most transformed cells will only receive one plasmid, growth of the transformed cells on kanamycin plates will select against cells that receive non-targeted plasmids, and the surviving colonies will carry pure populations of targeted plasmids.

Excision of the Neo cassette from the subcloned DNA was accomplished by electroporating the targeted plasmid DNA into EL350 cells, which had been induced for Cre expression by prior growth in arabinose-containing media for one hour. The electroporated cells were plated on either ampicillin or kanamycin plates. Cre-mediated recombination is highly efficient; therefore, the kanamycin plates usually do not have any colonies. Colonies from the ampicillin plates were checked for their kanamycin sensitivity and restriction digestion patterns to make sure that the floxed Neo cassette was properly excised. All 12 Amp$^r$ colonies picked for analysis in this experiment were kanamycin sensitive, and contained a single LoxP site at the targeted locus (FIG. 16B, lane 3).

Example 26

Targeting a Second LoxP Site Downstream of Evi9 Exon 4

The final step in this example of the construction of the cko-targeting vector is the introduction of a second LoxP into the subcloned DNA; in this case, downstream of Evi9 exon 4 (FIG. 16A). One way to accomplish this task is to again introduce a floxed Neo gene into the subcloned DNA, and then remove the floxed Neo gene via Cre recombinase, leaving behind a LoxP site at the second targeted locus. This is, however, complicated by the fact that the Neo gene serves as the selectable marker for gene targeting in ES cells; therefore the Neo gene can only be removed after Neo positive ES cells are selected and homologous recombinants identified. Transient expression of Cre recombinase in ES cells can generate three different excision products: two recombination products are generated by recombination between the LoxP site located upstream of Evi9 exon 4 and the two LoxP sites located downstream of Evi9 exon 4, which flank the Neo gene. The third, and desired recombination product, results from recombination between the two-LoxP sites located on either side of the Neo gene. Often, it seems that most recombination products are the undesired ones, and in some cases, it can be difficult to obtain ES cells that contain the desired product. Another problem stems from the fact that the Neo gene in a previously constructed cassette (PGK-Tn5-Kan-bpA) is optimized for expression in *E. coli*. Generally, 90% less ES colonies are obtained when this cassette is used than when a conventional PGKNeobpA is used.

To overcome these problems, a new selection cassette (PL451) was constructed. PL451 was constructed by introducing a frt site upstream of Neo, and frt and LoxP sites downstream of Neo, in PGKNeobpA, a selection cassette that is commonly used for gene targeting in ES cells (FIG. 16A). Similar to PL452, a bacterial EM7 promoter was introduced in between the PGK promoter and the coding sequence of Neo. This selection cassette works efficiently in both *E. coli* and mouse ES cells. frt is the DNA recognition site for Flp recombinase. DNA located between two frt sites in mouse ES cells can be excised by transient expression of a genetically enhanced Flp recombinase (Flpe) (Buchholz et al., *Nat Biotechnol* 16:657–662 1998), that works well in ES cells. In this case, single frt and single LoxP sites, were left behind at the targeted locus (FIG. 16A). Only one Flpe recombination product is possible, which ensures that all excision products are the correct ones. Alternatively, the PL451 selection cassette can be removed after the conditional allele is introduced into the mouse germ line by breeding the mice to one of the mouse strains that expresses Flpe in the mouse germ line (Rodriguez et al., 2000). Subsequent expression of Cre recombinase will excise the entire DNA between the LoxP sites located on either side of Evi9 exon 4, and create an Evi9 null allele. Cre can be expressed in the mouse germ line to create a germ line null allele, or in somatic cells.

The PL451 selection cassette was introduced into the subcloned DNA in the same manner used to introduce the floxed Neo gene upstream of Evi9 exon 4. Evi9 exon 4, including both targeted regions, was sequenced to make sure that no undesired mutations were introduced during the recombination process. To functionally test the LoxP and FRT sites in the targeting vector, the cko-targeting vector plasmid DNA was transformed into arabinose-induced EL350 and EL250 cells (EL250 cells have a Flpe gene under the control of the arabinose inducible promoter, $P_{BAD}$ (Lee et al., 2001)), respectively. Cells were plated on ampicillin plates to select for the plasmid. Plasmid DNA was prepared and digested to confirm the expected recombination patterns (FIG. 16B, lanes 5 and 6).

Example 27

Gene Targeting in ES Cells

The cko-targeting vector was subsequently linearized with NotI, electroporated into CJ7 ES cells, and the transformants selected for their G418 and ganciclovir (Ganc) resistance. Homologous recombination can occur either upstream or downstream of the LoxP site located 5' of Evi9 exon 4. Since a BglII site was introduced along with the upstream LoxP site, homologous recombinants carrying this LoxP site (the cko allele) will generate a 18.1 kb (wild type) and a 5.5 kb (mutant) BglII fragment using a 5' probe (FIG. 17A). Since an EcoRV site was introduced along with the selection cassette to the region downstream of exon 4, targeted clones will also have a 6.3 kb EcoRV fragment detected by the 3' probe (FIG. 17A). In one electroporation experiment, 300 G418$^r$ Ganc$^r$ colonies were obtained following electroporation. Eighty colonies were picked for Southern analysis. Twenty-four out of the 80 colonies (30%) had the Evi9 cko allele (FIG. 17B).

Thus, a rapid and efficient method for generating cko-targeting vectors is disclosed herein. This method relies on *E. coli* recombineering rather than restriction enzymes and DNA ligases for vector construction (FIG. 18). This method makes use of high copy plasmids rather than BAC DNA to generate the targeting vector, 200–500 bp of homology for subcloning (gap repair), and 100–300 bp of homology for targeting, rather than the 45–50 bp of homology used in previous experiments (e.g. see Example 5). By using high copy plasmid DNA for vector construction, the problem caused by Lox sites present in the BAC vector backbone is eliminated, and by using longer homology arms, as many as 10,000 colonies can be obtained from a single subcloning experiment with only 50–100 ng of retrieving plasmid DNA. In addition, more than 95% of the colonies are correctly constructed. This is in contrast to previous subcloning methods using shorter regions of homology. Moreover, using these longer homology arms, targeting frequencies as high as $1 \times 10^{-2}$ can be obtained with as little as 100 ng of targeting DNA (i.e., targeting a floxed Neo cassette to a BAC).

In order to use high copy plasmids such as pBluescript for vector construction, modifications were made in the way the λ Red system was used. For example, co-electroporation was used to target the floxed Neo cassette to the plasmid, instead of introducing the Neo cassette into cells that already carried the plasmid. Induction of the λ Red genes into cells that carry multiple plasmids can cause the formation of plasmid complexes due to rolling-circle replication (Feiss et al., *Gene* 17:123–130, 1992). Co-transformation of the Neo cassette and the plasmid minimizes this problem, but still provides a high enough frequency of homologous recombination to generate the targeted plasmid. Cre-expressing EL350 cells were also used to excise the floxed Neo cassette from the targeted plasmid. When multiple plasmid molecules containing LoxP sites are present in a cell expressing Cre, intermolecular recombination between the LoxP sites can occur, resulting in plasmid loss. Electroporation of a small amount of plasmid DNA containing the floxed Neo cassette into Cre-expressing EL350 cells avoids this problem, yet still allows for the efficient excision of the Neo cassette. Two new selection cassettes (loxP-PGK-EM7-NeobpA-loxP and FRT-PGK-EM7-NeobpA-FRT-loxP) were also constructed that worked well in both *E. coli* and mouse ES cells. The second selection cassette contains two frt sites and one LoxP site that flank the selection cassette. This makes it possible to remove this selection cassette following homologous recombination in ES with Flpe recombinase, leaving behind frt-LoxP sites at the targeted locus.

Additionally, 200–500 bp homology arms that contain SINE, LINE or short DNA repeats such as CA repeats have been used for retrieving and targeting. Efficient recombination was still achieved in all cases. In some circumstances, longer homology arms can help in avoiding problems created by sequencing errors in the public databases, or strain polymorphisms. This can be of use when modifying human DNA where polymorphisms are common. With its high efficiency and reliability, more than ten cko-targeting vectors have been constructed. Four of the cko-targeting vectors have been introduced into ES cells for homologous recombination. All four targeting constructs gave rise to highly efficient gene targeting frequencies in mouse ES cells: the frequency of cko alleles ranged from 20 to 40% of the G418$^r$, Ganc$^r$ colonies.

The most time-consuming step in constructing the cko-targeting vector using this method is in the production of the retrieval vector and the two mini-targeting vectors. However, since all of the homology arms used in the construction of these vectors are PCR-amplified from BAC DNA, only single PCR products are usually obtained, and the PCR products can thus be easily purified using spin columns. All six PCR reactions needed to construct a cko vector, including digestion of the PCR products and ligation and transformation, can be done in one day. Typically, it takes less than two weeks to construct a cko-targeting vector using this method, and multiple cko vectors can be generated simultaneously. An alternative way to generate longer homology arms for homologous recombination is by using two-step fusion PCR originally designed for enhanced homologous recombination in yeast (Wach, *Yeast* 12:259–265, 1996). With two-step fusion PCR, the two PCR products are amplified that serve as homology regions. Since about 26 base pairs of selection marker sequences are included in two of the four primers used to amplify the homology regions, one strand of each of the two PCR products can serve as the primer for amplifying the selection marker (Wach, *Yeast* 12:259–265, 1996).

By using BACs rather than phage libraries for vector construction, one can precisely choose a genomic region to retrieve for further manipulation. Moreover, BACs, and DNA subcloned from BACs into high copy plasmids, can be rapidly modified using the methods described here to create knock-in mutations and transgene constructs, as well as expedite the analysis of regulatory elements and functional domains in or near genes via deletion analysis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

We claim:

1. A method for inserting a nucleic acid molecule into a target nucleic acid in an isolated host cell, the method comprising
    introducing into the host cell a single stranded nucleic acid of at least 30 nucleotides in length sufficiently homologous for recombination to occur with the target nucleic acid, but not identical to the target nucleic acid, wherein the host cell comprises a nucleic acid sequence encoding Beta operably linked to a de-repressible promoter; and
    inducing expression of Beta from the de-repressible promoter, thereby inducing homologous recombination between the single stranded DNA and the target nucleic acid, and thereby introducing the nucleic acid molecule into the target nucleic acid.

2. The method of claim 1, wherein the single stranded nucleic acid is at least 40 nucleotides in length.

3. The method of claim 1, wherein the single stranded nucleic acid is at least 50 nucleotides in length.

4. The method of claim 1, wherein the single stranded nucleic acid is at least 70 nucleotides in length.

5. The method of claim 1, wherein the cell is a bacterial cell.

6. The method of claim 1, wherein the cell is a eukaryotic cell.

7. The method of claim 1, wherein the cell is a plant cell.

8. The method of claim 1, wherein the cell is a yeast cell.

9. The method of claim 1, wherein the single stranded nucleic acid is homologous to a lagging strand of the target nucleic acid.

10. The method of claim 1, wherein the target nucleic acid is a bacterial artificial chromosome (BAC), P1 artificial chromosome, or yeast artificial chromosome.

11. The method of claim 1, wherein the cell does not express Exo or Gam.

12. The method of claim 1, wherein the cell comprises a vector comprising the target nucleic acid sequence.

13. The method of claim 1, wherein the cell comprises an extrachromosomal element comprising the target nucleic acid sequence.

14. The method of claim 1, wherein a chromosome of the cell comprises the target nucleic acid sequence.

15. The method of claim 1, wherein the de-repressible promoter is pL.

16. A method of introducing a mutation into a target nucleic acid in an isolated cell, comprising
    introducing a first single stranded nucleic acid of at least 30 nucleotides in length homologous to the target nucleic acid into the cell; wherein the first single stranded nucleic acid is not identical to the target nucleic acid, and wherein the cell comprises a de-repressible promoter operably linked to a nucleic acid sequence encoding Beta, and wherein the cell does not express Exo or Gam; and
    inducing the expression of Beta from the de-repressible promoter, wherein Exo and Gam are not expressed in the cell, thereby inducing recombination of the first single stranded nucleic acid with the target nucleic acid in the cell, wherein the recombination of the first single stranded nucleic acid with the target nucleic acid introduces the mutation into the target nucleic acid.

17. The method of claim 16, wherein the cell is a bacterial cell.

18. The method of claim 16, wherein the cell is a eurkaryotic cell.

19. The method of claim 16, wherein the cell is a plant cell.

20. The method of claim 16, wherein the cell is a yeast cell.

21. The method of claim 16, wherein the first single stranded nucleic acid is homologous to a lagging strand of the target nucleic acid.

22. The method of claim 16, wherein the first single stranded nucleic acid is homologous to a leading strand of the target nucleic acid.

23. The method of claim 16, wherein the mutation is a deletion.

24. The method of claim 16, wherein the mutation is a point mutation.

25. The method of claim 16, wherein the mutation is an insertion.

26. The method of claim 16, further comprising
introducing a second single stranded nucleic acid of at least 30 nucleotides in length homologous to the target nucleic acid, wherein at least 20 bases of the second single stranded nucleic acid are complementary to the first single stranded nucleic acid such that a 3' overhang is produced.

27. The method of claim 16, further comprising
introducing a second single stranded nucleic acid of at least 30 nucleotides in length homologous to the target nucleic acid, wherein at least 20 bases of the second single stranded nucleic acid are complementary to the first single stranded nucleic acid such that a 5' overhang is produced.

28. The method of claim 16, wherein the de-repressible promoter is pL.

29. A method for inducing homologous recombination in an isolated cell comprising a target nucleic acid, the method comprising:
introducing into the cell a first nucleic acid of interest comprising a homologous sequence to the target nucleic acid of sufficient length to induce homologous recombination, wherein the cell comprises a nucleic acid encoding Beta or recT, operably linked to a pL promoter, and wherein the cell is prokaryotic cell; and
inducing sufficient expression of the nucleic acid encoding Beta or recT to promote homologous recombination of the first nucleic acid of interest with the target nucleic acid;
thereby inducing homologous recombination in the cell, wherein the first nucleic acid sequence of interest comprises single stranded DNA, and wherein the method further comprises introducing a second single-stranded DNA sequence, wherein the second single-stranded DNA sequence comprises more than 10 bases of complementary overlap at either the 5' or 3' terminus of the first nucleic acid of interest.

30. The method of claim 29, wherein the cell is an *Escherichia coli* cell.

31. The method of claim 29, wherein the first nucleic acid of interest encodes a selectable marker.

32. The method of claim 29, wherein the first nucleic acid of interest is a single stranded DNA and association of the first nucleic acid of interest with the second single stranded DNA produces a double stranded DNA comprising a single stranded overhang.

33. The method of claim 29, wherein the homologous sequence is at least 70 nucleotides in length.

34. The method of claim 29, wherein association of the first nucleic acid of interest with the second single stranded DNA produces a double stranded DNA comprising a homology arm.

35. The method of claim 34, wherein the homology arm is of at least 20 nucleotides in length.

36. The method of claim 29, wherein the cell comprises a nucleic acid encoding Beta.

\* \* \* \* \*

UNITED STATES PATENT AND TRADEMARK OFFICE
Certificate

Patent No. 7,144,734 B2                     Patented: December 5, 2006

On petition requesting issuance of a certificate for correction of inventorship pursuant to 35 U.S.C. 256, it has been found that the above identified patent, through error and without any deceptive intent, improperly sets forth the inventorship.
   Accordingly, it is hereby certified that the correct inventorship of this patent is: Donald L. Court, Frederick, MD (US); Daiguan Yu, Guangzhou (CN); E-Chiang Lee, The Woodlands, TX (US); Hilary M. Ellis, San Ramon, CA (US); Srividya Swaminathan, Normanton Park (SG); and Shyam K. Sharan, Frederick, MD (US).

Signed and Sealed this Eighteenth Day of November 2014.

ANNE GUSSOW
*Supervisory Patent Examiner*
Art Unit 1636
Technology Center 1600

SEQUENCE LISTING

```
<160> NUMBER OF SEQ ID NOS: 50

<210> SEQ ID NO 1
<211> LENGTH: 20
<212> TYPE: DNA
<213> ORGANISM: Artificial sequence
<220> FEATURE:
<223> OTHER INFORMATION: primer

<400> SEQUENCE: 1
tgtgacggaa gatcacttcg                                              20

<210> SEQ ID NO 2
<211> LENGTH: 20
<212> TYPE: DNA
<213> ORGANISM: Artificial sequence
<220> FEATURE:
<223> OTHER INFORMATION: primer

<400> SEQUENCE: 2
accagcaata gacataagcg                                              20

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
ctcttgggtt atcaagaggg                                              20

<210> SEQ ID NO 4
<211> LENGTH: 20
<212> TYPE: DNA
<213> ORGANISM: Artificial sequence
<220> FEATURE:
<223> OTHER INFORMATION: primer
```

-continued

```
<400> SEQUENCE: 4
actcgacatc ttggttaccg                                               20

<210> SEQ ID NO 5
<211> LENGTH: 21
<212> TYPE: DNA
<213> ORGANISM: Artificial sequence
<220> FEATURE:
<223> OTHER INFORMATION: primer

<400> SEQUENCE: 5
cattcaaata tgtatccgct c                                             21

<210> SEQ ID NO 6
<211> LENGTH: 20
<212> TYPE: DNA
<213> ORGANISM: Artificial sequence
<220> FEATURE:
<223> OTHER INFORMATION: primer

<400> SEQUENCE: 6
agagttggta gctcttgatc                                               20

<210> SEQ ID NO 7
<211> LENGTH: 20
<212> TYPE: DNA
<213> ORGANISM: Artificial sequence
<220> FEATURE:
<223> OTHER INFORMATION: primer

<400> SEQUENCE: 7
tatggacagc aagcgaaccg                                               20

<210> SEQ ID NO 8
<211> LENGTH: 21
<212> TYPE: DNA
<213> ORGANISM: Artificial sequence
<220> FEATURE:
<223> OTHER INFORMATION: primer

<400> SEQUENCE: 8
tcagaagaac tcgtcaagaa g                                             21

<210> SEQ ID NO 9
<211> LENGTH: 50
<212> TYPE: DNA
<213> ORGANISM: Artificial sequence
<220> FEATURE:
<223> OTHER INFORMATION: primer

<400> SEQUENCE: 9
gtttgcgcgc agtcagcgat atccattttc gcgaatccgg agtgtaagaa              50

<210> SEQ ID NO 10
<211> LENGTH: 50
<212> TYPE: DNA
<213> ORGANISM: Artificial sequence
<220> FEATURE:
<223> OTHER INFORMATION: primer

<400> SEQUENCE: 10
ttcatattgt tcagcgacag cttgctgtac ggcaggcacc agctcttccg              50

<210> SEQ ID NO 11
<211> LENGTH: 70
```

<212> TYPE: DNA
<213> ORGANISM: Artificial sequence
<220> FEATURE:
<223> OTHER INFORMATION: primer

<400> SEQUENCE: 11
aagtcgcggt cggaaccgta ttgcagcagc tttatcatct gccgctggac ggcgcacaaa    60
tcgcgcttaa    70

<210> SEQ ID NO 12
<211> LENGTH: 60
<212> TYPE: DNA
<213> ORGANISM: Artificial sequence
<220> FEATURE:
<223> OTHER INFORMATION: primer

<400> SEQUENCE: 12
aacagacacc atggtgcacc tgactcctga ggagaagtct gccgttactg ccctgtgggg    60

<210> SEQ ID NO 13
<211> LENGTH: 56
<212> TYPE: DNA
<213> ORGANISM: Artificial sequence
<220> FEATURE:
<223> OTHER INFORMATION: primer

<400> SEQUENCE: 13
ctgcaaggcg attaagttgg gtaacgccag ggttttcgtc aggtggcact ttcggg    56

<210> SEQ ID NO 14
<211> LENGTH: 23
<212> TYPE: DNA
<213> ORGANISM: Artificial sequence
<220> FEATURE:
<223> OTHER INFORMATION: primer

<400> SEQUENCE: 14
ctcagaagaa ctcgtcaaga agg    23

<210> SEQ ID NO 15
<211> LENGTH: 35
<212> TYPE: DNA
<213> ORGANISM: Artificial sequence
<220> FEATURE:
<223> OTHER INFORMATION: primer

<400> SEQUENCE: 15
gtaggtacct cgagaatcgc catcttccag caggc    35

<210> SEQ ID NO 16
<211> LENGTH: 36
<212> TYPE: DNA
<213> ORGANISM: Artificial sequence
<220> FEATURE:
<223> OTHER INFORMATION: primer

<400> SEQUENCE: 16
tcgaattttc tgcatccaat ttactgaccg tacacc    36

<210> SEQ ID NO 17
<211> LENGTH: 67
<212> TYPE: DNA
<213> ORGANISM: Artificial sequence
<220> FEATURE:
<223> OTHER INFORMATION: primer

```
<400> SEQUENCE: 17
gcaagtgtgt cgctgtcgac gagctcgcga gctcggacat gaggttgtct tagacgtcag    60
gtggcac                                                              67

<210> SEQ ID NO 18
<211> LENGTH: 69
<212> TYPE: DNA
<213> ORGANISM: Artificial sequence
<220> FEATURE:
<223> OTHER INFORMATION: primer

<400> SEQUENCE: 18
catagttaag ccagccccga cacccgccaa cacccgctga cgcgaacctc acgttaaggg    60
attttggtc                                                            69

<210> SEQ ID NO 19
<211> LENGTH: 29
<212> TYPE: DNA
<213> ORGANISM: Artificial sequence
<220> FEATURE:
<223> OTHER INFORMATION: primer

<400> SEQUENCE: 19
gcaggatcca gtttgctcct ggagcgaca                                      29

<210> SEQ ID NO 20
<211> LENGTH: 22
<212> TYPE: DNA
<213> ORGANISM: Artificial sequence
<220> FEATURE:
<223> OTHER INFORMATION: primer

<400> SEQUENCE: 20
tgcaggtcga ctctagagga tc                                             22

<210> SEQ ID NO 21
<211> LENGTH: 60
<212> TYPE: DNA
<213> ORGANISM: Artificial sequence
<220> FEATURE:
<223> OTHER INFORMATION: primer

<400> SEQUENCE: 21
tggcggtgat aatggttgca tgtactaagg aggttgtatg ctcttgggtt atcaagaggg    60

<210> SEQ ID NO 22
<211> LENGTH: 60
<212> TYPE: DNA
<213> ORGANISM: Artificial sequence
<220> FEATURE:
<223> OTHER INFORMATION: primer

<400> SEQUENCE: 22
ggcgctgcaa aaattctttg tcgaacaggg tgtctggatc actcgacatc ttggttaccg    60

<210> SEQ ID NO 23
<211> LENGTH: 61
<212> TYPE: DNA
<213> ORGANISM: Artificial sequence
<220> FEATURE:
<223> OTHER INFORMATION: primer

<400> SEQUENCE: 23
tggcggtgat aatggttgca tgtactaagg aggttgtatg ctgtgacgga agatcacttc    60
```

<210> SEQ ID NO 24
<211> LENGTH: 61
<212> TYPE: DNA
<213> ORGANISM: Artificial sequence
<220> FEATURE:
<223> OTHER INFORMATION: primer

<400> SEQUENCE: 24
ggcgctgcaa aaattctttg tcgaacaggg tgtctggatc ctgaggttct tatggctctt    60
g                                                                    61

<210> SEQ ID NO 25
<211> LENGTH: 60
<212> TYPE: DNA
<213> ORGANISM: Artificial sequence
<220> FEATURE:
<223> OTHER INFORMATION: primer

<400> SEQUENCE: 25
tggcggtgat aatggttgca tgtactaagg aggttgtatg aagcggcatg cataatgtgc    60

<210> SEQ ID NO 26
<211> LENGTH: 65
<212> TYPE: DNA
<213> ORGANISM: Artificial sequence
<220> FEATURE:
<223> OTHER INFORMATION: primer

<400> SEQUENCE: 26
ggcgctgcaa aaattctttg tcgaacaggg tgtctggatc ctgtgtccta ctcaggagag    60
cgttc                                                                65

<210> SEQ ID NO 27
<211> LENGTH: 63
<212> TYPE: DNA
<213> ORGANISM: Artificial sequence
<220> FEATURE:
<223> OTHER INFORMATION: primer

<400> SEQUENCE: 27
cgcttcgcgg gacataattt ccgaaatccc agtgtgctgt gagccaagct atcgaattcc    60
gcc                                                                  63

<210> SEQ ID NO 28
<211> LENGTH: 63
<212> TYPE: DNA
<213> ORGANISM: Artificial sequence
<220> FEATURE:
<223> OTHER INFORMATION: primer

<400> SEQUENCE: 28
gaggctccag gagaatgaga tgttcccgcg ttcaggcaag cgctattcca gaagtagtga    60
gga                                                                  63

<210> SEQ ID NO 29
<211> LENGTH: 79
<212> TYPE: DNA
<213> ORGANISM: Artificial sequence
<220> FEATURE:
<223> OTHER INFORMATION: primer

<400> SEQUENCE: 29
gcgagcgtgt gagcgcgcgt gggcgcccgg caagccgggg ccatggatta caaggatgac     60
gacgataagg tacaacaga     79

<210> SEQ ID NO 30
<211> LENGTH: 79
<212> TYPE: DNA
<213> ORGANISM: Artificial sequence
<220> FEATURE:
<223> OTHER INFORMATION: primer

<400> SEQUENCE: 30
ggccagcaga gcctcagtgt tctccgcgtt gttggtctgt tgtaccttat cgtcgtcatc     60
cttgtaatcc atggccccc     79

<210> SEQ ID NO 31
<211> LENGTH: 80
<212> TYPE: DNA
<213> ORGANISM: Artificial sequence
<220> FEATURE:
<223> OTHER INFORMATION: primer

<400> SEQUENCE: 31
ctctccatgc ctgtctgggt gagggtggcc caggggcgat ggctatgaga gaggtcgact     60
tcttagacgt caggtggcac     80

<210> SEQ ID NO 32
<211> LENGTH: 79
<212> TYPE: DNA
<213> ORGANISM: Artificial sequence
<220> FEATURE:
<223> OTHER INFORMATION: primer

<400> SEQUENCE: 32
gcaatgcaga gaagccttgt actgggatga cagagacgga ggggaagagg aggcggccgc     60
gatacgcgag cgaacgtga     79

<210> SEQ ID NO 33
<211> LENGTH: 80
<212> TYPE: DNA
<213> ORGANISM: Artificial sequence
<220> FEATURE:
<223> OTHER INFORMATION: primer

<400> SEQUENCE: 33
gacttctatg acctgtacgg aggggagaag tttgcgacgt gacagagctg gtcgtcgact     60
tcttagacgt caggtggcac     80

<210> SEQ ID NO 34
<211> LENGTH: 81
<212> TYPE: DNA
<213> ORGANISM: Artificial sequence
<220> FEATURE:
<223> OTHER INFORMATION: primer

<400> SEQUENCE: 34
gccccataca cgtaaatgta catagaatca cacagcatca cttctatgga tgcggcggcc     60
gcgatacgcg agcgaacgtg a     81

<210> SEQ ID NO 35
<211> LENGTH: 79

<212> TYPE: DNA
<213> ORGANISM: Artificial sequence
<220> FEATURE:
<223> OTHER INFORMATION: primer

<400> SEQUENCE: 35
catccagtag aacttgggag tgaagctaga gccaaggcca tctaagtgac aggcggccgc    60
gatacgcgag cgaacgtga    79

<210> SEQ ID NO 36
<211> LENGTH: 23
<212> TYPE: DNA
<213> ORGANISM: Artificial sequence
<220> FEATURE:
<223> OTHER INFORMATION: primer

<400> SEQUENCE: 36
ctgctggaag atggcgattc tcg    23

<210> SEQ ID NO 37
<211> LENGTH: 20
<212> TYPE: DNA
<213> ORGANISM: Artificial sequence
<220> FEATURE:
<223> OTHER INFORMATION: primer

<400> SEQUENCE: 37
aacagcagga gcggtgagtc    20

<210> SEQ ID NO 38
<211> LENGTH: 33
<212> TYPE: DNA
<213> ORGANISM: Artificial sequence
<220> FEATURE:
<223> OTHER INFORMATION: primer

<400> SEQUENCE: 38
ataagcggcc gctctaatac agactggcac ctg    33

<210> SEQ ID NO 39
<211> LENGTH: 30
<212> TYPE: DNA
<213> ORGANISM: Artificial sequence
<220> FEATURE:
<223> OTHER INFORMATION: primer

<400> SEQUENCE: 39
gtcaagcttt aaagagatcc ctgctataaa    30

<210> SEQ ID NO 40
<211> LENGTH: 30
<212> TYPE: DNA
<213> ORGANISM: Artificial sequence
<220> FEATURE:
<223> OTHER INFORMATION: primer

<400> SEQUENCE: 40
gtcaagcttc ctgtttccag cgtaggtgaa    30

<210> SEQ ID NO 41
<211> LENGTH: 30
<212> TYPE: DNA
<213> ORGANISM: Artificial sequence
<220> FEATURE:
<223> OTHER INFORMATION: primer

```
<400> SEQUENCE: 41
tctactagtc tcaccacctg tacagtaagt                                    30

<210> SEQ ID NO 42
<211> LENGTH: 34
<212> TYPE: DNA
<213> ORGANISM: Artificial sequence
<220> FEATURE:
<223> OTHER INFORMATION: primer

<400> SEQUENCE: 42
ataagcggcc gcaacaatta gtgtgtttcc agtt                               34

<210> SEQ ID NO 43
<211> LENGTH: 35
<212> TYPE: DNA
<213> ORGANISM: Artificial sequence
<220> FEATURE:
<223> OTHER INFORMATION: primer

<400> SEQUENCE: 43
gtcgaattca gatctaaatg gggtactgag acaag                              35

<210> SEQ ID NO 44
<211> LENGTH: 30
<212> TYPE: DNA
<213> ORGANISM: Artificial sequence
<220> FEATURE:
<223> OTHER INFORMATION: primer

<400> SEQUENCE: 44
ataggatcca accaatgaga cagtggcaca                                    30

<210> SEQ ID NO 45
<211> LENGTH: 31
<212> TYPE: DNA
<213> ORGANISM: Artificial sequence
<220> FEATURE:
<223> OTHER INFORMATION: primer

<400> SEQUENCE: 45
gtcgtcgcac ttattcatgt tccaacaacc a                                  31

<210> SEQ ID NO 46
<211> LENGTH: 33
<212> TYPE: DNA
<213> ORGANISM: Artificial sequence
<220> FEATURE:
<223> OTHER INFORMATION: primer

<400> SEQUENCE: 46
ataagcggcc gccttaactt agacagcatg tat                                33

<210> SEQ ID NO 47
<211> LENGTH: 29
<212> TYPE: DNA
<213> ORGANISM: Artificial sequence
<220> FEATURE:
<223> OTHER INFORMATION: primer

<400> SEQUENCE: 47
gtcgaattcg tctgcagagg gttagtcaa                                     29

<210> SEQ ID NO 48
<211> LENGTH: 29
```

```
<212> TYPE: DNA
<213> ORGANISM: Artificial sequence
<220> FEATURE:
<223> OTHER INFORMATION: primer

<400> SEQUENCE: 48
ataggatcca gagcagatag cagtgaaaa                                      29

<210> SEQ ID NO 49
<211> LENGTH: 30
<212> TYPE: DNA
<213> ORGANISM: Artificial sequence
<220> FEATURE:
<223> OTHER INFORMATION: primer

<400> SEQUENCE: 49
gtcgtcgcat attacctcac ccaatgctag                                     30

<210> SEQ ID NO 50
<211> LENGTH: 34
<212> TYPE: DNA
<213> ORGANISM: Artificial sequence
<220> FEATURE:
<223> OTHER INFORMATION: primer

<400> SEQUENCE: 50
ataacttcgt ataatgtatg ctatacgaag ttat                                34
```